US012685773B2

(12) United States Patent
Myo et al.

(10) Patent No.: US 12,685,773 B2
(45) Date of Patent: Jul. 21, 2026

(54) TREATMENT OF CD30-POSITIVE CANCER

(71) Applicant: The University of North Carolina at Chapel Hill, Chapel Hill, NC (US)

(72) Inventors: Aung Myo, Singapore (SG); Ivan David Horak, Singapore (SG); Jonathan Serody, Chapel Hill, NC (US); Gianpietro Dotti, Chapel Hill, NC (US); Barbara Savoldo, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 596 days.

(21) Appl. No.: 18/007,709

(22) PCT Filed: Jun. 4, 2021

(86) PCT No.: PCT/EP2021/065037
§ 371 (c)(1),
(2) Date: Dec. 1, 2022

(87) PCT Pub. No.: WO2021/245249
PCT Pub. Date: Dec. 9, 2021

(65) Prior Publication Data
US 2023/0263890 A1      Aug. 24, 2023

Related U.S. Application Data

(60) Provisional application No. 63/035,104, filed on Jun. 5, 2020.

(51) Int. Cl.
| | |
|---|---|
| *A61K 40/42* | (2025.01) |
| *A61K 31/4184* | (2006.01) |
| *A61K 31/7076* | (2006.01) |
| *A61K 40/11* | (2025.01) |
| *A61K 40/24* | (2025.01) |
| *A61K 40/31* | (2025.01) |
| *A61P 35/00* | (2006.01) |
| *C07K 14/705* | (2006.01) |
| *C07K 14/725* | (2006.01) |

(52) U.S. Cl.
CPC ...... *A61K 40/4215* (2025.01); *A61K 31/4184* (2013.01); *A61K 31/7076* (2013.01); *A61K 40/11* (2025.01); *A61K 40/24* (2025.01); *A61K 40/31* (2025.01); *A61K 40/421* (2025.01); *A61K 40/4224* (2025.01); *A61P 35/00* (2018.01); *C07K 14/7051* (2013.01); *C07K 14/70521* (2013.01); *C07K 14/70578* (2013.01); *A61K 2239/31* (2023.05); *A61K 2239/38* (2023.05); *A61K 2239/48* (2023.05); *C07K 2317/53* (2013.01); *C07K 2319/02* (2013.01); *C07K 2319/03* (2013.01)

(58) Field of Classification Search
CPC ..................................................... A61K 40/31
See application file for complete search history.

(56) References Cited

U.S. PATENT DOCUMENTS

| | | | |
|---|---|---|---|
| 2016/0200824 A1* | 7/2016 | Chmielewski | .......... A61P 35/00 435/328 |
| 2020/0016199 A1 | 1/2020 | Turtle et al. | |

FOREIGN PATENT DOCUMENTS

WO      WO 2015/028444 A1      3/2015

OTHER PUBLICATIONS

International Search Report and Written Opinion for Application No. PCT/EP2021/065037, mailed Sep. 9, 2021.
Grover et al., A Phase Ib/II Study of Anti-CD30 Chimeric Antigen Receptor T Cells for Relapsed/Refractory CD30+ Lymphomas. Abstract/Biol Blood Marrow Transplant. 2019; 25: S66.
Ramos et al., CD30-Chimeric Antigen Receptor (CAR) T Cells for Therapy of Hodgkin Lymphoma (HL). Abstract/Biol Blood Marrow Transplant. 2019; 25: S63.

\* cited by examiner

*Primary Examiner* — Christopher M Babic
*Assistant Examiner* — Jennifer S Spence
(74) *Attorney, Agent, or Firm* — Myers Bigel, P.A.

(57) ABSTRACT

Methods for treating a CD30-positive cancer in a subject are disclosed, wherein the methods comprise administering a lymphodepleting chemotherapy and CD30-specific chimeric antigen receptor (CAR)-expressing cells.

12 Claims, 5 Drawing Sheets

Specification includes a Sequence Listing.

FIG. 3

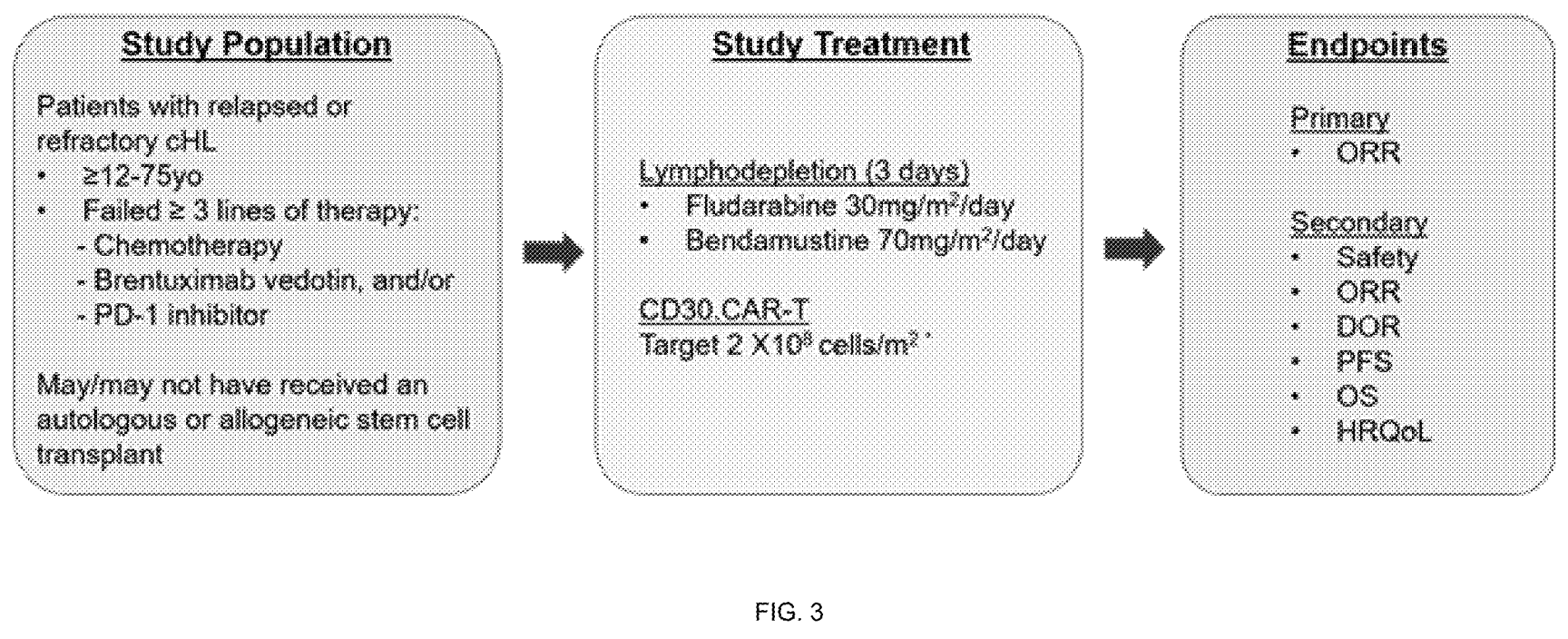

Study Population

Patients with relapsed or refractory cHL
- ≥12-75yo
- Failed ≥ 3 lines of therapy:
  - Chemotherapy
  - Brentuximab vedotin, and/or
  - PD-1 inhibitor May/may not have received an autologous or allogeneic stem cell transplant

Study Treatment

Lymphodepletion (3 days)
- Fludarabine 30mg/m²/day
- Bendamustine 70mg/m²/day

CD30 CAR-T
Target 2 X10⁸ cells/m²

Endpoints

Primary
- ORR

Secondary
- Safety
- ORR
- DOR
- PFS
- OS
- HRQoL

Study Population

Adult Patients with relapsed or refractory, CD30-positive NHL

- ALCL
- PTCL-NOS
- ENKTCL, nasal type
- DLBCL-NOS
- PMBCL

Study Treatment (n=12-21†)

Lymphodepletion (3 days)

- Fludarabine 30mg/m²/day
- Bendamustine 70 mg/m²/day

Autologous CD30.CAR-T§

- DL1*: 2 x10⁸ cells/m²
- DL2: 4 x10⁸ cells/m²
- DL3: 6 x10⁸ cells/m²

Endpoints

Primary

- Safety
- RP2D

Secondary

- ORR
- PK (CD30.CAR-T cells)
- DOR
- PFS
- OS

TREATMENT OF CD30-POSITIVE CANCER

This Application is a national stage filing under 35 U.S.C. § 371 of International PCT Application Serial No. PCT/EP2021/065037, filed Jun. 4, 2021, entitled "TREATMENT OF CD30-POSITIVE CANCER," which claims priority under 35 U.S.C. § 119 (e) to U.S. Application Ser. No. 63/035,104, filed Jun. 5, 2020, entitled "TREATMENT OF CD30-POSITIVE CANCER", the contents and elements of which are herein incorporated by reference for all purposes in their entireties.

This invention was made with government support under HL114564 awarded by National Institutes of Health. The government has certain rights in the invention.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Dec. 1, 2022, is named T082470018US01-SEQ-AZW and is 47,547 bytes in size.

TECHNICAL FIELD

The present invention relates to methods of medical treatment and prophylaxis.

BACKGROUND

CD30.CAR-T therapy is comprised of T-cells genetically modified to express a chimeric antigen receptor (CAR) specific for CD30, to target and kill cancer cells expressing the CD30 transmembrane glycoprotein. The drug product is generated from peripheral blood mononuclear cells (PBMCs) taken from patients with CD30-positive lymphoma.

In an initial Phase 1 study in patients with CD30-positive hematologic malignancies including classical Hodgkin Lymphoma (cHL), CD30.CAR-T administration was shown to be safe but only a minority of patients had durable responses (NCT01316146; Ramos et al., J Clin Invest. (2017) 127(9):3462-3471).

CD30.CAR-T therapy has been shown to be well-tolerated, with significant clinical activity demonstrated in heavily pre-treated patients with CD30-positive, relapsed or refractory classical HL and some NHL patients, following lymphodepletion chemotherapy (NCT02917083 (RELY-30); Ramos et al., Biol Blood Marrow Transplant 25 (2019) S7-S75, Abstract 79).

SUMMARY

In a first aspect, the present disclosure provides a method of treating a CD30-positive cancer in a subject, comprising:
(i) administering a lymphodepleting chemotherapy to the subject, and
(ii) subsequently administering CD30-specific chimeric antigen receptor (CAR)-expressing T cells to the subject.

The present disclosure also provides a population of CD30-specific chimeric antigen receptor (CAR)-expressing T cells for use in a method of treating a CD30-positive cancer, wherein the method comprises:
(i) administering a lymphodepleting chemotherapy to the subject, and (ii) subsequently administering CD30-specific CAR-T cells to the subject.

The present disclosure also provides the use of a population of CD30-specific chimeric antigen receptor (CAR)-expressing T cells in the manufacture of a medicament for use in a method of treating a CD30-positive cancer, wherein the method comprises:
(i) administering a lymphodepleting chemotherapy to the subject, and
(ii) subsequently administering CD30-specific CAR-T cells to the subject.

In some embodiments, administering a lymphodepleting chemotherapy to the subject comprises administering fludarabine and bendamustine.

In some embodiments, the method comprises administering fludarabine at a dose of 15 to 60 mg/m² per day, for 2 to 6 consecutive days.

In some embodiments, the method comprises administering fludarabine at a dose of 30 mg/m² per day, for 3 consecutive days.

In some embodiments, the method comprises administering bendamustine at a dose of 35 to 140 mg/m² per day, for 2 to 6 consecutive days.

In some embodiments, the method comprises administering bendamustine at a dose of 70 mg/m² per day, for 3 consecutive days.

In some embodiments, the method comprises administering $5 \times 10^7$ CD30-specific CAR-expressing T cells/m² to $1 \times 10^9$ CD30-specific CAR-expressing T cells/m² to the subject.

In some embodiments, the method comprises administering $1 \times 10^8$ CD30-specific CAR-expressing T cells/m² to $6 \times 10^8$ CD30-specific CAR-expressing T cells/m² to the subject.

In some embodiments, the method comprises:
(i) administering fludarabine at a dose of 30 mg/m² per day and bendamustine at a dose of 70 mg/m² per day to a subject for 3 consecutive days, and
(ii) subsequently administering CD30-specific CAR-expressing T cells to the subject at a dose of $2 \times 10^8$ CD30-specific CAR-expressing T cells/m² to $6 \times 10^8$ CD30-specific CAR-expressing T cells/m².

In some embodiments, the CD30-positive cancer is selected from: a hematological cancer, a solid cancer, a hematopoietic malignancy, Hodgkin's lymphoma, anaplastic large cell lymphoma, peripheral T cell lymphoma, peripheral T cell lymphoma not otherwise specified, T cell leukemia, T cell lymphoma, cutaneous T cell lymphoma, NK-T cell lymphoma, extranodal NK-T cell lymphoma, non-Hodgkin's lymphoma, B cell non-Hodgkin's lymphoma, diffuse large B cell lymphoma, diffuse large B cell lymphoma not otherwise specified, EBV-positive B cell lymphoma, EBV-positive diffuse large B cell lymphoma, primary mediastinal B cell lymphoma, advanced systemic mastocytosis, a germ cell tumor and testicular embryonal carcinoma.

In some embodiments, the CD30-positive cancer is selected from: Hodgkin's lymphoma, non-Hodgkin's lymphoma, anaplastic large cell lymphoma, peripheral T cell lymphoma not otherwise specified, extranodal NK-T cell lymphoma, diffuse large B cell lymphoma not otherwise specified and primary mediastinal large B-cell lymphoma.

In some embodiments, the subject has previously failed therapy for the CD30-positive cancer.

In some embodiments, the CD30-positive cancer is a relapsed or refractory CD30-positive cancer.

In some embodiments, the CD30-specific CAR-expressing T cells comprise a CAR comprising: (i) an antigen-binding domain which binds specifically to CD30, (ii) a transmembrane domain, and (iii) a signalling domain, wherein the signalling domain comprises: (a) an amino acid sequence derived from the intracellular domain of CD28, and (b) an amino acid sequence comprising an immunoreceptor tyrosine-based activation motif (ITAM).

In some embodiments, the signalling domain comprises an amino acid sequence having at least 80% amino acid sequence identity to SEQ ID NO:26.

In some embodiments, the transmembrane domain is derived from the transmembrane domain of CD28.

In some embodiments, the transmembrane domain comprises an amino acid sequence having at least 80% amino acid sequence identity to SEQ ID NO:20.

In some embodiments, the antigen-binding domain comprises an amino acid sequence having at least 80% amino acid sequence identity to SEQ ID NO:14, and an amino acid sequence having at least 80% amino acid sequence identity to SEQ ID NO:15.

In some embodiments, the antigen-binding domain comprises an amino acid sequence having at least 80% amino acid sequence identity to SEQ ID NO:18.

In some embodiments, the signalling domain comprises: (a) an amino acid sequence derived from the intracellular domain of CD3.

In some embodiments, the signalling domain comprises an amino acid sequence having at least 80% amino acid sequence identity to SEQ ID NO:25.

In some embodiments, the CAR additionally comprises a hinge region provided between the antigen-binding domain and the transmembrane domain.

In some embodiments, the hinge region comprises an amino acid sequence having at least 80% amino acid sequence identity to SEQ ID NO:33.

In some embodiments, the CAR comprises an amino acid sequence having at least 80% amino acid sequence identity to SEQ ID NO:35 or 36.

DESCRIPTION

CD30-Positive Cancer

The present disclosure relates to the treatment of cancer, more particularly CD30-positive cancer.

CD30 (also known as TNFRSF8) is the protein identified by UniProt: P28908. CD30 is a single pass, type I transmembrane glycoprotein of the tumor necrosis factor receptor superfamily. CD30 structure and function is described e.g. in van der Weyden et al., Blood Cancer Journal (2017) 7: e603 and Muta and Podack Immunol. Res. (2013) 57(1-3):151-8, both of which are hereby incorporated by reference in their entirety.

Alternative splicing of mRNA encoded by the human TNFRSF8 gene yields three isoforms: isoform 1 ('long' isoform; UniProt: P28908-1, v1; SEQ ID NO:1), isoform 2 ('cytoplasmic', 'short' or 'C30V' isoform, UniProt: P28908-2; SEQ ID NO:2) in which the amino acid sequence corresponding to positions 1 to 463 of SEQ ID NO:1 are missing, and isoform 3 (UniProt: P28908-3; SEQ ID NO:3) in which the amino acid sequence corresponding to positions 1 to 111 and position 446 of SEQ ID NO:1 are missing. The N-terminal 18 amino acids of SEQ ID NO:1 form a signal peptide (SEQ ID NO:4), which is followed by a 367 amino acid extracellular domain (positions 19 to 385 of SEQ ID NO:1, shown in SEQ ID NO:5), a 21 amino acid transmembrane domain (positions 386 to 406 of SEQ ID NO:1, shown in SEQ ID NO:6), and a 189 amino acid cytoplasmic domain (positions 407 to 595 of SEQ ID NO:1, shown in SEQ ID NO:7).

In this specification "CD30" refers to CD30 from any species and includes CD30 isoforms, fragments, variants or homologues from any species. As used herein, a "fragment", "variant" or "homologue" of a reference protein may optionally be characterised as having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of the reference protein (e.g. a reference isoform). In some embodiments fragments, variants, isoforms and homologues of a reference protein may be characterised by ability to perform a function performed by the reference protein.

In some embodiments, the CD30 from a mammal (e.g. a primate (rhesus, cynomolgous, or human) and/or a rodent (e.g. rat or murine) CD30). In preferred embodiments the CD30 is a human CD30. Isoforms, fragments, variants or homologues may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of an immature or mature CD30 isoform from a given species, e.g. human. A fragment of CD30 may have a minimum length of one of 10, 20, 30, 40, 50, 100, 200, 300, 400, 500 or 590 amino acids, and may have a maximum length of one of 10, 20, 30, 40, 50, 100, 200, 300, 400, 500 or 595 amino acids.

In some embodiments, the CD30 comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:1, 2 or 3.

In some embodiments, the CD30 comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:5.

In some embodiments, a fragment of CD30 comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:5 or 19.

The present disclosure relates to the treatment of CD30-associated cancer.

As used herein, "cancer" may refer to any unwanted cell proliferation (or any disease manifesting itself by unwanted cell proliferation), neoplasm or tumor. The cancer may be benign or malignant and may be primary or secondary (metastatic). A neoplasm or tumor may be any abnormal growth or proliferation of cells and may be located in any tissue. The cancer may be of tissues/cells derived from e.g. the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentum, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, and/or white blood cells.

In some embodiments the cancer is a cancer in which CD30 is pathologically implicated. That is, in some embodiments the cancer is a cancer which is caused or exacerbated by CD30 expression, a cancer for which expression of CD30 is a risk factor and/or a cancer for which expression of CD30 is positively associated with onset, development, progression, severity or metastasis of the cancer. The cancer may be characterised by CD30 expression, e.g. the cancer may comprise cells expressing CD30. Such cancers may be referred to as CD30-positive cancers.

A CD30-positive cancer may be a cancer comprising cells expressing CD30 (e.g. cells expressing CD30 protein at the cell surface). A CD30-positive cancer may overexpress CD30. Overexpression of CD30 can be determined by detection of a level of gene or protein expression of CD30 which is greater than the level of expression by equivalent non-cancerous cells/non-tumor tissue. A given cancer/sample may be evaluated for gene/protein expression of CD30 by techniques well known to the skilled person, e.g. by qRT-PCR (for gene expression), antibody-based assays (e.g. western blot, flow cytometry, etc. for protein expression).

CD30-positive cancers are described e.g. in van der Weyden et al., Blood Cancer Journal (2017) 7:e603 and Muta and Podack, Immunol Res (2013), 57(1-3):151-8, both of which are hereby incorporated by reference in their entirety. CD30 is expressed on small subsets of activated T and B lymphocytes, and by various lymphoid neoplasms including classical Hodgkin's lymphoma and anaplastic large cell lymphoma. Variable expression of CD30 has also been shown for peripheral T cell lymphoma, not otherwise specified (PTCL-NOS), adult T cell leukemia/lymphoma, cutaneous T cell lymphoma (CTCL), extra-nodal NK-T cell lymphoma, various B cell non-Hodgkin's lymphomas (including diffuse large B cell lymphoma, particularly EBV-positive diffuse large B cell lymphoma), and advanced systemic mastocytosis. CD30 expression has also been observed in some non-hematopoietic malignancies, including germ cell tumors and testicular embryonal carcinomas.

The transmembrane glycoprotein CD30, is a member of the tumor necrosis factor receptor superfamily (Falini et al., Blood (1995) 85(1):1-14). Members of the TNF/TNF-receptor (TNF-R) superfamily coordinate the immune response at multiple levels and CD30 plays a role in regulating the function or proliferation of normal lymphoid cells. CD30 was originally described as an antigen recognized by a monoclonal antibody, Ki-1, which was raised by immunizing mice with a HL-derived cell line, L428 (Muta and Podack, Immunol Res (2013) 57: 151-158). CD30 antigen expression has been used to identify ALCL and Reed-Sternberg cells in Hodgkin's disease (Falini et al., Blood (1995) 85(1):1-14). With the wide expression in the lymphoma malignant cells, CD30 is therefore a potential target for developing both antibody-based immunotherapy and cellular therapies. Importantly, CD30 is not typically expressed on normal tissues under physiologic conditions, thus is notably absent on resting mature or precursor B or T cells (Younes and Ansell, Semin Hematol (2016) 53: 186-189). Brentuximab vedotin, an antibody-drug conjugate that targets CD30 was initially approved for the treatment of CD30-positive HL (Adcetris® US Package Insert 2018). Data from brentuximab vedotin trials support CD30 as a therapeutic target for the treatment of CD30-positive lymphoma, although toxicities associated with its use are of concern.

Hodgkin lymphoma (HL) is an uncommon malignancy involving lymph nodes and the lymphatic system. The incidence of HL is bimodal with most patients diagnosed between 15 and 30 years of age, followed by another peak in adults aged 55 years or older. In 2019 it is estimated there will be 8,110 new cases (3,540 in females and 4570 in males) in the United States and 1,000 deaths (410 female and 590 males) from this disease (American Cancer Society 2019). Based on 2012-2016 cases in National Cancer Institute's SEER database, the incidence rate for HL for the pediatric HL patients in US is as follows: Age 1-4: 0.1; Age 5-9: 0.3; Age 10-14: 1.3; Age 15-19: 3.3 per 100,000 (SEER Cancer Statistics Review, 1975-2016]).

The World Health Organization (WHO) classification divides HL into 2 main types: classical Hodgkin lymphoma (cHL) and nodular lymphocyte-predominant Hodgkin lymphoma (NLPHL). In Western countries, cHL accounts for 95% and NLPHL accounts for 5% of all HL (National Comprehensive Cancer Network Guidelines 2019).

First-line chemotherapy for cHL patients with advanced disease is associated with cure rates between 70% and 75% (Karantanos et al., Blood Lymphat Cancer (2017) 7:37-52). Salvage chemotherapy followed by Autologous Stem Cell Transplant (ASCT) is commonly used in patients who relapse after primary therapy. Unfortunately, up to 50% of the cHL patients experience disease recurrence after ASCT. The median overall survival of patients who relapse after ASCT is approximately two years (Alinari Blood (2016) 127:287-295). Despite aggressive combination chemotherapy, between 10% and 40% of patients do not achieve a response to salvage chemotherapy and there are no randomized clinical trial data supporting ASCT in non-responders. For patients who do not respond to salvage chemotherapy, relapse after ASCT or who are not candidates for this approach, the prognosis continues to be grave and new treatment approaches are urgently needed (Keudell British Journal of Haematology (2019) 184:105-112).

While a majority of the pediatric population (children, adolescents, and young adults) will be cured with currently available therapy, a small fraction of patients may have refractory or relapsed disease and require novel therapies that have an acceptable safety profile with improved efficacy benefit (Flerlage et al., Blood (2018) 132: 376-384; Kelly, Blood (2015) 126: 2452-2458; McClain and Kamdar, in UpToDate 2019; Moskowitz, ASCO Educational Book (2019) 477-486). HL patients treated with high dose chemotherapy during childhood commonly experience treatment-related long-term sequelae, such as cardiac, pulmonary, gonadal, and endocrine toxicity as well as second malignant neoplasms (Castellino et al., Blood (2011) 117(6): 1806-1816).

In some embodiments, a CD30-positive cancer according to the present disclosure may be selected from: a hematological cancer, a solid cancer, a hematopoietic malignancy, Hodgkin's lymphoma, anaplastic large cell lymphoma, peripheral T cell lymphoma, peripheral T cell lymphoma not otherwise specified, T cell leukemia, T cell lymphoma, cutaneous T cell lymphoma, NK-T cell lymphoma, extranodal NK-T cell lymphoma, non-Hodgkin's lymphoma, B cell non-Hodgkin's lymphoma, diffuse large B cell lymphoma, diffuse large B cell lymphoma not otherwise specified, EBV-positive B cell lymphoma, EBV-positive diffuse large B cell lymphoma, primary mediastinal B cell lymphoma, advanced systemic mastocytosis, a germ cell tumor and testicular embryonal carcinoma.

The CD30-positive cancer may be a relapsed CD30-positive cancer. As used herein, a "relapsed" cancer refers to a cancer which responded to a treatment (e.g. a first line therapy for the cancer), but which has subsequently re-emerged/progressed, e.g. after a period of remission. For example, a relapsed cancer may be a cancer whose growth/ progression was inhibited by a treatment (e.g. a first line therapy for the cancer), and which has subsequently grown/progressed.

The CD30-positive cancer may be a refractory CD30-positive cancer. As used herein, a "refractory" cancer refers to a cancer which has not responded to a treatment (e.g. a first line therapy for the cancer). For example, a refractory cancer may be a cancer whose growth/progression was not inhibited by a treatment (e.g. a first line therapy for the cancer). In some embodiments a refractory cancer may be a cancer for which a subject receiving treatment for the cancer did not display a partial or complete response to the treatment.

In embodiments where the CD30-positive cancer is anaplastic large cell lymphoma, the cancer may be relapsed or refractory with respect to treatment with chemotherapy, brentuximab vedotin, or crizotinib.

In embodiments where the CD30-positive cancer is peripheral T cell lymphoma not otherwise specified, the cancer may be relapsed or refractory with respect to treatment with chemotherapy or brentuximab vedotin.

In embodiments where the CD30-positive cancer is extranodal NK-T cell lymphoma, the cancer may be relapsed or refractory with respect to treatment with chemotherapy (with or without asparaginase) or brentuximab vedotin.

In embodiments where the CD30-positive cancer is diffuse large B cell lymphoma not otherwise specified, the cancer may be relapsed or refractory with respect to treatment with chemotherapy (with or without rituximab) or CD19 CAR-T therapy.

In embodiments where the CD30-positive cancer is primary mediastinal B cell lymphoma, the cancer may be relapsed or refractory with respect to treatment with chemotherapy, immune checkpoint inhibitor (e.g. PD-1 inhibitor) or CD19 CAR-T therapy.

CD30-Specific CARs

CARs

The present disclosure relates to immune cells comprising/expressing CD30-specific chimeric antigen receptors (CARs).

Chimeric Antigen Receptors (CARs) are recombinant receptor molecules which provide both antigen-binding and T cell activating functions. CAR structure and engineering is reviewed, for example, in Dotti et al., Immunol Rev (2014) 257(1), which is hereby incorporated by reference in its entirety.

CARs comprise an antigen-binding domain linked via a transmembrane domain to a signalling domain. An optional hinge or spacer domain may provide separation between the antigen-binding domain and transmembrane domain, and may act as a flexible linker. When expressed by a cell, the antigen-binding domain is provided in the extracellular space, and the signalling domain is intracellular.

The antigen-binding domain mediates binding to the target antigen for which the CAR is specific. The antigen-binding domain of a CAR may be based on the antigen-binding region of an antibody which is specific for the antigen to which the CAR is targeted. For example, the antigen-binding domain of a CAR may comprise amino acid sequences for the complementarity-determining regions (CDRs) of an antibody which binds specifically to the target antigen. The antigen-binding domain of a CAR may comprise or consist of the light chain and heavy chain variable region amino acid sequences of an antibody which binds specifically to the target antigen. The antigen-binding domain may be provided as a single chain variable fragment (scFv) comprising the sequences of the light chain and heavy chain variable region amino acid sequences of an antibody. Antigen-binding domains of CARs may target antigen based on other protein:protein interaction, such as ligand:receptor binding; for example an IL-13Rα2-targeted CAR has been developed using an antigen-binding domain based on IL-13 (see e.g. Kahlon et al. 2004 Cancer Res 64(24): 9160-9166).

The transmembrane domain is provided between the antigen-binding domain and the signalling domain of the CAR. The transmembrane domain provides for anchoring the CAR to the cell membrane of a cell expressing a CAR, with the antigen-binding domain in the extracellular space, and signalling domain inside the cell. Transmembrane domains of CARs may be derived from transmembrane region sequences for cell membrane-bound proteins (e.g. CD28, CD8, etc.).

Throughout this specification, polypeptides, domains and amino acid sequences which are 'derived from' a reference polypeptide/domain/amino acid sequence have at least 60%, preferably one of 70%, 75%, 80%, 85%, 90%, 91%, 92%, 93%, 94%, 95%, 96%, 97%, 98%, 99% or 100% amino acid sequence identity to the amino acid sequence of the reference polypeptide/domain/amino acid sequence. Polypeptides, domains and amino acid sequences which are 'derived from' a reference polypeptide/domain/amino acid sequence preferably retains the functional and/or structural properties of the reference polypeptide/domain/amino acid sequence.

By way of illustration, an amino acid sequence derived from the intracellular domain of CD28 may comprise an amino acid sequence having 60%, preferably one of 70%, 75%, 80%, 85%, 90%, 91%, 92%, 93%, 94%, 95%, 96%, 97%, 98%, 99% or 100% amino acid sequence identity to the intracellular domain of CD28, e.g. as shown in SEQ ID NO:26. Furthermore, an amino acid sequence derived from the intracellular domain of CD28 preferably retains the functional properties of the amino acid sequence of SEQ ID NO:26, i.e. the ability activate CD28-mediated signalling.

The amino acid sequence of a given polypeptide or domain thereof can be retrieved from, or determined from a nucleic acid sequence retrieved from, databases known to the person skilled in the art. Such databases include Gen-Bank, EMBL and UniProt.

The signalling domain comprises amino acid sequences required activation of immune cell function. The CAR signalling domains may comprise the amino acid sequence of the intracellular domain of CD3-ζ, which provides immunoreceptor tyrosine-based activation motifs (ITAMs) for phosphorylation and activation of the CAR-expressing cell. Signalling domains comprising sequences of other ITAM-containing proteins have also been employed in CARs, such as domains comprising the ITAM containing region of FcγRI (Haynes et al., 2001 J Immunol 166(1):182-187). CARs comprising a signalling domain derived from the intracellular domain of CD3-ζ are often referred to as first generation CARs.

The signalling domains of CARs typically also comprise the signalling domain of a costimulatory protein (e.g. CD28, 4-1 BB etc.), for providing the costimulation signal necessary for enhancing immune cell activation and effector function. CARs having a signalling domain including additional co-stimulatory sequences are often referred to as second generation CARs. In some cases CARs are engineered to provide for co-stimulation of different intracellular signalling pathways. For example, CD28 costimulation preferentially activates the phosphatidylinositol 3-kinase (PI3K) pathway, whereas 4-1 BB costimulation triggers signalling is through TNF receptor associated factor (TRAF) adaptor proteins. Signalling domains of CARs therefore sometimes contain co-stimulatory sequences derived from signalling domains of more than one co-stimulatory molecule. CARs comprising a signalling domain with multiple co-stimulatory sequences are often referred to as third generation CARs.

An optional hinge or spacer region may provide separation between the antigen-binding domain and the transmembrane domain, and may act as a flexible linker. Such regions may be or comprise flexible domains allowing the binding moiety to orient in different directions, which may e.g. be derived from the CH1-CH2 hinge region of IgG.

Through engineering to express a CAR specific for a particular target antigen, immune cells (typically T cells, but also other immune cells such as NK cells) can be directed to kill cells expressing the target antigen. Binding of a CAR-expressing T cell (CAR-T cell) to the target antigen for which it is specific triggers intracellular signalling, and consequently activation of the T cell. The activated CAR-T cell is stimulated to divide and produce factors resulting in killing of the cell expressing the target antigen.

CD30-Specific CARs

Since cHL is apparently sensitive to the cellular immune response (graft versus lymphoma effect) and antibody treatment, there is interest in combining both approaches through the generation of artificial chimeric antigen receptors (CARs).

CAR-targeting CD30 in preclinical studies have shown that T-lymphocytes engineered to express this receptor are redirected to kill CD30-positive HL cell lines (Hombach et al. Cancer Res. (1998) 58(6):1116-9, Savoldo et al. Blood (2007) 110(7):2620-30). Further to this, in vitro and in vivo experiments to examine potential on-target toxicity, showed that anti-CD30 CAR-T cells demonstrated specific cytotoxicity against CD30-positive lymphoma cells while sparing CD30-positive activated HSPCs and B lymphocytes (Hombach et al., Mol Ther (2016) 24: 1423-1434).

An in vitro assessment of CD30.CAR T Cells that were manufactured as part of an ongoing clinical study was conducted (NCT01316146; Ramos et al., J Clin Invest. (2017) 127(9):3462-3471). The starting material for the engineered T cells was peripheral blood mononuclear cells from lymphoma patients. The manufactured CD30.CAR T cells in this published study were transduced with the same retroviral vector as the final drug product for the proposed clinical trial. A total of 22 lots of CD30.CAR T Cells were manufactured using either IL-2 (11 products) or IL-7/IL-15 (11 products).

By day 15 of culture, CD30.CAR T Cells grown in IL-7/IL-15 had greater expansion from baseline and higher final cell numbers (45±13 and 1.2×109±5.5×108, respectively) than those expanded in IL-2 (27.4±13 and 6.5× 108±3.3×108, respectively). CAR expression was comparable in both groups (>89%).

Specific in vitro cytotoxicity of the CD30.CAR T Cells was demonstrated in a 4-hour 51Cr release assay, using effector to target ratios of 40:1, 20:1, 10:1, and 5:1. The HDLM-2 cell line was used as a CD30-positive target cell while CD30-negative Raji tumor cells were used as a control (Ctr-Ts). A total of n=9 lots of cells cultured in IL-2 were tested, while a total of n=8 lots of cells expanded in IL-7/IL-15 were tested. FIG. 2D of Ramos et al., J Clin Invest. (2017) 127(9):3462-3471 shows mean specific lysis, provides evidence of the proposed mechanism of action of CD30.CAR-T, as shown by direct, specific, cellular cytotoxicity against CD30-positive tumor cells.

Antigen-Binding Domain

An "antigen-binding domain" refers to a domain which is capable of binding to a target antigen. The target antigen of the CARs of the present disclosure is CD30, or fragment thereof. Antigen-binding domains according to the present disclosure may be derived from an antibody/antibody fragment (e.g. Fv, scFv, Fab, single chain Fab (scFab), single domain antibodies (e.g. VhH), etc.) directed against CD30, or another CD30-binding molecule (e.g. a target antigen-binding peptide or nucleic acid aptamer, ligand or other molecule).

In some embodiments, the antigen-binding domain comprises an antibody heavy chain variable region (VH) and an antibody light chain variable region (VL) of an antibody capable of specific binding to the CD30. In some embodiments, the domain capable of binding to a target antigen comprises or consists of a CD30-binding peptide/polypeptide, e.g. a peptide aptamer, thioredoxin, monobody, anticalin, Kunitz domain, avimer, knottin, fynomer, atrimer, DARPin, affibody, nanobody (i.e. a single-domain antibody (sdAb)) affilin, armadillo repeat protein (ArmRP), OBody or fibronectin—reviewed e.g. in Reverdatto et al., Curr Top Med Chem. 2015; 15(12): 1082-1101, which is hereby incorporated by reference in its entirety (see also e.g. Boersma et al., J Biol Chem (2011) 286:41273-85 and Emanuel et al., Mabs (2011) 3:38-48).

The antigen-binding domains of the present disclosure may be derived from the VH and a VL of an antibody capable of specific binding to CD30. Antibodies generally comprise six complementarity-determining regions CDRs; three in the heavy chain variable region (VH): HC-CDR1, HC-CDR2 and HC-CDR3, and three in the light chain variable region (VL): LC-CDR1, LC-CDR2, and LC-CDR3. The six CDRs together define the paratope of the antibody, which is the part of the antibody which binds to the target antigen. The VH region and VL region comprise framework regions (FRs) either side of each CDR, which provide a scaffold for the CDRs. From N-terminus to C-terminus, VHs comprise the following structure: N term-[HC-FR1]-[HC-CDR1]-[HC-FR2]-[HC-CDR2]-[HC-FR3]-[HC-CDR3]-[HC-FR4]-C term; and VLs comprise the following structure: N term-[LC-FR1]-[LC-CDR1]-[LC-FR2]-[LC-CDR2]-[LC-FR3]-[LC-CDR3]-[LC-FR4]-C term.

VH and VL sequences may be provided in any suitable format provided that the antigen-binding domain can be linked to the other domains of the CAR. Formats contemplated in connection with the antigen-binding domain of the present disclosure include those described in Carter, Nat. Rev. Immunol 2006, 6: 343-357, such as scFv, dsFV, $(scFv)_2$ diabody, triabody, tetrabody, Fab, minibody, and $F(ab)_2$ formats.

In some embodiments, the antigen-binding domain comprises the CDRs of an antibody/antibody fragment which is capable of binding to CD30. In some embodiments, the antigen-binding domain comprises the VH region and the VL region of an antibody/antibody fragment which is capable of binding to CD30. A moiety comprised of the VH and a VL of an antibody may also be referred to herein as a variable fragment (Fv). The VH and VL may be provided on the same polypeptide chain, and joined via a linker sequence; such moieties are referred to as single-chain variable fragments (scFvs). Suitable linker sequences for the preparation of scFv are known to the skilled person, and may comprise serine and glycine residues.

In some embodiments, the antigen-binding domain comprises, or consists of, Fv capable of binding to CD30. In some embodiments, the antigen-binding domain comprises, or consists of, a scFv capable of binding to CD30.

The CD30-binding domain of the CAR of the present disclosure preferably displays specific binding to CD30 or a fragment thereof. The CD30-binding domain of the CAR of the present disclosure preferably displays specific binding to the extracellular domain of CD30. The CD30-binding domain may be derived from an anti-CD30 antibody or other CD30-binding agent, e.g. a CD30-binding peptide or CD30-binding small molecule.

The CD30-binding domain may be derived from the antigen-binding moiety of an anti-CD30 antibody.

Anti-CD30 antibodies include HRS3 and HRS4 (described e.g. in Hombach et al., Scand J Immunol (1998) 48(5):497-501), HRS3 derivatives described in Schlapschy et al., Protein Engineering, Design and Selection (2004) 17(12): 847-860, BerH2 (MBL International Cat #K0145-3, RRID:AB_590975), SGN-30 (also known as cAC10, described e.g. in Forero-Torres et al., Br J Haematol (2009) 146:171-9), MDX-060 (described e.g. in Ansell et al., J Clin Oncol (2007) 25:2764-9; also known as 5F11, iratumumab), and MDX-1401 (described e.g. in Cardarelli et al., Clin Cancer Res. (2009) 15(10):3376-83), and anti-CD30 antibodies described in WO 2020/068764 A1, WO 2003/059282 A2, WO 2006/089232 A2, WO 2007/084672 A2, WO 2007/044616 A2, WO 2005/001038 A2, US 2007/166309 A1, US 2007/258987 A1, WO 2004/010957 A2 and US 2005/009769 A1.

In some embodiments a CD30-binding domain according to the present disclosure comprises the CDRs of an anti-CD30 antibody. In some embodiments a CD30-binding domain according to the present disclosure comprises the VH and VL regions of an anti-CD30 antibody. In some embodiments a CD30-binding domain according to the present disclosure comprises an scFv comprising the VH and VL regions of an anti-CD30 antibody.

There are several different conventions for defining antibody CDRs and FRs, such as those described in Kabat et al., Sequences of Proteins of Immunological Interest, 5th Ed. Public Health Service, National Institutes of Health, Bethesda, MD (1991), Chothia et al., *J. Mol. Biol.* 196:901-917 (1987), and VBASE2, as described in Retter et al., *Nucl. Acids Res.* (2005) 33 (suppl 1): D671-D674. The CDRs and FRs of the VH regions and VL regions of the antibodies described herein are defined according to VBASE2.

In some embodiments the antigen-binding domain of the present disclosure comprises:

a VH incorporating the following CDRs:

HC-CDR1 having the amino acid sequence of SEQ ID NO:8

HC-CDR2 having the amino acid sequence of SEQ ID NO:9

HC-CDR3 having the amino acid sequence of SEQ ID NO:10, or a variant thereof in which one or two or three amino acids in one or more of HC-CDR1, HC-CDR2, or HC-CDR3 are substituted with another amino acid;

and a VL incorporating the following CDRs:

LC-CDR1 having the amino acid sequence of SEQ ID NO:11

LC-CDR2 having the amino acid sequence of SEQ ID NO:12

LC-CDR3 having the amino acid sequence of SEQ ID NO:13, or a variant thereof in which one or two or three amino acids in one or more of LC-CDR1, LC-CDR2, or LC-CDR3 are substituted with another amino acid.

In some embodiments the antigen-binding domain comprises:

a VH comprising, or consisting of, an amino acid sequence having at least 80% sequence identity (e.g. at least 85%, 86%, 87%, 88%, 89%, 90%, 91%, 92%, 93%, 94%, 95%, 96%, 97%, 98%, 99% or 100%) to the amino acid sequence of SEQ ID NO:14;

and a VL comprising, or consisting of, an amino acid sequence having at least 80% sequence identity (e.g. at least 85%, 86%, 87%, 88%, 89%, 90%, 91%, 92%, 93%, 94%, 95%, 96%, 97%, 98%, 99% or 100%) to the amino acid sequence of SEQ ID NO:15.

In some embodiments, a CD30-binding domain may comprise or consist of a single chain variable fragment (scFv) comprising a VH sequence and a VL sequence as described herein. The VH sequence and VL sequence may be covalently linked. In some embodiments, the VH and the VL sequences are linked by a flexible linker sequence, e.g. a flexible linker sequence as described herein. The flexible linker sequence may be joined to ends of the VH sequence and VL sequence, thereby linking the VH and VL sequences. In some embodiments the VH and VL are joined via a linker sequence comprising, or consisting of, the amino acid sequence of SEQ ID NO:16 or 17.

In some embodiments, the CD30-binding domain comprises, or consists of, an amino acid sequence having at least 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:18.

In some embodiments the CD30-binding domain is capable of binding to CD30, e.g. in the extracellular domain of CD30. In some embodiments, the CD30-binding domain is capable of binding to the epitope of CD30 which is bound by antibody HRS3, e.g. within the region of amino acid positions 185-335 of human CD30 numbered according to SEQ ID NO:1, shown in SEQ ID NO:19 (Schlapschy et al., Protein Engineering, Design and Selection (2004) 17(12): 847-860, hereby incorporated by reference in its entirety).

In some embodiments, a CD30-binding domain may comprise or consist of a single chain variable fragment (scFv) comprising a VH sequence and a VL sequence as described herein. The VH sequence and VL sequence may be covalently linked. In some embodiments, the VH and the VL sequences are linked by a flexible linker sequence, e.g. a flexible linker sequence as described herein. The flexible linker sequence may be joined to ends of the VH sequence and VL sequence, thereby linking the VH and VL sequences. In some embodiments the VH and VL are joined via a linker sequence comprising, or consisting of, the amino acid sequence of SEQ ID NO:16.

In some embodiments, the antigen-binding domain (and thus the CAR) is multispecific. By "multispecific" it is meant that the antigen-binding domain displays specific binding to more than one target. In some embodiments the antigen-binding domain is a bispecific antigen-binding domain. In some embodiments the antigen-binding molecule comprises at least two different antigen-binding moieties (i.e. at least two antigen-binding moieties, e.g. comprising non-identical VHs and VLs). Individual antigen-binding moieties of multispecific antigen-binding domains may be connected, e.g. via linker sequences.

In some embodiments the antigen-binding domain binds to at least two, non-identical target antigens, and so is at least bispecific. The term "bispecific" means that the antigen-binding domain is able to bind specifically to at least two distinct antigenic determinants. In some embodiments, at least one of the target antigens for the multispecific antigen-binding domain/CAR is CD30.

It will be appreciated that an antigen-binding domain according to the present disclosure (e.g. a multispecific antigen-binding domain) comprises antigen-binding moieties capable of binding to the target(s) for which the antigen-binding domain is specific. For example, an antigen-binding domain which is capable of binding to CD30 and an antigen other than CD30 may comprise: (i) an antigen-binding moiety which is capable of binding to CD30, and (ii) an antigen-binding moiety which is capable of binding to a target antigen other than CD30.

A target antigen other than CD30 may be any target antigen. In some embodiments, the target antigen is an antigen whose expression/activity, or whose upregulated expression/activity, is positively associated with a disease or disorder (e.g. a cancer, an infectious disease or an autoimmune disease). The target antigen is preferably expressed at the cell surface of a cell expressing the target antigen. It will be appreciated that the CAR directs effect activity of the cell expressing the CAR against cells/tissues expressing the target antigen for which the CAR comprises a specific antigen-binding domain.

In some embodiments, a target antigen may be a cancer cell antigen. A cancer cell antigen is an antigen which is expressed or over-expressed by a cancer cell. A cancer cell antigen may be any peptide/polypeptide, glycoprotein, lipoprotein, glycan, glycolipid, lipid, or fragment thereof. A cancer cell antigen's expression may be associated with a cancer. A cancer cell antigen may be abnormally expressed by a cancer cell (e.g. the cancer cell antigen may be expressed with abnormal localisation), or may be expressed with an abnormal structure by a cancer cell. A cancer cell antigen may be capable of eliciting an immune response. In some embodiments, the antigen is expressed at the cell surface of the cancer cell (i.e. the cancer cell antigen is a cancer cell surface antigen). In some embodiments, the part of the antigen which is bound by the antigen-binding molecule described herein is displayed on the external surface of the cancer cell (i.e. is extracellular). The cancer cell antigen may be a cancer-associated antigen. In some embodiments the cancer cell antigen is an antigen whose expression is associated with the development, progression or severity of symptoms of a cancer. The cancer-associated antigen may be associated with the cause or pathology of the cancer, or may be expressed abnormally as a consequence of the cancer. In some embodiments, the cancer cell antigen is an antigen whose expression is upregulated (e.g. at the RNA and/or protein level) by cells of a cancer, e.g. as compared to the level of expression of by comparable non-cancerous cells (e.g. non-cancerous cells derived from the same tissue/cell type). In some embodiments, the cancer-associated antigen may be preferentially expressed by cancerous cells, and not expressed by comparable non-cancerous cells (e.g. non-cancerous cells derived from the same tissue/cell type). In some embodiments, the cancer-associated antigen may be the product of a mutated oncogene or mutated tumor suppressor gene. In some embodiments, the cancer-associated antigen may be the product of an overexpressed cellular protein, a cancer antigen produced by an oncogenic virus, an oncofetal antigen, or a cell surface glycolipid or glycoprotein.

Cancer cell antigens are reviewed by Zarour H M, DeLeo A, Finn O J, et al. Categories of Tumor Antigens. In: Kufe D W, Pollock R E, Weichselbaum R R, et al., editors. Holland-Frei Cancer Medicine. 6th edition. Hamilton (ON): BC Decker; 2003. Cancer cell antigens include oncofetal antigens: CEA, Immature laminin receptor, TAG-72; onco-viral antigens such as HPV E6 and E7; overexpressed proteins: BING-4, calcium-activated chloride channel 2, cyclin-B1, 9D7, Ep-CAM, EphA3, HER2/neu, telomerase, mesothelin, SAP-1, survivin; cancer-testis antigens: BAGE, CAGE, GAGE, MAGE, SAGE, XAGE, CT9, CT10, NY-ESO-1, PRAME, SSX-2; lineage restricted antigens: MART1, Gp100, tyrosinase, TRP-1/2, MC1R, prostate specific antigen; mutated antigens: β-catenin, BRCA1/2, CDK4, CML66, Fibronectin, MART-2, p53, Ras, TGF-βRII; post-translationally altered antigens: MUC1, idiotypic antigens: Ig, TCR. Other cancer cell antigens include heat-shock protein 70 (HSP70), heat-shock protein 90 (HSP90), glucose-regulated protein 78 (GRP78), vimentin, nucleolin, feto-acinar pancreatic protein (FAPP), alkaline phosphatase placental-like 2 (ALPPL-2), siglec-5, stress-induced phosphoprotein 1 (STIP1), protein tyrosine kinase 7 (PTK7), and cyclophilin B.

In some embodiments the cancer cell antigen is a cancer cell antigen described in Zhao and Cao, Front Immunol. 2019; 10: 2250, which is hereby incorporated by reference in its entirety. In some embodiments, a cancer cell antigen is selected from CD30, CD19, CD20, CD22, ROR1R, CD4, CD7, CD38, BCMA, Mesothelin, EGFR, GPC3, MUC1, HER2, GD2, CEA, EpCAM, LeY and PSCA.

In some embodiments, a cancer cell antigen is an antigen expressed by cells of a hematological malignancy. In some embodiments, a cancer cell antigen is selected from CD30, CD19, CD20, CD22, ROR1R, CD4, CD7, CD38 and BCMA.

In some embodiments, a cancer cell antigen is an antigen expressed by cells of a solid tumor. In some embodiments, a cancer cell antigen is selected from Mesothelin, EGFR, GPC3, MUC1, HER2, GD2, CEA, EpCAM, LeY and PSCA.

Transmembrane Domain

The CAR of the present disclosure comprises a transmembrane domain. A transmembrane domain refers to any three-dimensional structure formed by a sequence of amino acids which is thermodynamically stable in a biological membrane, e.g. a cell membrane. In connection with the present disclosure, the transmembrane domain may be an amino acid sequence which spans the cell membrane of a cell expressing the CAR.

The transmembrane domain may comprise or consist of a sequence of amino acids which forms a hydrophobic alpha helix or beta-barrel. The amino acid sequence of the transmembrane domain of the CAR of the present disclosure may be, or may be derived from, the amino acid sequence of a transmembrane domain of a protein comprising a transmembrane domain. Transmembrane domains are recorded in databases such as GenBank, UniProt, Swiss-Prot, TrEMBL, Protein Information Resource, Protein Data Bank, Ensembl, and InterPro, and/or can be identified/predicted e.g. using amino acid sequence analysis tools such as TMHMM (Krogh et al., 2001 J Mol Biol 305: 567-580).

In some embodiments, the amino acid sequence of the transmembrane domain of the CAR of the present disclosure may be, or may be derived from, the amino acid sequence of the transmembrane domain of a protein expressed at the cell surface. In some embodiments the protein expressed at the cell surface is a receptor or ligand, e.g. an immune receptor or ligand. In some embodiments the amino acid sequence of the transmembrane domain may be, or may be derived from, the amino acid sequence of the transmembrane domain of one of ICOS, ICOSL, CD86, CTLA-4, CD28, CD80, MHC class I α, MHC class II α, MHC class II β, CD3ε, CD3δ, CD3γ, CD3ζ, TCRα TCRβ, CD4, CD8α, CD8β, CD40, CD40L, PD-1, PD-L1, PD-L2, 4-1 BB, 4-1 BBL, OX40, OX40L, GITR, GITRL, TIM-3, Galectin 9, LAG3, CD27, CD70, LIGHT, HVEM, TIM-4, TIM-1, ICAM1, LFA-1, LFA-3, CD2, BTLA, CD160, LILRB4, LILRB2, VTCN1, CD2, CD48, 2B4, SLAM, CD30, CD30L, DR3, TL1A, CD226, CD155, CD112 and CD276. In some embodiments, the transmembrane is, or is derived from, the amino acid sequence of the transmembrane domain of CD28, CD3-ζ, CD8α, CD8β or CD4. In some embodiments, the transmembrane is, or is derived from, the amino acid sequence of the transmembrane domain of CD28.

In some embodiments, the transmembrane domain comprises, or consists of, an amino acid sequence having at least 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:20.

In some embodiments, the transmembrane domain comprises, or consists of, an amino acid sequence having at least 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:21.

In some embodiments, the transmembrane domain comprises, or consists of, an amino acid sequence having at least 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:22.

Signalling Domain

The chimeric antigen receptor of the present disclosure comprises a signalling domain. The signalling domain provides sequences for initiating intracellular signalling in cells expressing the CAR.

The signalling domain comprises ITAM-containing sequence. An ITAM-containing sequence comprises one or more immunoreceptor tyrosine-based activation motifs (ITAMs). ITAMs comprise the amino acid sequence YXXL/I (SEQ ID NO:23), wherein "X" denotes any amino acid. In ITAM-containing proteins, sequences according to SEQ ID NO:23 are often separated by 6 to 8 amino acids; YXXL/I(X)$_{6-8}$YXXL/I (SEQ ID NO:24). When phosphate groups are added to the tyrosine residue of an ITAM by tyrosine kinases, a signalling cascade is initiated within the cell.

In some embodiments, the signalling domain comprises one or more copies of an amino acid sequence according to SEQ ID NO:23 or SEQ ID NO:24. In some embodiments, the signalling domain comprises at least 1, 2, 3, 4, 5 or 6 copies of an amino acid sequence according to SEQ ID NO:23. In some embodiments, the signalling domain comprises at least 1, 2, or 3 copies of an amino acid sequence according to SEQ ID NO:24.

In some embodiments, the signalling domain comprises an amino acid sequence which is, or which is derived from, the amino acid sequence of an ITAM-containing sequence of a protein having an ITAM-containing amino acid sequence. In some embodiments the signalling domain comprises an amino acid sequence which is, or which is derived from, the amino acid sequence of the intracellular domain of one of CD3-ζ, FcγRI, CD3ε, CD3δ, CD3γ, CD79α, CD79β, FcγRIIA, FcγRIIC, FcγRIIIA, FcγRIV or DAP12. In some embodiments the signalling domain comprises an amino acid sequence which is, or which is derived from, the intracellular domain of CD3-ζ.

In some embodiments, the signalling domain comprises an amino acid sequence which comprises, or consists of, an amino acid sequence having at least 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:25.

The signalling domain may additionally comprise one or more costimulatory sequences. A costimulatory sequence is an amino acid sequence which provides for costimulation of the cell expressing the CAR of the present disclosure. Costimulation promotes proliferation and survival of a CAR-expressing cell upon binding to the target antigen, and may also promote cytokine production, differentiation, cytotoxic function and memory formation by the CAR-expressing cell. Molecular mechanisms of T cell costimulation are reviewed in Chen and Flies, 2013 Nat Rev Immunol 13(4): 227-242.

A costimulatory sequence may be, or may be derived from, the amino acid sequence of a costimulatory protein. In some embodiments the costimulatory sequence is an amino acid sequence which is, or which is derived from, the amino acid sequence of the intracellular domain of a costimulatory protein.

Upon binding of the CAR to the target antigen, the costimulatory sequence provides costimulation to the cell expressing the CAR costimulation of the kind which would be provided by the costimulatory protein from which the costimulatory sequence is derived upon ligation by its cognate ligand. By way of example in the case of a CAR comprising a signalling domain comprising a costimulatory sequence derived from CD28, binding to the target antigen triggers signalling in the cell expressing the CAR of the kind that would be triggered by binding of CD80 and/or CD86 to CD28. Thus a costimulatory sequence is capable of delivering the costimulation signal of the costimulatory protein from which the costimulatory sequence is derived.

In some embodiments, the costimulatory protein may be a member of the B7-CD28 superfamily (e.g. CD28, ICOS), or a member of the TNF receptor superfamily (e.g. 4-1BB, OX40, CD27, DR3, GITR, CD30, HVEM). In some embodiments, the costimulatory sequence is, or is derived from, the intracellular domain of one of CD28, 4-1BB, ICOS, CD27, OX40, HVEM, CD2, SLAM, TIM-1, CD30, GITR, DR3, CD226 and LIGHT. In some embodiments, the costimulatory sequence is, or is derived from, the intracellular domain of CD28.

In some embodiments the signalling domain comprises more than one non-overlapping costimulatory sequences. In some embodiments the signalling domain comprises 1, 2, 3, 4, 5 or 6 costimulatory sequences. Plural costimulatory sequences may be provided in tandem.

Whether a given amino acid sequence is capable of initiating signalling mediated by a given costimulatory protein can be investigated e.g. by analysing a correlate of signalling mediated by the costimulatory protein (e.g. expression/activity of a factor whose expression/activity is upregulated or downregulated as a consequence of signalling mediated by the costimulatory protein).

Costimulatory proteins upregulate expression of genes promoting cell growth, effector function and survival through several transduction pathways. For example, CD28 and ICOS signal through phosphatidylinositol 3 kinase (PI3K) and AKT to upregulate expression of genes promoting cell growth, effector function and survival through NF-κB, mTOR, NFAT and AP1/2. CD28 also activates AP1/2 via CDC42/RAC1 and ERK1/2 via RAS, and ICOS activates C-MAF. 4-1 BB, OX40, and CD27 recruit TNF receptor associated factor (TRAF) and signal through MAPK pathways, as well as through PI3K.

In some embodiments the signalling domain comprises a costimulatory sequence which is, or which is derived from CD28.

In some embodiments, the signalling domain comprises a costimulatory sequence which comprises, or consists of, an amino acid sequence having at least 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:26.

Kofler et al. Mol. Ther. (2011) 19: 760-767 describes a variant CD28 intracellular domain in which the lck kinase binding site is mutated in order to reduce induction of IL-2 production on CAR ligation, in order to minimise regulatory T cell-mediated suppression of CAR-T cell activity. The amino acid sequence of the variant CD28 intracellular domain is shown in SEQ ID NO:27.

In some embodiments, the signalling domain comprises a costimulatory sequence which comprises, or consists of, an amino acid sequence having at least 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:27.

In some embodiments, the signalling domain comprises, or consists of, an amino acid sequence having at least 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:28.

Hinge Region

The CAR may further comprise a hinge region. The hinge region may be provided between the antigen-binding domain and the transmembrane domain. The hinge region may also be referred to as a spacer region. A hinge region is an amino acid sequence which provides for flexible linkage of the antigen-binding and transmembrane domains of the CAR.

The presence, absence and length of hinge regions has been shown to influence CAR function (reviewed e.g. in Dotti et al., Immunol Rev (2014) 257(1) supra).

In some embodiments, the CAR comprises a hinge region which comprises, or consists of, an amino acid sequence which is, or which is derived from, the CH1-CH2 hinge region of human IgG1, a hinge region derived from CD8α, e.g. as described in WO 2012/031744 A1, or a hinge region derived from CD28, e.g. as described in WO 2011/041093 A1. In some embodiments, the CAR comprises a hinge region derived from the CH1-CH2 hinge region of human IgG1.

In some embodiments, the hinge region comprises, or consists of, an amino acid sequence having at least 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:29 or 30.

In some embodiments, the CAR comprises a hinge region which comprises, or consists of, an amino acid sequence which is, or which is derived from, the CH2-CH3 region (i.e. the Fc region) of human IgG1.

In some embodiments, the hinge region comprises, or consists of, an amino acid sequence having at least 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:31.

Hombach et al., Gene Therapy (2010) 17:1206-1213 describes a variant CH2-CH3 region for reduced activation of FcγR-expressing cells such as monocytes and NK cells. The amino acid sequence of the variant CH2-CH3 region is shown in SEQ ID NO:32.

In some embodiments, the hinge region comprises, or consists of, an amino acid sequence having at least 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:32.

In some embodiments, the hinge region comprises, or consists of: an amino acid sequence which is, or which is derived from, the CH1-CH2 hinge region of human IgG1, and an amino acid sequence which is, or which is derived from, the CH2-CH3 region (i.e. the Fc region) of human IgG1.

In some embodiments, the hinge region comprises, or consists of, an amino acid sequence having at least 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:33.

Additional Sequences

The CAR may additionally comprise a signal peptide (also known as a leader sequence or signal sequence). Signal peptides normally consist of a sequence of 5-30 hydrophobic amino acids, which form a single alpha helix. Secreted proteins and proteins expressed at the cell surface often comprise signal peptides. Signal peptides are known for many proteins, and are recorded in databases such as Gen-Bank, UniProt and Ensembl, and/or can be identified/predicted e.g. using amino acid sequence analysis tools such as SignalP (Petersen et al., 2011 Nature Methods 8: 785-786) or Signal-BLAST (Frank and Sippl, 2008 Bioinformatics 24: 2172-2176).

The signal peptide may be present at the N-terminus of the CAR, and may be present in the newly synthesised CAR. The signal peptide provides for efficient trafficking of the CAR to the cell surface.

Signal peptides are removed by cleavage, and thus are not comprised in the mature CAR expressed by the cell surface.

In some embodiments, the signal peptide comprises, or consists of, an amino acid sequence having at least 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:34.

In some embodiments the CAR comprises one or more linker sequences between the different domains (i.e. the antigen-binding domain, hinge region, transmembrane domain, signalling domain). In some embodiments the CAR comprises one or more linker sequences between subsequences of the domains (e.g. between VH and VL of an antigen-binding domain).

Linker sequences are known to the skilled person, and are described, for example in Chen et al., Adv Drug Deliv Rev (2013) 65(10): 1357-1369, which is hereby incorporated by reference in its entirety. In some embodiments, a linker sequence may be a flexible linker sequence. Flexible linker sequences allow for relative movement of the amino acid sequences which are linked by the linker sequence. Flexible linkers are known to the skilled person, and several are identified in Chen et al., Adv Drug Deliv Rev (2013) 65(10): 1357-1369. Flexible linker sequences often comprise high proportions of glycine and/or serine residues. In some embodiments, the linker sequence comprises at least one glycine residue and/or at least one serine residue. In some embodiments the linker sequence consists of glycine and serine residues. In some embodiments, the linker sequence has a length of 1-2, 1-3, 1-4, 1-5, 1-10, 1-20, 1-30, 1-40 or 1-50 amino acids.

In some embodiments a linker sequence comprises, or consists, of the amino acid sequence shown in SEQ ID NO:16. In some embodiments a linker sequence comprises, or consists, of 1, 2, 3, 4 or 5 tandem copies of the amino acid sequence shown in SEQ ID NO:16.

The CARs may additionally comprise further amino acids or sequences of amino acids. For example, the antigen-binding molecules and polypeptides may comprise amino acid sequence(s) to facilitate expression, folding, trafficking, processing, purification or detection. For example, the CAR may comprise a sequence encoding a His, (e.g. 6×His), Myc, GST, MBP, FLAG, HA, E, or Biotin tag, optionally at the N- or C-terminus. In some embodiments the CAR comprises a detectable moiety, e.g. a fluorescent, luminescent, immuno-detectable, radio, chemical, nucleic acid or enzymatic label.

Particular Exemplary CARs

In some embodiments of the present disclosure, the CAR comprises, or consists of: an extracellular moiety of the anti-CD30 HRS3 scFv domain, connected to spacer and hinge domains derived from the CH2-CH3 of human IgG1, the transmembrane and intracellular domains of CD28, and the and the intracellular domain of CD3ζ.

In some embodiments of the present disclosure, the CAR comprises, or consists of:

An antigen-binding domain comprising or consisting of an amino acid sequence having at least 60%, 65%, 70%, 75%, 80%, 85%, 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:18;

A hinge region comprising or consisting of an amino acid sequence having at least 60%, 65%, 70%, 75%, 80%, 85%, 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:33;

A transmembrane domain comprising or consisting of an amino acid sequence having at least 60%, 65%, 70%, 75%, 80%, 85%, 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:20; and A signalling domain comprising or consisting of an amino acid sequence having at least 60%, 65%, 70%, 75%, 80%, 85%, 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:28.

In some embodiments of the present disclosure, the CAR comprises, or consists of an amino acid sequence having at least 60%, 65%, 70%, 75%, 80%, 85%, 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:35 or 36.

In some embodiments, the CAR is selected from an embodiment of a CD30-specific CAR described in Hombach et al. Cancer Res. (1998) 58(6):1116-9, Hombach et al. Gene Therapy (2000) 7:1067-1075, Hombach et al. J Immunother. (1999) 22(6):473-80, Hombach et al. Cancer Res. (2001) 61:1976-1982, Hombach et al. J Immunol (2001) 167:6123-6131, Savoldo et al. Blood (2007) 110(7):2620-30, Koehler et al. Cancer Res. (2007) 67(5):2265-2273, Di Stasi et al. Blood (2009) 113(25):6392-402, Hombach et al. Gene Therapy (2010) 17:1206-1213, Chmielewski et al. Gene Therapy (2011) 18:62-72, Kofler et al. Mol. Ther. (2011) 19(4):760-767, Gilham, Abken and Pule. Trends in Mol. Med. (2012) 18(7):377-384, Chmielewski et al. Gene Therapy (2013) 20:177-186, Hombach et al. Mol. Ther. (2016) 24(8):1423-1434, Ramos et al. J. Clin. Invest. (2017)

127(9):3462-3471, WO 2015/028444 A1 or WO 2016/008973 A1, all of which are hereby incorporated by reference in their entirety.

CD30-Specific CAR-Expressing T Cells

Aspects of the present disclosure relate to immune cells comprising/expressing CD30-specific chimeric antigen receptors (CARs), particularly, CD30-specific CAR-expressing T cells.

It will be appreciated that where cells are referred to herein in the singular (i.e. "a/the cell"), pluralities/populations of such cells are also contemplated.

CAR-expressing T cells may express or comprise a CAR according to the present disclosure. CAR-expressing T cells may comprise or express nucleic acid encoding a CAR according to the present disclosure. It will be appreciated that a CAR-expressing cell comprises the CAR it expresses. It will also be appreciated that a cell expressing nucleic acid encoding a CAR also expresses and comprises the CAR encoded by the nucleic acid.

The T cell may express e.g. CD3 polypeptides (e.g. CD3γ CD3ε CD3ζ or CD3δ), TCR polypeptides (TCRα or TCRβ), CD27, CD28, CD4 or CD8. In some embodiments, the T cell is a CD3+ T cell. In some embodiments, the T cell is a CD3+, CD4+ T cell. In some embodiments, the T cell is a CD3+, CD8+ T cell. In some embodiments, the T cell is a T helper cell ($T_H$ cell)). In some embodiments, the T cell is a cytotoxic T cell (e.g. a cytotoxic T lymphocyte (CTL)).

Methods for producing CAR-expressing T cells are well known to the skilled person. They generally involve modifying T cells to express/comprise a CAR, e.g. introducing nucleic acid encoding a CAR into T cells.

T cells (may be modified to comprise/express a CAR or nucleic acid encoding a CAR described herein according to methods that are well known to the skilled person. The methods generally comprise nucleic acid transfer for permanent (stable) or transient expression of the transferred nucleic acid.

Any suitable genetic engineering platform may be used to modify a cell according to the present disclosure. Suitable methods for modifying a cell include the use of genetic engineering platforms such as gammaretroviral vectors, lentiviral vectors, adenovirus vectors, DNA transfection, transposon-based gene delivery and RNA transfection, for example as described in Maus et al., Annu Rev Immunol (2014) 32:189-225, hereby incorporated by reference in its entirety.

Methods also include those described e.g. in Wang and Riviere Mol Ther Oncolytics. (2016) 3:16015, which is hereby incorporated by reference in its entirety. Suitable methods for introducing nucleic acid(s)/vector(s) into cells include transduction, transfection and electroporation.

Methods for generating/expanding populations of CAR-expressing T cells in vitro/ex vivo are well known to the skilled person. Suitable culture conditions (i.e. cell culture media, additives, stimulations, temperature, gaseous atmosphere), cell numbers, culture periods and methods for introducing nucleic acid encoding a CAR into cells, etc. can be determined by reference e.g. to Hombach et al. J Immunol 30 (2001) 167:6123-6131, Ramos et al. J. Clin. Invest. (2017) 127(9):3462-3471 and WO 2015/028444 A1, all of which are hereby incorporated by reference in their entirety.

Conveniently, cultures of cells according to the present disclosure may be maintained at 37° C. in a humidified atmosphere containing 5% $CO_2$. The cells of cell cultures can be established and/or maintained at any suitable density, as can readily be determined by the skilled person.

Cultures can be performed in any vessel suitable for the volume of the culture, e.g. in wells of a cell culture plate, cell culture flasks, a bioreactor, etc. In some embodiments cells are cultured in a bioreactor, e.g. a bioreactor described in Somerville and Dudley, Oncoimmunology (2012) 1 (8): 1435-1437, which is hereby incorporated by reference in its entirety. In some embodiments cells are cultured in a G-Rex® cell culture vessel, e.g. a G-Rex® flask or a G-Rex®100 bioreactor (Wilson Wolf Manufacturing).

T cells may be activated prior to introduction of nucleic acid encoding the CAR. For example, T cells within populations of PBMCs may be non-specifically activated by stimulation in vitro with agonist anti-CD3 and agonist anti-CD28 antibodies, in the presence of IL-2.

Introducing nucleic acid(s)/vector(s) into a cell may comprise transduction, e.g. retroviral transduction. Accordingly, in some embodiments the nucleic acid(s) is/are comprised in a viral vector(s), or the vector(s) is/are a viral vector(s). Transduction of immune cells with viral vectors is described e.g. in Simmons and Alberola-IIa, Methods Mol Biol. (2016) 1323:99-108, which is hereby incorporated by reference in its entirety.

Agents may be employed to enhance the efficiency of transduction. Hexadimethrine bromide (polybrene) is a cationic polymer which is commonly used to improve transduction, through neutralising charge repulsion between virions and sialic acid residues expressed on the cell surface. Other agents commonly used to enhance transduction include e.g. the poloxamer-based agents such as Lenti-BOOST™ transduction enhancer (Revvity, Inc. (formerly Sirion Biotech)), RetroNectin® reagent (Takara), Vectofusin®-1 transduction enhancer (Miltenyi Biotec) and also SureENTRY transduction reagent (Qiagen) and ViraDuctin™ lentivirus transduction kit (Cell Biolabs).

In some embodiments the methods comprise centrifuging the cells into which it is desired to introduce nucleic acid encoding the CAR in the presence of cell culture medium comprising viral vector comprising the nucleic acid (referred to in the art as 'spinfection').

In some embodiments, the methods comprises introducing a nucleic acid or vector according to the present disclosure by electroporation, e.g. as described in Koh et al., Molecular Therapy—Nucleic Acids (2013) 2, e114, which is hereby incorporated by reference in its entirety.

The methods generally comprise introducing a nucleic acid encoding a CAR into a cell, and culturing the cell under conditions suitable for expression of the nucleic acid/CAR by the cell. In some embodiments, the methods culturing T cells into which nucleic acid encoding a CAR has been introduced in order to expand their number. In some embodiments, the methods comprise culturing T cells into which nucleic acid encoding a CAR has been introduced in the presence of IL-7 and/or IL-15 (e.g. recombinant IL-7 and/or IL-15).

In some embodiments the methods further comprise purifying/isolating CAR-expressing T cells, e.g. from other cells (e.g. cells which do not express the CAR). Methods for purifying/isolating immune cells from heterogeneous populations of cells are well known in the art, and may employ e.g. FACS- or MACS-based methods for sorting populations of cells based on the expression of markers of the immune cells. In some embodiments the methods purifying/isolating cells of a particular type, e.g. CAR-expressing CD8+ T cells, CAR-expressing CTLs).

In preferred embodiments, CD30-specific CAR-expressing T cells may be generated from T cells within populations of PBMCs by a process comprising: stimulating PBMCs with antagonist anti-CD3 and anti-CD28 antibodies, transducing the cells with a viral vector (e.g. a gamma-retroviral vector) encoding the CD30-specific CAR, and subsequently culturing the cells in the presence of IL-7 and IL-15.

A CD30-specific CAR-expressing T cell according to the present disclosure may display certain functional properties of a T cell in response to CD30, or in response a cell comprising/expressing CD30. In some embodiments, the properties are functional properties associated with effector T cells, e.g. cytotoxic T cells.

In some embodiments, a CD30-specific CAR-expressing T cell may display one or more of the following properties: cytotoxicity to a cell comprising/expressing CD30; proliferation, IFNγ expression, CD107a expression, IL-2 expression, TNFα expression, perforin expression, granzyme expression, granulysin expression, and/or FAS ligand (FASL) expression in response to stimulation with CD30, or in response to exposure to a cell comprising/expressing CD30; anti-cancer activity (e.g. cytotoxicity to cancer cells, tumor growth inhibition, reduction of metastasis, etc.) against cancer comprising cells expressing CD30.

Cell proliferation/population expansion can be investigated by analysing cell division or the number of cells over a period of time. Cell division can be analysed, for example, by in vitro analysis of incorporation of $^3$H-thymidine or by CFSE dilution assay, e.g. as described in Fulcher and Wong, Immunol Cell Biol (1999) 77(6): 559-564, hereby incorporated by reference in entirety. Proliferating cells can also be identified by analysis of incorporation of 5-ethynyl-2'-deoxyuridine (EdU) by an appropriate assay, as described e.g. in Buck et al., Biotechniques. 2008 June; 44(7):927-9, and Sali and Mitchison, PNAS USA 2008 Feb. 19; 105(7): 2415-2420, both hereby incorporated by reference in their entirety.

As used herein, "expression" may be gene or protein expression. Gene expression encompasses transcription of DNA to RNA, and can be measured by various means known to those skilled in the art, for example by measuring levels of mRNA by quantitative real-time PCR (qRT-PCR), or by reporter-based methods. Similarly, protein expression can be measured by various methods well known in the art, e.g. by antibody-based methods, for example by western blot, immunohistochemistry, immunocytochemistry, flow cytometry, ELISA, ELISPOT, or reporter-based methods.

Cytotoxicity and cell killing can be investigated, for example, using any of the methods reviewed in Zaritskaya et al., Expert Rev Vaccines (2011), 9(6):601-616, hereby incorporated by reference in its entirety. Examples of in vitro assays of cytotoxicity/cell killing assays include release assays such as the $^{51}$Cr release assay, the lactate dehydrogenase (LDH) release assay, the 3-(4,5-dimethylthiazol-2-yl)-2,5-diphenyl tetrazolium bromide (MTT) release assay, and the calcein-acetoxymethyl (calcein-AM) release assay. These assays measure cell killing based on the detection of factors released from lysed cells. Cell killing by a given cell type can be analysed e.g. by co-culturing the test cells with the given cell type, and measuring the number/proportion of cells viable/dead test cells after a suitable period of time.

Cells may be evaluated for anti-cancer activity by analysis in an appropriate in vitro assays or in vivo models of the relevant cancer.

Lymphodepleting Chemotherapy

Aspects of the present disclosure employ lymphodepleting chemotherapy.

As used herein, "lymphodepleting chemotherapy" refers to treatment with a chemotherapeutic agent which results in depletion of lymphocytes (e.g. T cells, B cells, NK cells, NKT cells or innate lymphoid cell (ILCs), or precursors thereof) within the subject to which the treatment is administered. A "lymphodepleting chemotherapeutic agent" refers to a chemotherapeutic agent which results in depletion of lymphocytes.

Lymphodepleting chemotherapy and its use in methods of treatment by adoptive cell transfer are described e.g. in Klebanoff et al., Trends Immunol. (2005) 26(2):111-7 and Muranski et al., Nat Clin Pract Oncol. (2006) (12):668-81, both of which are hereby incorporated by reference in their entirety. The aim of lymphodepleting chemotherapy is to deplete the recipient subject's endogenous lymphocyte population.

In the context of treatment of disease by adoptive transfer of immune cells, lymphodepleting chemotherapy is typically administered prior to adoptive cell transfer, to condition the recipient subject to receive the adoptively transferred cells. Lymphodepleting chemotherapy is thought to promote the persistence and activity of adoptively transferred cells by creating a permissive environment, e.g. through elimination of cells expressing immunosuppressive cytokines, and creating the 'lymphoid space' required for expansion and activity of adoptively transferred lymphoid cells.

Chemotherapeutic agents commonly used in lymphodepleting chemotherapy include e.g. fludarabine, bedamustine, cyclophosphamide and pentostatin.

Aspects and embodiments of the present disclosure are particularly concerned with lymphodepleting chemotherapy comprising administration of fludarabine and/or bendamustine. In particular embodiments, lymphodepleting chemotherapy according to the present disclosure comprises administration of fludarabine and bendamustine Fludarabine is a purine analog that inhibits DNA synthesis by interfering with ribonucleotide reductase and DNA polymerase. It is often employed as a chemotherapeutic agent for the treatment of leukemia (particularly chronic lymphocytic leukemia, acute myeloid leukemia, acute lymphocytic leukemia) and lymphoma (particularly non-Hodgkin's Lymphoma). Fludarabine may be administered intravenously or orally.

Bendamustine is an alkylating agent which causes intrastrand and inter-strand cross-links between DNA bases. It is often employed as a chemotherapeutic agent for the treatment of chronic lymphocytic leukemia, multiple myeloma and non-Hodgkin's Lymphoma. Bendamustine is typically administered intravenously.

Methods of Treatment

The present disclosure provides methods for the treatment of CD30-positive cancer, articles for use in such methods, and the use of articles for the manufacture of medicaments for use in such methods.

The methods generally comprise administering a lymphodepleting chemotherapy to a subject having a CD30-positive cancer, and subsequently administering CD30-specific CAR-expressing T cells to the subject.

Specifically, the present disclosure provides a method of treating a CD30-positive cancer in a subject, comprising: (i) administering a lymphodepleting chemotherapy to the subject, and (ii) subsequently administering CD30-specific CAR-expressing T cells to the subject.

The present disclosure also provides CD30-specific CAR-expressing T cells (e.g. a population of such cells) for use in a method of treating a CD30-positive cancer, wherein the method comprises: (i) administering a lymphodepleting chemotherapy to the subject, and (ii) subsequently administering CD30-specific CAR-T cells to the subject. The present disclosure also provides the use of CD30-specific CAR-expressing T cells (e.g. a population of such cells) in the manufacture of a medicament for use in a method of treating a CD30-positive cancer, wherein the method comprises: (i) administering a lymphodepleting chemotherapy to the subject, and (ii) subsequently administering CD30-specific CAR-T cells to the subject.

The present disclosure also provides a lymphodepleting chemotherapeutic agent (e.g. fludarabine and/or bendamustine) for use in a method of treating a CD30-positive cancer, wherein the method comprises: (i) administering a lymphodepleting chemotherapy (e.g. comprising administering fludarabine and/or bendamustine) to the subject, and (ii) subsequently administering CD30-specific CAR-T cells to the subject. The present disclosure also provides the use of a lymphodepleting chemotherapeutic agent (e.g. fludarabine and/or bendamustine) in the manufacture of a medicament for use in a method of treating a CD30-positive cancer, wherein the method comprises: (i) administering a lymphodepleting chemotherapy (e.g. comprising administering fludarabine and/or bendamustine) to the subject, and (ii) subsequently administering CD30-specific CAR-T cells to the subject.

The present disclosure also provides fludarabine for use in a method of treating a CD30-positive cancer, wherein the method comprises: (i) administering a lymphodepleting chemotherapy comprising administering fludarabine (e.g. a lymphodepleting chemotherapy comprising administering fludarabine and bendamustine) to the subject, and (ii) subsequently administering CD30-specific CAR-T cells to the subject. The present disclosure also provides the use of fludarabine in the manufacture of a medicament for use in a method of treating a CD30-positive cancer, wherein the method comprises: (i) administering a lymphodepleting chemotherapy comprising administering fludarabine (e.g. a lymphodepleting chemotherapy comprising administering fludarabine and bendamustine) to the subject, and (ii) subsequently administering CD30-specific CAR-T cells to the subject.

The present disclosure also provides bendamustine for use in a method of treating a CD30-positive cancer, wherein the method comprises: (i) administering a lymphodepleting chemotherapy comprising administering bendamustine (e.g. a lymphodepleting chemotherapy comprising administering fludarabine and bendamustine) to the subject, and (ii) subsequently administering CD30-specific CAR-T cells to the subject. The present disclosure also provides the use of bendamustine in the manufacture of a medicament for use in a method of treating a CD30-positive cancer, wherein the method comprises: (i) administering a lymphodepleting chemotherapy comprising administering bendamustine (e.g. a lymphodepleting chemotherapy comprising administering fludarabine and bendamustine) to the subject, and (ii) subsequently administering CD30-specific CAR-T cells to the subject.

The present disclosure also provides the combination of fludarabine and bendamustine (e.g. a pharmaceutical composition or combination comprising fludarabine and bendamustine) for use in a method of treating a CD30-positive cancer, wherein the method comprises: (i) administering a lymphodepleting chemotherapy comprising administering fludarabine and bendamustine to the subject, and (ii) subsequently administering CD30-specific CAR-T cells to the subject. The present disclosure also provides the use of the combination of fludarabine and bendamustine (e.g. a pharmaceutical composition or combination comprising fludarabine and bendamustine) in the manufacture of a medicament for use in a method of treating a CD30-positive cancer, wherein the method comprises: (i) administering a lymphodepleting chemotherapy comprising administering fludarabine and bendamustine to the subject, and (ii) subsequently administering CD30-specific CAR-T cells to the subject.

Administration of cells and chemotherapeutic agents in accordance with the methods of the present disclosure is preferably in a "therapeutically effective" amount, this being sufficient to show therapeutic benefit to the subject.

The actual amount administered, and rate and time-course of administration, will depend on the nature and severity of the cancer to be treated, and the nature of the agent. Prescription of treatment, e.g. decisions on dosage etc., is within the responsibility of general practitioners and other medical doctors, and typically takes account of the cancer to be treated, the condition of the individual subject, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

For administration in accordance with the present disclosure, cells and chemotherapeutic agents are preferably formulated as medicaments or pharmaceutical compositions comprising pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilisers, solubilisers, surfactants (e.g., wetting agents), masking agents, colouring agents, flavouring agents, and sweetening agents.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation. Suitable carriers, adjuvants, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 2nd edition, 1994.

The formulations may be prepared by any methods well known in the art of pharmacy. Such methods include the step of bringing into association the relevant active agent with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The cells and chemotherapeutic agents of the present disclosure may be formulated for a mode of administration which is acceptable in accordance with the agent and the cancer to be treated. For example, cells and chemotherapeutic agents according to the present invention may be formulated for intravascular administration, e.g. intravenous injection or infusion to a subject. Suitable formulations may comprise the selected agent in a sterile or isotonic medium.

In some embodiments, administering a lymphodepleting chemotherapy in accordance with the present disclosure preferably comprises administering fludarabine and bendamustine.

A course of lymphodepleting chemotherapy in accordance with the present disclosure may comprise multiple administrations of one or more chemotherapeutic agents. A course of lymphodepleting chemotherapy may comprise administering fludarabine and bendamustine at a dose described herein, and for a number of days described herein. By way of illustration, a course of lymphodepleting chemotherapy may comprise administering fludarabine at a dose of 30 mg/m$^2$ per day for 3 consecutive days, and administering bendamustine at a dose of 70 mg/m$^2$ per day for 3 consecutive days.

The day of administration of the final dose of a chemotherapeutic agent in accordance with a course of lymphodepleting chemotherapy may be considered to be the day of completion of the course of lymphodepleting chemotherapy.

In some embodiments, fludarabine is administered at a dose of 5 to 100 mg/m$^2$ per day, e.g. one of 15 to 90 mg/m$^2$ per day, 15 to 80 mg/m$^2$ per day, 15 to 70 mg/m$^2$ per day, 15 to 60 mg/m$^2$ per day, 15 to 50 mg/m$^2$ per day, 10 to 40 mg/m$^2$ per day, 5 to 60 mg/m$^2$ per day, 10 to 60 mg/m$^2$ per day, 15 to 60 mg/m$^2$ per day, 20 to 60 mg/m$^2$ per day or 25 to 60 mg/m$^2$ per day. In some embodiments, fludarabine is administered at a dose of 20 to 40 mg/m$^2$ per day, e.g. 25 to 35 mg/m$^2$ per day, e.g. about 30 mg/m$^2$ per day.

In some embodiments fludarabine is administered at a dose according to the preceding paragraph for more than one day and fewer than 14 consecutive days. In some embodiments, fludarabine is administered at a dose according to the preceding paragraph for one of 2 to 14 e.g. 2 to 13, 2 to 12, 2 to 11, 2 to 10, 2 to 9, 2 to 8, 2 to 7, 2 to 6, 2 to 5 or 2 to 4 consecutive days. In some embodiments, fludarabine is administered at a dose according to the preceding paragraph for 2 to 6 consecutive days, e.g. 2 to 4 consecutive days, e.g. 3 consecutive days.

In some embodiments fludarabine is administered at a dose of 15 to 60 mg/m$^2$ per day, for 2 to 6 consecutive days, e.g. at a dose of 30 mg/m$^2$ per day, for 3 consecutive days.

In some embodiments, bendamustine is administered at a dose of 10 to 200 mg/m$^2$ per day, e.g. one of 35 to 180 mg/m$^2$ per day, 35 to 160 mg/m$^2$ per day, 35 to 140 mg/m$^2$ per day, 35 to 120 mg/m$^2$ per day, 35 to 100 mg/m$^2$ per day, 35 to 80 mg/m$^2$ per day, 10 to 100 mg/m$^2$ per day, 15 to 100 mg/m$^2$ per day, 20 to 100 mg/m$^2$ per day, 25 to 100 mg/m$^2$ per day, 30 to 100 mg/m$^2$ per day, 35 to 100 mg/m$^2$ per day, 40 to 100 mg/m$^2$ per day, 45 to 100 mg/m$^2$ per day, 50 to 100 mg/m$^2$ per day, 55 to 100 mg/m$^2$ per day, 60 to 100 mg/m$^2$ per day, or 65 to 100 mg/m$^2$ per day.

In some embodiments bendamustine is administered at a dose according to the preceding paragraph for more than one day and fewer than 14 consecutive days. In some embodiments, bendamustine is administered at a dose according to the preceding paragraph for one of 2 to 14 e.g. 2 to 13, 2 to 12, 2 to 11, 2 to 10, 2 to 9, 2 to 8, 2 to 7, 2 to 6, 2 to 5 or 2 to 4 consecutive days. In some embodiments, bendamustine is administered at a dose according to the preceding paragraph for 2 to 6 consecutive days, e.g. 2 to 4 consecutive days, e.g. 3 consecutive days.

In some embodiments bendamustine is administered at a dose of 35 to 140 mg/m$^2$ per day, for 2 to 6 consecutive days, e.g. at a dose of 70 mg/m$^2$ per day, for 3 consecutive days.

In some embodiments the methods comprise administering fludarabine at a dose of 15 to 60 mg/m$^2$ per day (e.g. 30 mg/m$^2$ per day) and administering bendamustine at a dose of 35 to 140 mg/m$^2$ per day (e.g. 70 mg/m$^2$ per day), for 2 to 6 consecutive days (e.g. 3 consecutive days).

In some embodiments, fludarabine and bendamustine may be administered simultaneously or sequentially. Simultaneous administration refers to administration together, for example as a pharmaceutical composition containing both agents (i.e. in a combined preparation), or immediately after one another, and optionally via the same route of administration, e.g. to the same artery, vein or other blood vessel. Sequential administration refers to administration of one of the agents followed after a given time interval by separate administration of the other agent. It is not required that the agents are administered by the same route, although this is the case in some embodiments.

In some embodiments of courses of lymphodepleting chemotherapy in accordance with the present disclosure, fludarabine and bendamustine are administered on the same day or days. By way of illustration, in the example of a course of lymphodepleting chemotherapy comprising administering fludarabine at a dose of 30 mg/m$^2$ per day for 3 consecutive days, and administering bendamustine at a dose of 70 mg/m$^2$ per day for 3 consecutive days, the fludarabine and bendamustine may be administered on the same 3 consecutive days. In such an example, the course of lymphodepleting chemotherapy may be said to be completed on the final day of the 3 consecutive days on which fludarabine and bendamustine are administered to the subject.

Lymphodepleting chemotherapy may be administered by intravenous infusion over an appropriate period of time. In some embodiments, a lymphodepleting chemotherapeutic agent may be administered by intravenous infusion over a period of 15 to 60 min, e.g. 20 to 40 min, e.g. about 30 min.

Aspects of the present disclosure also comprise administering CD30-specific CAR-expressing T cells to a subject having a CD30-positive cancer. The methods therefore involve adoptive cell transfer.

Adoptive cell transfer generally refers to a process by which cells (e.g. immune cells) are obtained from a subject, typically by drawing a blood sample from which the cells are isolated. The cells are then typically modified and/or expanded, and then administered either to the same subject (in the case of adoptive transfer of autologous/autogeneic cells) or to a different subject (in the case of adoptive transfer of allogeneic cells). Adoptive cell transfer is typically aimed at providing a population of cells with certain desired characteristics to a subject, or increasing the frequency of such cells with such characteristics in that subject. Adoptive transfer may be performed with the aim of introducing a cell or population of cells into a subject, and/or increasing the frequency of a cell or population of cells in a subject.

Adoptive transfer of CD30-specific CAR-expressing T cells is described, for example, in Hombach et al. J Immunol (2001) 167:6123-6131, Ramos et al. J. Clin. Invest. (2017) 127(9):3462-3471 and WO 2015/028444 A1, all of which are incorporated by reference hereinabove. The skilled person is able to determine appropriate reagents and procedures for adoptive transfer of such cells in accordance with the methods of the present disclosure by reference to these documents.

The present disclosure provides methods comprising administering a T cell comprising/expressing a CD30-specific CAR, or a T cell comprising/expressing nucleic acid encoding a CD30-specific CAR, to a subject.

In some embodiments, the methods comprise modifying a T cell to comprise/express a CD30-specific CAR. In some embodiments, the methods comprise modifying a T cell to comprise/express nucleic acid encoding a CD30-specific CAR.

In some embodiments, the methods comprise:
(a) modifying a T cell to express or comprise a CD30-specific CAR, or to express or comprise nucleic acid encoding a CD30-specific CAR; and
(b) administering T cell modified to express or comprise a CD30-specific CAR, or modified to express or comprise nucleic acid encoding a CD30-specific CAR, to a subject.

In some embodiments, the methods comprise:
(a) isolating or obtaining a population of immune cells comprising T cells (e.g. PBMCs);
(b) modifying a T cell to express or comprise a CD30-specific CAR, or to express or comprise nucleic acid encoding a CD30-specific CAR; and
(c) administering a T cell modified to express or comprise a CD30-specific CAR, or modified to express or comprise nucleic acid encoding a CD30-specific CAR, to a subject.

In some embodiments, the methods comprise:
(a) isolating or obtaining a population of immune cells comprising T cells (e.g. PBMCs) from a subject;
(b) modifying a T cell to express or comprise a CD30-specific CAR, or to express or comprise nucleic acid encoding a CD30-specific CAR; and
(c) administering a T cell modified to express or comprise a CD30-specific CAR, or modified to express or comprise nucleic acid encoding a CD30-specific CAR, to a subject.

In some embodiments, the subject from which the population of immune cells comprising T cells (e.g. PBMCs) is isolated is the same subject to which cells are administered (i.e., adoptive transfer may be of autologous/autogeneic cells). In some embodiments, the subject from which the population of immune cells comprising T cells (e.g. PBMCs) is isolated is a different subject to the subject to which cells are administered (i.e., adoptive transfer may be of allogeneic cells).

In some embodiments the methods may comprise one or more of:
obtaining a blood sample from a subject;
isolating a population of immune cells comprising T cells (e.g. PBMCs) from a blood sample which has been obtained from a subject;
culturing the immune cells in vitro or ex vivo cell culture;
modifying a T cell to express or comprise a CD30-specific CAR, or to express or comprise nucleic acid encoding a CD30-specific CAR (e.g. by transduction with a viral vector encoding such CAR, or a viral vector comprising such nucleic acid);
culturing T cells modified to express or comprise a CD30-specific CAR, or modified to express or comprise nucleic acid encoding a CD30-specific CAR in in vitro or ex vivo cell culture;
collecting/isolating T cells modified to express or comprise a CD30-specific CAR, or modified to express or comprise nucleic acid encoding a CD30-specific CAR;
formulating T cells modified to express or comprise a CD30-specific CAR, or modified to express or comprise nucleic acid encoding a CD30-specific CAR to a pharmaceutical composition, e.g. by mixing the cells with a pharmaceutically acceptable adjuvant, diluent, or carrier;
administering T cells modified to express or comprise a CD30-specific CAR, or modified to express or comprise nucleic acid encoding a CD30-specific CAR, or a pharmaceutical composition comprising such cells, to a subject.

In some embodiments, the methods may additionally comprise treating the cells or subject to induce/enhance expression of CAR and/or to induce/enhance proliferation or survival of cells comprising/expressing the CAR.

In some embodiments, a blood sample may be obtained by venesection or leukapheresis, which are both well known to the skilled person. The total blood volume of a blood sample obtained by venesection is preferably between 100 ml to 500 ml, e.g. 150 ml to 300 ml, e.g. about 200 ml. Blood sample collection is preferably performed a sufficient period of time prior to planned administration of CD30-specific CAR-expressing T cells to a subject for the production of a sufficient quantity of CD30-specific CAR-expressing T cells for a dose to be administered to a subject. In some embodiments, a blood sample is obtained at 6 to 8 weeks prior to planned administration of CD30-specific CAR-expressing T cells to a subject.

In the methods of the present disclosure, CD30-specific CAR-expressing T cells are administered to the subject after lymphodepleting chemotherapy has been administered to the subject.

In some embodiments, CD30-specific CAR-expressing T cells are administered to a subject within a specified period of time following completion of a course of lymphodepleting chemotherapy, e.g. a course of lymphodepleting chemotherapy described herein. That is, CD30-specific CAR-expressing T cells are administered to a subject within a specified period of time following the day of administration of the final dose of a chemotherapeutic agent in accordance with administration of a lymphodepleting chemotherapy in accordance with the present disclosure.

In some embodiments, CD30-specific CAR-expressing T cells are administered to a subject within 1 to 28 days, e.g. one of 1 to 21 days, 1 to 14 days, 1 to 7 days, 2 to 7 days, 2 to 5 days, or 3 to 5 days of completion of a course of lymphodepleting chemotherapy described herein. In some embodiments, CD30-specific CAR-expressing T cells are administered to a subject within 2 to 14 days of completion of a course of lymphodepleting chemotherapy described herein. In some embodiments, CD30-specific CAR-expressing T cells are administered to a subject within 3 to 5 days of completion of a course of lymphodepleting chemotherapy described herein.

In some embodiments, CD30-specific CAR-expressing T cells are administered at a dose of $1 \times 10^7$ cells/m$^2$ to $1 \times 10^9$ cells/m$^2$, e.g. one of $5 \times 10^7$ cells/m$^2$ to $1 \times 10^9$ cells cells/m$^2$, $1 \times 10^8$ cells cells/m$^2$ to $9 \times 10^8$ cells/m$^2$, $2 \times 10^8$ cells/m$^2$ to $8 \times 10^8$ cells/m$^2$, or $2 \times 10^8$ cells/m$^2$ to $8 \times 10^8$ cells/m$^2$. In some embodiments, CD30-specific CAR-expressing T cells are administered at a dose of $1 \times 10^8$ cells/m$^2$ to $6 \times 10^8$ cells/m$^2$.

In some embodiments, CD30-specific CAR-expressing T cells are administered at a dose of $2 \times 10^8$ cells/m$^2$. In some embodiments, CD30-specific CAR-expressing T cells are administered at a dose of $4 \times 10^8$ cells/m$^2$. In some embodiments, CD30-specific CAR-expressing T cells are administered at a dose of $6 \times 10^8$ cells/m$^2$.

In some embodiments, CD30-specific CAR-expressing T cells are administered at a dose greater than $1 \times 10^8$ cells/m$^2$, e.g. a dose greater than $2 \times 10^8$ cells/m$^2$, $3 \times 10^8$ cells/m$^2$, $4 \times 10^8$ cells/m$^2$, $5 \times 10^8$ cells/m$^2$, $6 \times 10^8$ cells/m$^2$, $7 \times 10^8$ cells/m$^2$, $8 \times 10^8$ cells/m$^2$. Such embodiments are contemplated in particular where the cancer to be treated is non-Hodgkin's Lymphoma. In some embodiments, CD30-specific CAR-expressing T cells are administered at a dose of $2 \times 10^8$ cells/m$^2$ to $8 \times 10^8$ cells/m$^2$. In some embodiments, CD30-specific CAR-expressing T cells are administered at a dose of $3 \times 10^8$ cells/m$^2$ to $8 \times 10^8$ cells/m$^2$. In some embodiments, CD30-specific CAR-expressing T cells are administered at a dose of $4 \times 10^8$ cells/m$^2$ to $8 \times 10^8$ cells/m$^2$. In some embodiments, CD30-specific CAR-expressing T cells are administered at a dose of $5 \times 10^8$ cells/m$^2$ to $8 \times 10^8$ cells/m$^2$. In some embodiments, CD30-specific CAR-expressing T cells are administered at a dose of $6 \times 10^8$ cells/m$^2$ to $8 \times 10^8$ cells/m$^2$.

In some embodiments, CD30-specific CAR-expressing T cells are administered at a dose of $1 \times 10^6$ to $1 \times 10^7$ cells per kg body weight, e.g. one of $1.5 \times 10^6$ to $9 \times 10^6$ cells per kg body weight, $2.0 \times 10^6$ to $8 \times 10^6$ cells per kg body weight, $2.0 \times 10^6$ to $6 \times 10^6$ cells per kg body weight or $2.0 \times 10^6$ to $5 \times 10^6$ cells per kg body weight. Administration of doses calculated in this manner is contemplated in particular where the subject to be treated weighs 50 kg or less.

Administration of CD30-specific CAR-expressing T cells may be administered by intravenous infusion. Administration may be in a volume containing 0.5 to $6 \times 10^7$ cells/ml, e.g. 1 to $3 \times 10^7$ cells/ml.

Multiple (e.g. 2, 3, 4 or more) doses of CD30-specific CAR-expressing T cells may be provided. Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, or more hours or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. The decision to administer one or more further dose(s) of CD30-specific CAR-expressing T cells may be made based on the response of the subject to treatment, and/or availability of CD30-specific CAR-expressing T cells.

In some embodiments, the methods of the present disclosure may comprise further therapeutic or prophylactic intervention, e.g. additional chemotherapy, immunotherapy, radiotherapy, surgery, vaccination and/or hormone therapy. Such further therapeutic or prophylactic intervention may occur before, during and/or after the administration of lymphodepleting chemotherapy or CD30-specific CAR-expressing T cells in accordance with the methods of the present disclosure, and may occur the same or different routes of administration.

Additional chemotherapy may employ a chemical entity, e.g. small molecule pharmaceutical, antibiotic, DNA intercalator, protein inhibitor (e.g. kinase inhibitor), or a biological agent, e.g. antibody, antibody fragment, aptamer, nucleic acid (e.g. DNA, RNA), peptide, polypeptide, or protein. The drug may be formulated as a pharmaceutical composition or medicament. The formulation may comprise one or more drugs (e.g. one or more active agents) together with one or more pharmaceutically acceptable diluents, excipients or carriers. Radiotherapy may employ ionising radiation, e.g. radiotherapy using X-rays or γ-rays.

Prior to administration of a lymphodepleting chemotherapy and/or CD30-specific chimeric antigen receptor (CAR)-expressing T cells in accordance with aspects of the present disclosure, a subject may be administered bridging therapy. Bridging therapy may be administered to the subject after blood sample collection, and prior to administration of a lymphodepleting chemotherapy. Bridging therapy is therapy designed to carry the subject through to treatment in accordance with the methods of the present disclosure. The decision to administer bridging therapy at the discretion and under the control of medical practitioners. Bridging therapy may comprise administering or more of steroids, chemotherapy, palliative radiation therapy, an immune checkpoint inhibitor or anti-CD30 antibodies to the subject. Bridging therapy may be followed by a washout period prior to administration of a lymphodepleting chemotherapy in accordance with the methods of the present disclosure. The washout period ensures adequate recovery of toxicity associated with the bridging therapy prior to administration of the first dose of a lymphodepleting chemotherapeutic agent in accordance with a lymphodepleting chemotherapy according to the present disclosure. The appropriate washout period depends on the particular bridging therapy employed. Where steroids are administered as a bridging therapy, the washout period may be 1 week. Where chemotherapy is administered as a bridging therapy, the washout period may be 3 weeks. Where palliative radiation therapy is administered as a bridging therapy, the washout period may be 2 weeks. Where an immune checkpoint inhibitor is administered as a bridging therapy, the washout period may be 3 weeks. Where anti-CD30 antibodies are administered as a bridging therapy, the washout period may be 8 weeks.

Particular exemplary embodiments of methods of treatment in accordance with the present disclosure are described below.

In some embodiments, the method comprises:
(i) administering fludarabine at a dose of 30 mg/m$^2$/day and bendamustine at a dose of 70 mg/m$^2$/day to a subject for 3 consecutive days, and
(ii) 2 to 5 days (e.g. 2 days) after the final day of administration of fludarabine and bendamustine, administering CD30-specific CAR-expressing T cells to the subject at a dose of 1×10$^8$ cells/m$^2$.

In some embodiments, the method comprises:
(i) administering fludarabine at a dose of 30 mg/m$^2$/day and bendamustine at a dose of 70 mg/m$^2$/day to a subject for 3 consecutive days, and
(ii) 2 to 5 days (e.g. 2 days) after the final day of administration of fludarabine and bendamustine, administering CD30-specific CAR-expressing T cells to the subject at a dose of 2×10$^8$ cells/m$^2$.

In some embodiments, the method comprises:
(i) administering fludarabine at a dose of 30 mg/m$^2$/day and bendamustine at a dose of 70 mg/m$^2$/day to a subject for 3 consecutive days, and
(ii) 2 to 5 days (e.g. 2 days) after the final day of administration of fludarabine and bendamustine, administering CD30-specific CAR-expressing T cells to the subject at a dose of 2×10$^8$ to 6×10$^8$ cells/m$^2$ (e.g. 4×10$^8$ cells/m$^2$).

Subjects

The subject in accordance with aspects the present disclosure may be any animal or human. The subject is preferably mammalian, more preferably human. The subject may be a non-human mammal, but is more preferably human. The subject may be a patient. The subject may be male or female. The subject may be an adult subject (aged ≥18 years), a pediatric subject (aged ≤18 years), or an adolescent subject (aged ≥12 and ≤21 years; e.g. an early adolescent (aged ≥12 and ≤14 years), middle adolescent (aged ≥15 and ≤17 years), or late adolescent (aged ≥18 and ≤21 years)). The subject may be aged ≤75 years.

The subject may have a CD30-positive cancer (e.g. a CD30-positive cancer according to an embodiment described herein). The subject may have a CD30-positive tumor. The subject may have been determined to have a CD30-positive cancer, may have been diagnosed with a CD30-positive cancer, may be suspected of having a CD30-positive cancer, or may be at risk of developing a CD30-positive cancer. In some embodiments, the subject may be selected for treatment in accordance with the methods of the present disclosure based on determination that the subject has a CD30-positive cancer. The subject may have at least one measurable lesions according to the Revised Criteria for Response Assessment: The Lugano Classification (described e.g. in Cheson et al., J Clin Oncol (2014) 32: 3059-3068, which is hereby incorporated by reference in its entirety).

The subject may be a subject that has relapsed following a treatment for the cancer. The subject may have responded to a treatment for the cancer (e.g. a first line therapy for the cancer), but the cancer may have subsequently re-emerged/progressed, e.g. after a period of remission.

The subject may be a subject that failed to respond to a treatment for the cancer. The subject may not have responded to a treatment for the cancer (e.g. a first line therapy for the cancer). The subject may not have displayed a partial or complete response to a treatment for the cancer (e.g. a first line therapy for the cancer).

The subject may be autogeneic/autologous with respect to the source of the cells from which the CD30-specific CAR-expressing T cells administered in accordance with the methods of the disclosure are derived. The subject to which the CD30-specific CAR-expressing T cells are administered may be the same subject from which the blood sample or cells are obtained for the production of the CD30-specific CAR-expressing T cells. The subject to which the CD30-specific CAR-expressing T cells are administered may be genetically identical to the subject from which the blood sample or cells are obtained for the production of the CD30-specific CAR-expressing T cells. The subject to which the CD30-specific CAR-expressing T cells are administered may comprise MHC/HLA genes encoding MHC/HLA molecules which are identical to the MHC/HLA molecules encoded by the MHC/HLA genes of the subject from which the blood sample or cells are obtained for the production of the CD30-specific CAR-expressing T cells.

Alternatively, the subject may be allogeneic/non-autologous with respect to the source of the cells from which the CD30-specific CAR-expressing T cells administered in accordance with the methods of the disclosure are derived. The subject to which the CD30-specific CAR-expressing T cells are administered may be a different subject to the subject from which the blood sample or cells are obtained for the production of the CD30-specific CAR-expressing T cells. The subject to which the CD30-specific CAR-expressing T cells are administered may be genetically non-identical to the subject from which the blood sample or cells are obtained for the production of the CD30-specific CAR-expressing T cells. The subject to which the CD30-specific CAR-expressing T cells are administered may comprise MHC/HLA genes encoding MHC/HLA molecules which are identical to the MHC/HLA molecules encoded by the MHC/HLA genes of the subject from which the blood sample or cells are obtained for the production of the CD30-specific CAR-expressing T cells.

EFFECTS ACHIEVED BY TREATMENT ACCORDING TO THE PRESENT DISCLOSURE

Methods of the present disclosure may be characterised by reference to treatment effects and/or clinical outcomes achieved by the method.

Treatment of a subject in accordance with the methods of the present disclosure achieves one or more of the following treatment effects: reduces the number of CD30-positive cancer cells in the subject, reduces the size of a CD30-positive tumor/lesion in the subject, inhibits (e.g. prevents or slows) growth of CD30-positive cancer cells in the subject, inhibits (e.g. prevents or slows) growth of a CD30-positive tumor/lesion in the subject, inhibits (e.g. prevents or slows)

the development/progression of a CD30-positive cancer (e.g. to a later stage, or metastasis), reduces the severity of symptoms of a CD30-positive cancer in the subject, increases survival of the subject (e.g. progression free survival or overall survival), reduces a correlate of the number or activity of CD30-positive cancer cells in the subject, and/or reduces CD30-positive cancer burden in the subject.

Subjects may be evaluated in accordance with the Revised Criteria for Response Assessment: The Lugano Classification (described e.g. in Cheson et al., J Clin Oncol (2014) 32: 3059-3068, incorporated by reference hereinabove) in order to determine their response to treatment. In some embodiments, treatment of a subject in accordance with the methods of the present disclosure achieves one of the following: complete response, partial response, or stable disease.

Methods of the present disclosure may be characterised by reference to effects achieved/responses observed at a population level. That is, in some embodiments the methods of the present disclosure may be characterised by reference to effects achieved/responses observed when the treatment is administered to more than one subject, e.g. a population of subjects. A population of subjects may comprise 2 or more, e.g. one of 5, 10, 15, 20, 25, 30, 40, 50, 60, 70, 80, 90 or 100 or more subjects.

Effects achieved/responses observed at a population level may be expressed in terms of the proportion (e.g. percentage) of treated subjects displaying a given clinical outcome (e.g. complete response, partial response, overall response (compete response+partial response), stable disease, progressive disease).

The proportion of treated subjects displaying a given clinical outcome may be referred to as the "rate" for the clinical outcome. By way of illustration, the percentage of subjects displaying a complete response to treatment may be referred to as the complete response rate.

In some embodiments, treatment in accordance with the methods of the present disclosure achieves an overall response rate (i.e. complete response plus partial response) of 50% or greater, e.g. one of 55%, 60%, 65%, 70%, 75%, 80%, 85%, 90% or 95% or greater, or an overall response rate of 100%. In some embodiments, treatment in accordance with the methods of the present disclosure achieves an overall response rate of 70% or greater, e.g. one of 71%, 72%, 73%, 74%, 75%, 76%, 77%, 78%, 79%, 80% or 81% or greater.

In some embodiments, treatment in accordance with the methods of the present disclosure achieves a complete response rate of 50% or greater, e.g. one of 55%, 60%, 65%, 70%, 75%, 80%, 85%, 90% or 95% or greater, or a complete response rate of 100%. In some embodiments, treatment in accordance with the methods of the present disclosure achieves a complete response rate of 70% or greater, e.g. one of 71%, 72%, 73%, 74% or 75% or greater.

In some embodiments, treatment in accordance with the methods of the present disclosure achieves a progressive disease rate of 50% or less, e.g. one of 45%, 40%, 35%, 30%, 25%, 20%, 15%, 10% or 5% or less, or a progressive disease rate of 0%. In some embodiments, treatment in accordance with the methods of the present disclosure achieves a progressive disease rate of 30% or less, e.g. one of 29%, 28%, 27%, 26%, 25%, 24%, 23%, 22%, 21%, 20%, 19%, 18%, 17%, 16%, 15%, 14% or 13% or less.

In some embodiments, treatment in accordance with the methods of the present disclosure achieves a 1 year progression free survival rate of 20% or greater, e.g. one of 25%, 30%, 35%, 40%, 45%, 50%, 55%, 60%, 65%, 70%, 75%, 80%, 85%, 90%, or 95% or greater, or a 1 year progression free survival rate of 100%. In some embodiments, treatment in accordance with the methods of the present disclosure achieves a complete response rate of 40% or greater, e.g. one of 41%, 42%, 43%, 44%, 45%, 46%, 47%, 48%, 49%, 50%, 51%, 52%, 53%, 54%, 55%, 56% or 57% or greater.

In some embodiments, treatment in accordance with the methods of the present disclosure achieves a median progression free survival of 1 month or greater, e.g. one of 2, 3, 4, 5, 6, 7, 8, 9, 10, 11, 12, 13, 14, 15, 16, 17, 18, 19, 20, 21, 22, 23 or 24 months or greater. In some embodiments, treatment in accordance with the methods of the present disclosure achieves a median progression free survival of 9 months or greater, e.g. one of 10, 11, 12 or 13 months or greater.

In some embodiments, treatment in accordance with the methods of the present disclosure achieves a 1 year overall survival rate of 90% or greater, e.g. one of 91%, 92%, 93%, 94%, 95%, 96%, 97%, 98% or 99% or greater, or 1 year overall survival rate of 100%.

In some embodiments, treatment in accordance with the methods of the present disclosure achieves a median overall survival of 6 months or greater, e.g. one of 7, 8, 9, 10, 11, 12, 13, 14, 15, 16, 17, 18, 19, 20, 21, 22, 23 or 24 months or greater.

In some embodiments, treatment in accordance with the methods of the present disclosure achieves a 1 year duration of response rate (e.g. in subjects achieving a complete response or a partial response) of 20% or greater, e.g. one of 25%, 30%, 35%, 40%, 45%, 50%, 55%, 60%, 65%, 70%, 75%, 80%, 85%, 90%, or 95% or greater, or a 1 year duration of response rate of 100%.

In some embodiments, treatment in accordance with the methods of the present disclosure achieves a median duration of response (e.g. in subjects achieving a complete response or a partial response) of 1 month or greater, e.g. one of 2, 3, 4, 5, 6, 7, 8, 9, 10, 11, 12, 13, 14, 15, 16, 17, 18, 19, 20, 21, 22, 23 or 24 months or greater.

In embodiments of the present disclosure, treatment effects and clinical outcomes may be characterised by reference to the effects/outcomes (e.g. clinical responses) achieved by a treatment in accordance with a reference method. A reference method may be a method comprising administering CD30-specific CAR-expressing T cells to a subject.

In some embodiments, a reference method may comprise treatment by administering CD30-specific CAR-expressing T cells (e.g. at a dose of $2 \times 10^7$ cells/m$^2$, $1 \times 10^8$ cells/m$^2$ or $2 \times 10^8$ cells/m$^2$) without prior administration of a lymphodepleting chemotherapy. In some embodiments, a reference method may comprise treatment of a CD30-positive cancer by administering CD30-specific CAR-expressing T cells to a subject as described in Ramos et al., J Clin Invest. (2017) 127(9):3462-3471, or in accordance with an intervention described for NCT01316146 (reproduced below):

Drug: CAR.CD30 T cells
Three dose levels:
Group One, $2 \times 10^{\wedge}7$ cells/m$^2$
Group Two, $1 \times 10^{\wedge}8$ cells/m$^2$
Group Three, $2 \times 10^{\wedge}8$ cells/m$^2$;
Cell Administration: CAR+ activated T lymphocytes given by intravenous injection over 1-10 minutes through either a peripheral or a central line. Expected volume=1-50 cc.

In some embodiments, a reference method may comprise treatment by administering lymphodepleting chemotherapy comprising administering fludarabine and cyclophosphamide (e.g. at a dose of 30 mg/m$^2$/day fludarabine and 500 mg/m$^2$/day cyclophosphamide for three consecutive days), and subsequently (e.g. within 2 to 14 days of completion of the course of lymphodepleting chemotherapy) administering CD30-specific CAR-expressing T cells (e.g. at a dose of 2×10$^7$ cells/m$^2$, 1×10$^8$ cells/m$^2$ or 2×10$^8$ cells/m$^2$). In some embodiments, a reference method may comprise treatment of a CD30-positive cancer as described in Ramos et al., Biol Blood Marrow Transplant 25 (2019) S7-S75, Abstract 79, or in accordance with the intervention described for NCT02917083 (reproduced below):

Genetic: CAR T Cells

Three dose levels. Each patient receives one infusion of CAR modified T cells according to the following dosing schedule:

Dose Level One: 2×10^7 cells/m$^2$. Dose Level Two: 1×10^8 cells/m$^2$. Dose Level Three: 2×10^8 cells/m$^2$.

Drug: Cyclophosphamide

Patients who are not post autologous transplant will receive three daily doses of cyclophosphamide (Cy: 500 mg/m$^2$/day) finishing at least 48 hours before T cell infusion, but no later than 2 weeks prior to infusion of the cells.

Other Name: Cytoxan

Drug: Fludarabine

Patients who are not post autologous transplant will receive fludarabine (Flu: 30 mg/m$^2$/day), finishing at least 48 hours before T cell infusion, but no later than 2 weeks prior to infusion of the cells.

Treatment in accordance with the methods of the present disclosure may be associated with an improved treatment effect and/or an improved clinical outcome as compared to treatment in accordance with a reference method.

Treatment in accordance with the methods of the present disclosure may achieve one or more of: a greater reduction in the number of CD30-positive cancer cells in the subject, a greater reduction in the size of a CD30-positive tumor/lesion in the subject, greater inhibition of growth of CD30-positive cancer cells in the subject, greater inhibition of growth of a CD30-positive tumor/lesion in the subject, greater inhibition of the development/progression of a CD30-positive cancer (e.g. to a later stage, or metastasis), a greater reduction in the severity of symptoms of a CD30-positive cancer in the subject, a greater increase in survival of the subject (e.g. progression free survival or overall survival), a greater reduction in a correlate of the number or activity of CD30-positive cancer cells in the subject, and/or a greater reduction in CD30-positive cancer burden in the subject, as compared to treatment in accordance with a reference method.

A "greater" reduction/inhibition/increase may be a reduction/inhibition/increase which is greater than 1 times, e.g. one of ≥1.01 times, ≥1.02 times, ≥1.03 times, ≥1.04 times, ≥1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times or ≥10 times the level of reduction/inhibition/increase achieved by the treatment in accordance with a reference method.

Reduction/inhibition may be to a level which is less than 1 times, e.g. ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, 50.45 times, ≤0.4 times, ≤0.35 times, ≤0.3 times, ≤0.25 times, ≤0.2 times, ≤0.15 times, ≤0.1 times, ≤0.05 times, or ≤0.01 times the level achieved by treatment in accordance with a reference method.

An increase may be to a level which is greater than 1 times, e.g. one of ≥1.01 times, ≥1.02 times, ≥1.03 times, ≥1.04 times, ≥1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, 29 times or ≥10 times the level achieved by treatment in accordance with a reference method.

In some embodiments, treatment in accordance with the methods of the present disclosure is associated with an improved clinical outcome (e.g. clinical response) as compared to the treatment in accordance with a reference method.

Treatment in accordance with the methods of the present disclosure may achieve one or more of: an increased overall response (i.e. complete response plus partial response) rate, an increased complete response rate, a reduced progressive disease rate, an increased 1 year progression free survival rate, an increased median progression free survival, an increased 1 year overall survival rate, increased median overall survival, an increased 1 year duration of response rate or, increased an increased median duration of response, as compared to the treatment in accordance with a reference method.

An "increased" rate/median may be a rate/median which is greater than 1 times, e.g. one of ≥1.01 times, 1.02 times, ≥1.03 times, ≥1.04 times, 1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, 29 times or 10 times the rate/median achieved by the treatment in accordance with a reference method.

An "reduced" rate may be a rate which is less than 1 times, e.g. ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the rate achieved by the treatment in accordance with a reference method.

Treatment in accordance with the methods of the present disclosure may be associated with a reduced proportion of subjects displaying adverse events, as compared to treatment in accordance with a reference method.

Treatment in accordance with the methods of the present disclosure may be associated with a reduced proportion of subjects displaying one or more of the following, as compared to treatment in accordance with a reference method: lymphopenia, leukopenia, neutropenia, thrombocytopenia, anemia, hypoalbuminemia, hyponatremia, dyspnea, rash, headache, pharyngitis, lung Infection, cytokine Release syndrome, grade 3/4 neutropenia at day 28, grade 3/4 thrombocytopenia at day 28, grade 3/4 anemia at day 28, prolonged grade 3/4 neutropenia (e.g. at month 3), prolonged grade 3/4 thrombocytopenia (e.g. at month 3), or prolonged grade 3/4 anemia (e.g. at month 3).

Sequence Identity

Pairwise and multiple sequence alignment for the purposes of determining percent identity between two or more amino acid or nucleic acid sequences can be achieved in various ways known to a person of skill in the art, for instance, using publicly available computer software such as ClustalOmega (Söding, J. 2005, Bioinformatics 21, 951-960), T-coffee (Notredame et al. 2000, J. Mol. Biol. (2000)

302, 205-217), Kalign (Lassmann and Sonnhammer 2005, BMC Bioinformatics, 6(298)) and MAFFT (Katoh and Standley 2013, Molecular Biology and Evolution, 30(4)

772-780 software. When using such software, the default parameters, e.g. for gap penalty and extension penalty, are preferably used.

| | | Sequences |
|---|---|---|
| SEQ ID NO: | DESCRIPTION | SEQUENCE |
| 1 | Human CD30 isoform 1 (UniProt: P28908-1, v1) | MRVLLAALGLLFLGALRAFPQDRPFEDTCHGNPSHYYDKAVRRCCYRCPMGLFPTQQCPQRPTD CRKQCEPDYYLDEADRCTACVTCSRDDLVEKTPCAWNSSRVCECRPGMFCSTSAVNSCARCFF HSVCPAGMIVKFPGTAQKNTVCEPASPGVSPACASPENCKEPSSGTIPQAKPTPVSPATSSASTM PVRGGTRLAQEAASKLTRAPDSPSSVGRPSSDPGLSPTQPCPEGSGDCRKQCEPDYYLDEAGR CTACVSCSRDDLVEKTPCAWNSSRTCECRPGMICATSATNSCARCVPYPICAAETVTKPQDMAE KDTTFEAPPLGTQPDCNPTPENGEAPASTSPTQSLLVDSQASKTLPIPTSAPVALSSTGKPVLDAG PVLFWVILVLVVVVGSSAFLLCHRRACRKRIRQKLHLCYPVQTSQPKLELVDSRPRRSSTQLRSGA SVTEPVAEERGLMSQPLMETCHSVGAAYLESLPLQDASPAGGPSSPRDLPEPRVSTEHTNNKIEK IYIMKADTVIVGTVKAELPEGRGLAGPAEPELEEELEADHTPHYPEQETEPPLGSCSDVMLSVEEE GKEDPLPTAASGK |
| 2 | Human CD30 isoform 2 (UniProt: P28908-2) | MSQPLMETCHSVGAAYLESLPLQDASPAGGPSSPRDLPEPRVSTEHTNNKIEKIYIMKADTVIVGT VKAELPEGRGLAGPAEPELEEELEADHTPHYPEQETEPPLGSCSDVMLSVEEEGKEDPLPTAAS GK |
| 3 | Human CD30 isoform 3 (UniProt: P28908-3) | MFCSTSAVNSCARCFFHSVCPAGMIVKFPGTAQKNTVCEPASPGVSPACASPENCKEPSSGTIP QAKPTPVSPATSSASTMPVRGGTRLAQEAASKLTRAPDSPSSVGRPSSDPGLSPTQPCPEGSGD CRKQCEPDYYLDEAGRCTACVSCSRDDLVEKTPCAWNSSRTCECRPGMICATSATNSCARCVP YPICAAETVTKPQDMAEKDTTFEAPPLGTQPDCNPTPENGEAPASTSPTQSLLVDSQASKTLPIPT SAPVALSSTGKPVLDAGPVLFWVVILVLVVVVGSSAFLLCHRRACRKRIRQKLHLCYPVQTSQPKLE LVDSRPRRSSTLRSGASVTEPVAEERGLMSQPLMETCHSVGAAYLESLPLQDASPAGGPSSPRD LPEPRVSTEHTNNKIEKIYIMKADTVIVGTVKAELPEGRGLAGPAEPELEEELEADHTPHYPEQETE PPLGSCSDVMLSVEEEGKEDPLPTAASGK |
| 4 | Human CD30 signal peptide | MRVLLAALGLLFLGALRA |
| 5 | Human CD30 extracellular domain | FPQDRPFEDTCHGNPSHYYDKAVRRCCYRCPMGLFPTQQCPQRPTDCRKQCEPDYYLDEADR CTACVTCSRDDLVEKTPCAWNSSRVCECRPGMFCSTSAVNSCARCFFHSVCPAGMIVKFPGTA QKNTVCEPASPGVSPACASPENCKEPSSGTIPQAKPTPVSPATSSASTMPVRGGTRLAQEAASK LTRAPDSPSSVGRPSSDPGLSPTQPCPEGSGDCRKQCEPDYYLDEAGRCTACVSCSRDDLVEK TPCAWNSSRTCECRPGMICATSATNSCARCVPYPICAAETVTKPQDMAEKDTTFEAPPLGTQPD CNPTPENGEAPASTSPTQSLLVDSQASKTLPIPTSAPVALSSTGKPVLDAG |
| 6 | Human CD30 transmembrane domain | PVLFWWILVLVVVVGSSAFLL |
| 7 | Human CD30 cytoplasmic domain | CHRRACRKRIRQKLHLCYPVQTSQPKLELVDSRPRRSSTQLRSGASVTEPVAEERGLMSQPLME TCHSVGAAYLESLPLQDASPAGGPSSPRDLPEPRVSTEHTNNKIEKIYIMKADTVIVGTVKAELPEG RGLAGPAEPELEEELEADHTPHYPEQETEPPLGSCSDVMLSVEEEGKEDPLPTAASGK |
| 8 | HRS3 HC-CDR1 | GYTFTTYT |
| 9 | HRS3 HC-CDR2 | INPSSGCS |
| 10 | HRS3 HC-CDR3 | ARRADYGNYEYTWFAY |
| 11 | HRS3 LC-CDR1 | QNVGTN |
| 12 | HRS3 LC-CDR2 | SAS |
| 11 | HRS3 LC-CDR3 | QQYHTYPLT |
| 14 | HRS3 VH | QVQLQQSGAELARPGASVKMSCKASGYTFTTYTIHWWRRRPGHDLEWIGYINPSSGCSDYNQNF KGKTTLTADKSSNTAYMQLNSLTSEDSAVYYCARRADYGNYEYTWFAYWGQGTTVTVSS |
| 15 | HRS3 VL | VIELTQSPKFMSTSVGDRVNVTYKASQNVGTNVAWFQQKPGQSPKVLIYSASYRYSGVPDRFTG SGSGTDFTLTISNVQSEDLAEYFCQQYHTYPLTFGGGTKLEIK |
| 16 | G₄S | GGGGS |
| 17 | HRS3 scFv linker | SGGGSGGGGSGGGGS |
| 18 | HRS3 scFv | QVQLQQSGAELARPGASVKMSCKASGYTFTTYTIHWWRRRPGHDLEWIGYINPSSGCSDYNQNF KGKTTLTADKSSNTAYMQLNSLTSEDSAVYYCARRADYGNYEYTWFAYWGQGTTVTVSSSGGG SGGGGSGGGGSVIELTQSPKFMSTSVGDRVNVTYKASQNVGTNVAWFQQKPGQSPKVLIYSAS YRYSGVPDRFTGSGSGTDFTLTISNVQSEDLAEYFCQQYHTYPLTFGGGTKLEIK |

-continued

| Sequences | | |
| --- | --- | --- |

| SEQ ID NO: | DESCRIPTION | SEQUENCE |
| --- | --- | --- |
| 19 | HRS3 epitope | ATSSASTMPVRGGTRLAQEAASKLTRAPDSPSSVGRPSSDPGLSPTQPCPEGSGDCRKQCEPD YYLDEAGRCTACVSCSRDDLVEKTPCAWNSSRTCECRPGMICATSATNSCARCVPYPICAAETV TKPQDMAEKDTTFEAPPLGTQPDC |
| 20 | Human CD28 transmembrane domain | FWWLVVVGGVLACYSLLVTVAFII |
| 21 | Human CD3ζ transmembrane domain | LCYLLDGILFIYGVILTALFL |
| 22 | Human CD8α transmembrane domain | IYIWAPLAGTCGVLLLSLVITLYCNHRN |
| 23 | ITAM consensus | YXXL/I wherein X = any amino acid |
| 24 | Larger ITAM consensus | YXXL/I(X)$_{6-8}$YXXL/I wherein X = any amino acid |
| 25 | Human CD3ζ intracellular domain | RVKFSRSADAPAYQQGQNQLYNELNLGRREEYDVLDKRRGRDPEMGGKPRRKNPQEGLYNEL QKDKMAEAYSEIGMKGERRRGKGHDGLYQGLSTATKDTYDALHMQALPPR |
| 26 | Human CD28 intracellular domain | FWWRSKRSRLLHSDYMNMTPRRPGPTRKHYQPYAPPRDFAAYRS |
| 27 | Human CD28 intracellular domain with mutated lck binding site | FWWRSKRSRLLHSDYMNMTPRRPGPTRKHYQAYAAARDFAAYRS |
| 28 | CAR signalling domain 1 | FWWRSKRSRLLHSDYMNMTPRRPGPTRKHYQPYAPPRDFAAYRSRVKFSRSADAPAYQQGQN QLYNELNLGRREEYDVLDKRRGRDPEMGGKPRRKNPQEGLYNELQKDKMAEAYSEIGMKGERR RGKGHDGLYQGLSTATKDTYDALHMQALPPR |
| 29 | Human IgG1 CH1-CH2 hinge region | EPKSCDKTHTCP |
| 30 | Human IgG1 CH1-CH2 hinge region C103P variant | EPKSPDKTHTCP |
| 31 | Human IgG1 CH2-CH3 hinge region | PCPAPELLGGPSVFLFPPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKGQPREPQVYTLPPSRDE LTKNQVSLTCLVKGFYPSDIAVEWESNGQPENNYKTTPPVLDSDGSFFLYSKLTVDKSRWQQGN VFSCSVMHEALHNHYTQKSLSLSPGK |
| 32 | Human IgG1 CH2-CH3 hinge region variant | PCPAPPVAGPSVFLFPPKPKDTLMIARTPEVTCVVVDVSHEDPEVKFNWYVDGVEVHNAKTKPRE EQYNSTYRVVSVLTVLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSKLTVDKSRWQQGNV FSCSVMHEALHNHYTQKSLSLSPGKKDPK |
| 33 | CAR hinge region | EPKSPDKTHTCPPCPAPELLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKALPAPIEKTISKAKGQPRE PQVYTLPPSRDELTKNQVSLTCLVKGFYPSDIAVEWESNGQPENNYKTTPPVLDSDGSFFLYSKL TVDKSRWQQGNVFSCSVMHEALHNHYTQKSLSLSPGK |
| 34 | Signal peptide 1 | MDFQVQIFSFLLISASVIMS |
| 35 | CD30.CAR (lacking signal peptide) | QVQLQQSGAELARPGASVKMSCKASGYTFTTYTIHWWRRRPGHDLEWIGYINPSSGCSDYNQNF KGKTTLTADKSSNTAYMQLNSLTSEDSAVYYCARRADYGNYEYTWFAYWGQGTTVTVSSSGGG SGGGGSGGGGSVIELTQSPKFMSTSVGDRVNVTYKASQNVGTNVAWFQQKPGQSPKVLIYSAS YRYSGVPDRFTGSGSGTDFTLTISNVQSEDLAEYFCQQYHTYPLTFGGGTKLEIKRSDPAEPKSP DKTHTCPPCPAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTVDKS RWQQGNVFSCSVMHEALHNHYTQKSLSLSPGKKDPKFWWLVVVGGVLACYSLLVTVAFIIFWWR SKRSRLLHSDYMNMTPRRPGPTRKHYQPYAPPRDFAAYRSRVKFSRSADAPAYQQGQNQLYNE LNLGRREEYDVLDKRRGRDPEMGGKPRRKNPQEGLYNELQKDKMAEAYSEIGMKGERRRGKG HDGLYQGLSTATKDTYDALHMQALPPR |

-continued

| | | Sequences |
|---|---|---|
| SEQ ID NO: | DESCRIPTION | SEQUENCE |
| 36 | CD30.CAR (with signal peptide) | MDFQVQIFSFLLISASVIMSRMAQVQLQQSGAELARPGASVKMSCKASGYTFTTYTIHWVRRRPG HDLEWIGYINPSSGCSDYNQNFKGKTTLTADKSSNTAYMQLNSLTSEDSAVYYCARRADYGNYE YTWFAYWGQGTTVTVSSSGGGSGGGGSGGGGSVIELTQSPKFMSTSVGDRVNVTYKASQNVG TNVAWFQQKPGQSPKVLIYSASYRYSGVPDRFTGSGSGTDFTLTISNVQSEDLAEYFCQQYHTYP LTFGGGTKLEIKRSDPAEPKSPDKTHTCPPCPAPELLGGPSVFLFPPKPKDTLMISRTPEVTCVVV DVSHEDPEVKFNWYVDGVEVHNAKTKPREEQYNSTYRVVSVLTVLHQDWLNGKEYKCKVSNKA LPAPIEKTISKAKGQPREPQVYTLPPSRDELTKNQVSLTCLVKGFYPSDIAVEWESNGQPENNYKT TPPVLDSDGSFFLYSKLTVDKSRWQQGNVFSCSVMHEALHNHYTQKSLSLSPGKKDPKFWWLVV VGGVLACYSLLVTVAFIIFWVRSKRSRLLHSDYMNMTPRRPGPTRKHYQPYAPPRDFAAYRSRVK FSRSADAPAYQQGQNQLYNELNLGRREEYDVLDKRRGRDPEMGGKPRRKNPQEGLYNELQKD KMAEAYSEIGMKGERRRGKGHDGLYQGLSTATKDTYDALHMQALPPR |

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Where a nucleic acid sequence is disclosed herein, the reverse complement thereof is also expressly contemplated.

Methods described herein may be performed in vitro or in vivo. In some embodiments, methods described herein are performed in vitro. The term "in vitro" is intended to encompass experiments with cells in culture whereas the term "in vivo" is intended to encompass experiments with intact multi-cellular organisms.

BRIEF DESCRIPTION OF THE FIGURES

Embodiments and experiments illustrating the principles of the invention will now be discussed with reference to the accompanying figures.

FIG. 3. Schematic overview of TESSCAR001 (NCT04268706) study design. Primary Endpoints: ORR as assessed by an Independent Radiology Review Committee; Secondary Endpoints: Safety, ORR as assessed by Investigator, DOR, PFS, OS, HRQoL; Exploratory Endpoints: Expansion and persistence of CD30.CAR-T cells in blood; immunogenicity; cytokine profiling; immunological parameters; tumor marker and ctDNA; Safety Assessments: AE and concomitant medication collection; Long-term follow-up: Additional safety monitoring×15 years. *2nd infusion of CD30.CAR-T cell: at the discretion of Principal Investigator and after discussion with the Sponsor or designee, a 2nd CD30.CAR-T infusion may be administrated if the patient has CR, PR or SD at the first response assessment and subsequently has disease progression at least 3 months post CD30.CAR-T infusion. Abbreviations: CR, complete response; DOR, duration of response; HRQoL, health related quality of life; OS, overall survival; ORR, objective response rate; PFS, progression-free survival; PD, progressive disease; PR, partial response; SD, stable disease.

EXAMPLES

Figure 1:
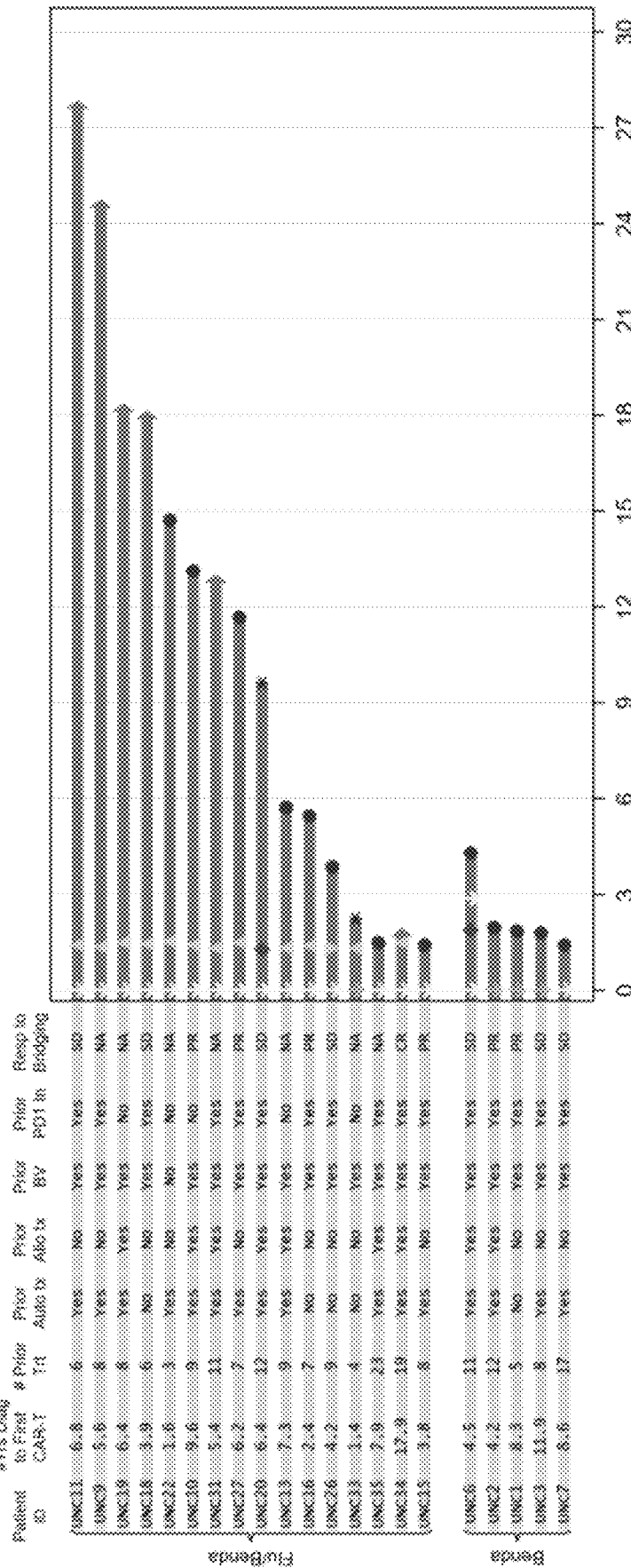
FIG. 1. Swimmer plot showing duration of Response of Classical HL Patients from LCCC 1532-ATL with Measurable Disease at the Time of Treatment (Data cutoff: 14 Feb. 2020).

In the following Examples, the inventors describe treatment of CD30-positive cancer using methods employing lymphodepleting chemotherapy and adoptive transfer of CD30-specific CAR-expressing T cells.

Example 1: Study LCCC 1532-ATL (NCT02690545): Phase 1/2 Study of the Administration of T Lymphocytes Expressing the CD30 Chimeric Antigen Receptor (CAR) for Relapsed or Refractory CD30+ Hodgkin Lymphoma and CD30+ Non-Hodgkin Lymphoma

1.1 OVERVIEW

A Phase 1/2 study in patients with relapsed or refractory Hodgkin Lymphoma was conducted at the University of North Carolina (UNC, Chapel Hill, North Carolina) in protocol NCT02690545.

Patients received autologous CD30.CAR-T manufactured in Good Manufacturing Practice (GMP)-compliant facilities, using a clinical grade gamma-retroviral vector and following a Standard Operating Procedure (SOP).

Patients with relapsed/refractory CD30$^+$ lymphomas who progressed after at least 2 lines of therapy were eligible for enrollment. BV treatment was allowed, but not within 4 weeks of the scheduled infusion of CD30.CAR-T cells. Documented CD30 expression by immunohistochemistry based on the institutional hematopathology standard was required, but there was no specific cutoff for the percentage of CD30$^+$ tumor cells.

Patients with CD30$^+$ T cell or anaplastic large cell lymphoma as well as CD30$^+$ B-cell lymphoma were also enrolled, but the present Example only reports the outcome of 34 patients with HL (26 patients).

Bridging chemotherapy, at the discretion of the treating physician, was allowed before lymphodepletion. The conditioning regimen consisted of bendamustine at a dose of 90 mg/m$^2$/day for 2 days for the first cohort of 8 patients, and bendamustine 70 mg/m$^2$/day and fludarabine 30 mg/m$^2$/day for 3 days for the subsequent 18 patients enrolled in the second cohort.

Infusion of CD30.CAR-T cells occurred 2-5 days after lymphodepletion. Patients received either 1×10$^8$ CAR-T cells/m$^2$ or 2×10$^8$ CAR-T cells/m$^2$. An expansion cohort of patients received the highest dose level of 2×10$^8$ CAR-T cells/m$^2$. A second infusion of CD30.CAR-T cells at the highest dose level was allowed in patients who had stable disease or partial response after the first treatment.

The primary objective of the Phase 1 portion of the study was to establish a safe dose of CD30.CAR-T cells to infuse after lymphodepletion. Secondary endpoints included ORR, duration of response (DOR), overall survival (OS), and measurement of the expansion and persistence of CD30.CAR-T in the peripheral blood after infusion. Data were analyzed separately in patients who received non-fludarabine-based lymphodepletion and those who received regimens containing fludarabine.

Response was assessed at 6-8 weeks after CD30.CAR-T cell infusion using the Lugano criteria (Cheson et al., J Clin Oncol (2014) 32: 3059-3068). Response rate was estimated only in patients who had active disease at the time of lymphodepletion.

1.2 PATIENT DEMOGRAPHICS

Between September 2016 and 14 Feb. 2020, 29 patients with HL were enrolled in LCCC 1532-ATL study and 26 received CD30.CAR-T cells. As of 14 Feb. 2020 data cutoff, there were 3 patients enrolled at LCCC 1532-ATL study who did not receive treatment. Of the 3 patients, 1 elected not to proceed with the clinical trial, 1 had no active disease at the time of collection, 1 failed CAR-T cell manufacturing due to intensive prior autologous stem cell transplant (ASCT), allogeneic stem cell transplant (alloSCT) and multiple donor lymphocyte infusions.

TABLE 1

Classical HL Patient Characteristics from LCCC 1532-ATL:

| Characteristics | | Benda n = 8* (%) | Flu/Benda n = 18 (%) |
|---|---|---|---|
| HL Subtype: n (%) | NS | 6 (75) | 11 (61) |
| | MC | 2 (25) | 2 (11) |
| | NOS | 0 | 5 (28) |
| Stage at | I-II | 1 (13) | 7 (39) |
| diagnosis: n (%) | III-IV | 7 (88) | 11 (61) |
| Age (years), median (range) | | 49 (23-67) | 31.5 (15-45) |
| Male sex: n (%) | | 5 (63) | 13 (72) |
| Prior Therapies, median (range) | | 7.5 (5-17) | 8 (3-23) |
| Bridging Therapy: n (%) | | 8 (100) | 10 (56) |
| Prior BV: n (%) | | 8 (100) | 17 (94) |
| Prior CPI: n (%) | | 7 (88) | 13 (72) |
| Prior ASCT: n (%) | | 7 (88) | 14 (78) |
| Prior alloSCT: n (%) | | 2 (25) | 8 (44) |
| CAR-T cells/m$^2$: | 2 × 10$^7$ | 0 | 0 |
| n (%) | 1 × 10$^8$ | 3 (38) | 1 (6) |
| | 2 × 10$^8$ | 5 (63) | 17 (94) | alloSCT = allogeneic stem cell transplant; ASCT = autologous stem cell transplant; Benda = bendamustine; BV = brentuximab vedotin; CPI = checkpoint inhibitor; Flu = fludarabine; HL = Hodgkin lymphoma; MC = mixed cellularity; NOS = not otherwise specified; NS = nodular sclerosis.

1.3 EFFICACY

Eighteen patients received bendamustine and fludarabine in LCCC 1532-ATL study. Of these, 2 patients were in CR at the time of infusion, maintained CR, and were not included in the efficacy analysis.

TABLE 2

Clinical Responses of Classical HL Patients from LCCC 1532-ATL with Measurable Disease at the Time of Treatment

| | | Bendamustine* n = 5 (%) | Flu/Benda** n = 16 (%) |
|---|---|---|---|
| ORR: n (%) | CR + PR | 0 (0%) | 13 (81.3%) |
| RR: n (%) | CR | 0 (0%) | 12 (75.0%) |
| | PR | 0 (0%) | 1 (6.3%) |
| | SD | 1 (20%) | 1 (6.3%) |
| | PD | 4 (80%) | 2 (12.5%) |

CR: complete response; ORR objective response rate; PR: partial response; RR: response rate; SD: stable disease, Benda: bendamustine; Flu: fludarabine
*3 patients were in CR prior to LD due to bridging therapy and are not included in the analysis.
**2 patients were in CR prior to LD due to bridging therapy and are not included in the analysis.

TABLE 3

| Subject ID | Age | Sex | No. of Prior Therapies | LD Regimen | CD30. CAR-T Dose | Response | Lymphodepletion related AE | CAR-T cell related AE |
|---|---|---|---|---|---|---|---|---|
| UNC 33 | 15 | Female | 4 | Flu/ Benda | $1 \times 10^8/m^2$ | CR | Anemia (G1) Anoexia (G1) Aminotransferase Elevated (G1) Cough (G1) Hyponatremia (G1) Hypophosphatemia (G1) Lymphopenia (G4) Neutropenia (G2) Thombocytopenia (G1) Vomiting (G1) Leukopenia (G2) | Alanine aminotransferase Elevated (G1) |

Characteristics, Clinical Responses and Safety Data of Classical HL Patients Under Age 18 from LCCC 1532-ATL In patients treated with lymphodepletion chemotherapy of bendamustine and fludarabine, the ORR was 81%, with CR reported in 12 patients (75%), PR in 1 patient (6%), SD in 1 patient (6%) and PD in 2 patients (13%) (Table 2). Among them, one patient under age 18 was treated, an achieved CR (Table 3).

*One patient who received two treatments (one at UNC and the second at BCM 2 years later) was considered.

Eight patients received lymphodepletion using bendamustine alone prior to CD30.CAR-T cell infusion. Of these 8 patients, 3 patients were in CR prior to lymphodepletion due to bridging therapy and were not included in the analysis (Table 2). None of the 5 patients with active disease showed objective clinical responses when treated (Table 2).

The duration of response (DOR) patients with measurable disease at the time of treatment is shown in FIG. 1. Among the 12 patients with CR after 1$^{st}$ infusion 6 patients had responses ongoing.

Figure 2:
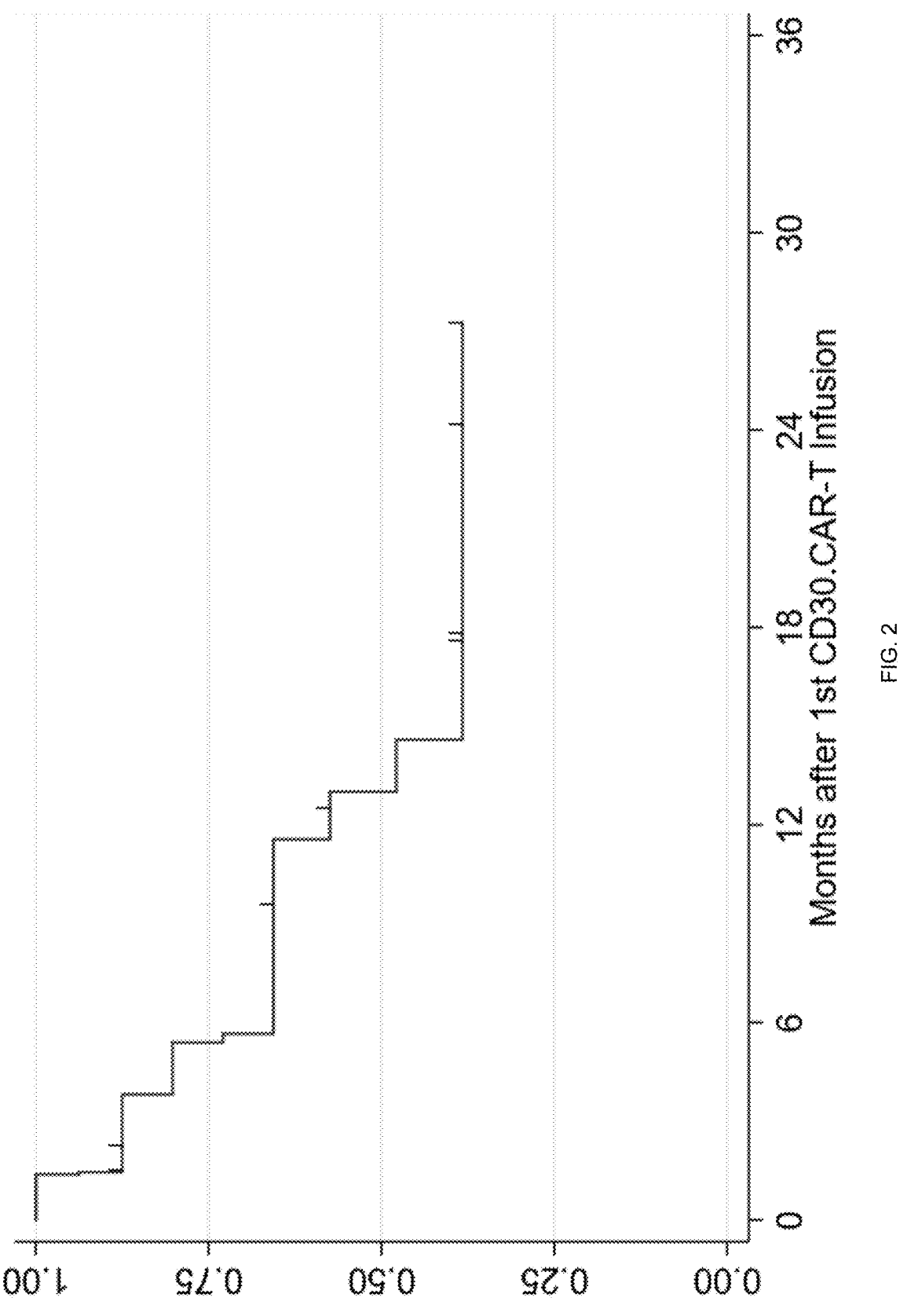
FIG. 2. Kaplan-Meier plot showing PFS of Classical HL Patients from LCCC 1532-ATL. The progression free survival of evaluable classical HL patients from LCCC 1532-ATL treated with bendamustine and fludarabine (n=16) is shown.

The 1-year PFS rate of 16 patients treated with bendamustine and fludarabine regimen was 57% (95% Cl: 28%-78%), with median PFS of 13.0 months (95% Cl: 5.4-NE)—see FIG. 2.

1.4 SAFETY

No dose limiting toxicities associated with CD30.CAR-T cell infusion was observed. The patient under age 18 treated did not experience CRS or other CAR-T cell related toxicity, except grade 1 ALT (Table 3).

Cytokine release syndrome (CRS) was observed in 3 patients (24%) (Table 4). All CRS events were grade 1 and resolved spontaneously with no requirement for tocilizumab or steroid administration. Cytokines associated with the occurrence of CRS, such as IL-6 and IL1Rα, and C-reactive protein (CRP) were elevated in the plasma of patients developing clinical signs of CRS. Neurotoxicity was not observed.

Six patients developed a non-pruritic, non-tender, maculopapular skin rash. None of the patients required specific treatment for the rash as it resolved spontaneously within 3-7 days.

TABLE 4

Grade 3 or Higher Adverse Events and Adverse Events of Special Interest of Classical HL Patients from LCCC 1532-ATL

| Adverse Events (of Special Interests or >Grade 3): n (%) | Benda (n = 8) | Flu/Benda (n = 18) |
|---|---|---|
| Lymphopenia | 8 (100) | 18 (100) |
| Leukopenia | 3 (38) | 8 (44) |
| Neutropenia | 2 (25) | 7 (39) |
| Thrombocytopenia | 1 (13) | 7 (39) |
| Anemia | 0 | 3 (17) |
| Hypoalbuminemia | 0 | 0 |
| Hyponatremia | 0 | 0 |
| Dyspnea | 0 | 0 |
| Rash | 0 | 0 |
| Headache | 0 | 0 |
| Pharyngitis | 0 | 1 (6) |
| Lung Infection | 0 | 1 (6) |
| Cytokine Release Syndrome (all Grade 1) | 1 (13) | 2 (11) |
| Grade 3/4 Neutropenia at day 28 | 0 | 2 (11) |
| Grade 3/4 Thrombocytopenia at day 28 | 0 | 6 (33) |
| Grade 3/4 Anemia at day 28 | 0 | 0 |
| Prolonged Grade 3/4 Neutropenia (at month 3)* | 0 | 0 |
| Prolonged Grade 3/4 Thrombocytopenia (at month 3)* | 0 | 3 (17) |
| Prolonged Grade 3/4 Anemia (at month 3)* | 0 | 1 (6) |
| Rash (Any Grade) | 2 (25) | 4 (22) |

Benda = bendamustine; Flu = fludarabine; LD = lymphodepletion;
*3 patients did not have data at 3 months as they withdrew from study.

There were Grade 3 or higher toxicities reported during the first 6 weeks, and most of them were hematologic and consistent with toxicities caused by the conditioning chemotherapy. Grade 3 or higher toxicities included lymphopenia, leukopenia, neutropenia, thrombocytopenia, anemia, hypoalbuminemia, hyponatremia, dyspnea, pharyngitis, lung infection and headache (Table 4). Grade 3/4 neutropenia (ANC <1.0/mL) that had not resolved by Day 28 day occurred in 2 patients. However, both patients resolved their Grade 3/4 neutropenia by Day 90. Six patients had Grade 3/4 thrombocytopenia (platelets <50,000/mL) that had not resolved by Day 28. Three patients had Grade 3/4 thrombocytopenia at Month 3 (Table 4).

Incidence of Grade 3 or higher AEs in patients treated with bendamustine and fludarabine was low (Table 4), which included leukopenia (44%), neutropenia (39%), hypoalbuminemia (0%), hyponatremia (0%), dyspnea, pharyngitis, lung infection and headache (0%). One patient experienced Grade 3 acute kidney injury and hypotension after receiving the first dose of fludarabine and bendamustine, but prior to CD30.CAR-T cell infusion. This patient did not complete the scheduled lymphodepletion regimen, but their symptoms subsequently resolved and they received the scheduled dose of CD30.CAR-T cells.

1.5 CONCLUSIONS

Patients receiving lymphodepletion using bendamustine and fludarabine followed by CD30.CAR-T cell infusion display improved overall response and complete response rates as compared to response rates reported for Patients receiving lymphodepletion using bendamustine and fludarabine followed by CD30.CAR-T cell infusion in Ramos et al., Biol Blood Marrow Transplant 25 (2019) S7-S75, Abstract 79.

Ramos et al. reports preliminary data for NCT02917083 (RELY-30), wherein 10 relapsed/refractory HL patients received cyclophosphamide 500 mg/m$^2$ and fludarabine 30 mg/m$^2$ daily for 3 days, and were subsequently administered CD30.CAR T cells. Out of 9 patients evaluated at 6 weeks after infusion, 6 had CR, and 3 patients had disease progression (i.e. ORR=66.6%, CR=66.6%). Three of the 9 patients progressed (PD=33.3%).

By contrast, in the present Example, 13 out of 16 patients that received bendamustine 70 mg/m$^2$ and fludarabine 30 mg/m$^2$ daily for 3 days and were subsequently administered CD30.CAR T cells displayed a clinical response (i.e. CR+PR; ORR=81.3%), and 12 of these patients displayed a complete response (CR=75%). Only two of the 16 patients progressed (PD=12.5%).

The results identify benda/flu treatment as a promising conditioning lymphodepleting therapy for use in methods of treatment employing CD30.CAR-T cells.

> Example 2: Study TESSCAR001 (NCT04268706): A Phase 2. Multicenter, Open Label, Single Arm Study Designed to Evaluate the Efficacy and Safety of CD30-Directed Genetically Modified Autologous T-Cells (CD30.CAR-T) in Adult and Pediatric Patients with Relapsed or Refractory CD30-Positive cHL

2.1 STUDY RATIONALE

As the outcomes for patients with relapsed or refractory cHL who have failed standard available therapy are poor, new treatment approaches are urgently needed for this population. Example demonstrates that CD30.CAR-T cell therapy is well tolerated, and that such cells have significant clinical activity in heavily pretreated patients with relapsed or refractory cHL. Higher rates of clinical response were found to be correlated with the use of lymphodepleting chemotherapy relative to response rates reported by Ramos et al., J Clin Invest. (2017) 127(9):3462-3471 for therapy with CD30.CAR-T cells without lymphodepleting chemotherapy (NCT01316146). The favourable toxicity profile and encouraging antitumor activity of autologous CD30.CAR-T demonstrated in Example 1 provides strong support for further investigation in patients with relapsed or refractory cHL.

2.2 OBJECTIVES AND ENDPOINTS 2.2.1 Primary Objectives

The anti-tumor effect of autologous CD30.CAR-T are evaluated using ORR (as assessed by an Independent Radiology Review Committee (IRRC) per the Revised Criteria for Response Assessment: The Lugano Classification (Cheson et al., J Clin Oncol (2014) 32: 3059-3068)).

The ORR is defined as the proportion of patients with a Best Overall Response (BOR) of CR or PR. The BOR is defined as the best disease response recorded from CD30.CAR-T infusion until progressive disease, or start of new anti-cancer therapy, whichever comes first.

2.2.2 Secondary Objectives

The following are assessed:

Safety of autologous CD30.CAR-T

Additional antitumor effect of autologous CD30.CAR-T including:

Objective Response Rate (ORR) as assessed by the Investigator per the Revised Criteria for Response Assessment: The Lugano Classification (Cheson et al., J Clin Oncol (2014) 32: 3059-3068)

Duration of Response (DOR)

Progression Free Survival (PFS)

Overall Survival (OS)

Health Related Quality of Life (HRQoL) assessments

All secondary efficacy endpoints are analyzed in the Full Analysis Set (FAS) unless specified otherwise.

2.3 STUDY POPULATION

The study population includes adults and pediatric patients aged 12 to 75 years with relapsed or refractory CD30 positive cHL who have failed at least 3 prior lines of therapy, including:

Chemotherapy

*BV and/or

A *PD-1 inhibitor

*Unless BV or PD-1 inhibitor is contraindicated.

Patients may have previously received an autologous and/or allogeneic stem cell transplant.

2.4 STUDY DESIGN

The study is a Phase 2, open-label, multicenter study designed to evaluate the efficacy and safety of CD30-directed genetically modified autologous T-cells (CD30.CAR-T) in adult and pediatric patients with relapsed or refractory CD30-positive cHL.

Approximately 82 patients are enrolled (to yield 66 evaluable adult patients), at approximately 30 investigative sites in the United States, Canada and European Union. Approximately 5 pediatric patients ≥12 years of age are enrolled and analyzed separately from the adult population.

Figure 4:
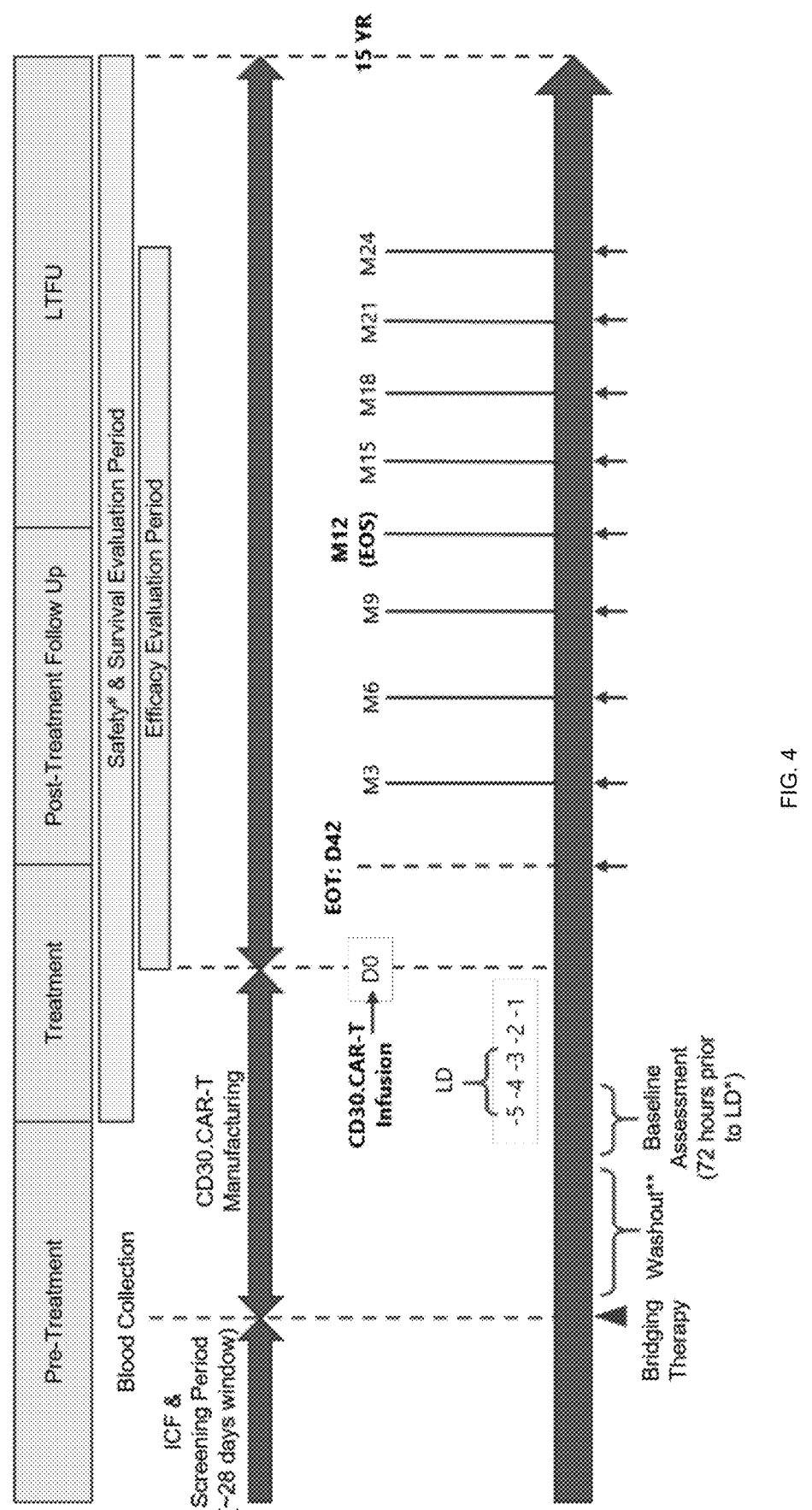
FIG. 4. Schematic overview of TESSCAR001 (NCT04268706) and TESSCAR002 study procedures. *Reimaging scan can be done within 1 week prior to LD; **The washout period will be based on the type of therapy used; #LD and CD30.CAR-T-association safety evaluation to be performed from Treatment Phase until LTFU Phase. T Tumor response assessments. Abbreviations: LTFU, long term follow up; ICF, informed consent form; LD, lymphodepletion chemotherapy; EOT, end of treatment; EOS, end of study; M, month; YR, year.

An overview of the study design and study procedures is provided in FIGS. 3 and 4.

2.5 STUDY TREATMENT 2.5.1 Lymphodepletion Chemotherapy

Patient will undergo LD chemotherapy with fludarabine (30 mg/m$^2$/day) (IV infusion over 30 minutes) and bendamustine (70 mg/m$^2$/day) (IV infusion over 30 minutes) given via IV infusion for 3 consecutive days, starting 5 days prior to CD30.CAR-T infusion (i.e. Day −5).

2.5.1 CD30.CAR-T Infusion

CD30.CAR-T cells will be administered on Day 0 as a single IV infusion at a dose of 2×10$^8$ cells/m$^2$. In patients that weigh less than 50 kg, a weight-based dosing of 2.0 to $5.0 \times 10^6$ cells per kg body weight will be used.

Example 3: Study TESSCAR002: A Phase 1, Study of CD30-Directed Genetically Modified Autologous T-Cells (CD30.CART) in Patients with Relapsed or Refractory CD30 Positive Non-Hodgkin Lymphoma

3.1 STUDY RATIONALE

CD30 is a validated target for CD30-positive hematologic malignancies. This is further supported by the approval of anti-CD30 antibody drug conjugate, brentuximab vedotin, for classical HL and some NHL subtypes including systemic and cutaneous ALCL, PTCL and mycosis fungoides.

CD30 is widely expressed in NHL subtype tumor cells, with expression ranged from 100% in ALCL (Gottesman, Pathology and Laboratory Medicine International (2016) 8: 27-36) to 19% in PMBCL (Hoeller et al., Histopathology (2010) 56: 217-228) tumor cells. The high expression of CD30 positivity in NHL cells further support the potential targeting of NHL malignancies with CD30 antigens.

The standard of care therapy for NHL malignancies across all subtypes is not curative. Treatment outcomes for patients with relapsed or refractory NHL who fail standard available therapy are poor. New treatment strategies for this patient population are urgently needed to meet unmet clinical needs.

The favorable toxicity profile and encouraging antitumor activity of autologous CD30.CAR-T demonstrated in Example 1 provide strong rationale to expand the study to NHL patients to fulfill important unmet clinical needs.

3.2 OBJECTIVES AND ENDPOINTS 3.2.1 Primary Objectives

To evaluate the safety and dose-limiting toxicities (DLTs) of autologous CD30.CAR-T and determine the recommended Phase 2 dose (RP2D).

3.2.2 Secondary Objectives

To evaluate the preliminary antitumor effects and pharmacokinetics of autologous CD30.CAR-T by assessing
  Objective response rate (ORR)
  Pharmacokinetics of autologous CD30.CAR-T cells in the blood.
  Duration of response (DoR)
  Progression free survival (PFS)
  Overall Survival (OS)

3.2.3 Exploratory Objectives

To assess:
  Immunogenicity against anti-CD30 scFv (single-chain variable fragment) following CD30.CAR-T infusion in blood
  Cytokine profiling in blood
  Immunological parameters in blood
  Tumor markers in blood and tumor tissue
  Circulating tumor DNA (ctDNA) in blood

3.3 STUDY POPULATION

The study population includes adult patients 18-75 years of age with relapsed or refractory CD30 positive NHL, who have failed standard of care therapy; patients may or may not have received an autologous or allogenic HSCT.

The CD30-positive NHL subtypes to be evaluated include:
  ALCL
  PTCL-NOS

ENKTCL, nasal type
DLBCL-NOS
PMBCL

Prospective approval of protocol deviations from recruitment and enrollment criteria, also known as protocol waivers or exemptions, is not permitted.

3.4 STUDY DESIGN

This is a phase 1, open-label, multi-center dose-escalation study designed to evaluate the safety and preliminary antitumor effects of CD30-directed genetically modified autologous T-cells (CD30.CAR-T) in adult patients with relapsed or refractory CD30-positive NHL and to determine the R2PD. Patients who have failed standard therapy and may or may not have received an autologous or allogenic HSCT will be enrolled. Up to 4 study centers will participate in the study.

The CD30-positive NHL subtypes to be evaluated include:
  ALCL
  PTCL-NOS
  ENKTCL, nasal type
  DLBCL-NOS
  PMBCL Overall, this study enrolls approximately 12-21 patients.

A fresh tumor biopsy is required at the time of screening to determine CD30 positivity and confirm study eligibility. If a biopsy is medically contraindicated and an archival tumor biopsy from a recent treatment that documents CD30 positivity is available (including the original diagnostic biopsy if that is the only available tissue), may be accepted after discussion with Sponsor or designee. CD30-positivity are confirmed locally for eligibility. CD30 positivity must be confirmed prior to blood collection for CD30.CAR-T cells manufacturing.

After blood collection and during the production of CD30.CAR-T, patients are allowed to receive bridging therapy as per investigator choice. If bridging therapy is administered, washout is required after the completion of bridging therapy, to ensure adequate recovery from toxicity(ies) before initiation of the first dose of lymphodepletion chemotherapy. The washout period is based on the type of agent used as bridging therapy.

All patients go through a baseline assessment for safety which is performed within 72 hours prior to lymphodepletion chemotherapy. Imaging scans for tumor assessment can be performed within 7 days prior to lymphodepletion chemotherapy. Patients must have active disease [PR, SD or progressive disease (PD)] documented by imaging prior to starting lymphodepletion chemotherapy and CD30.CAR-T infusion. Patients with evidence of a CR following bridging therapy may not be treated with CD30.CAR-T until documented progression/active disease.

Lymphodepletion chemotherapy and CD30.CAR-T infusion can be administered on an outpatient basis. Patients may also be hospitalized for the administration of lymphodepletion chemotherapy and CD30.CAR-T infusion per institutional guidance.

Lymphodepletion chemotherapy—consisting of fludarabine (30 mg/m²/day) and bendamustine (70 mg/m²/day)—is administered for 3 consecutive days starting on Day −5 to Day −3, prior to autologous CD30.CAR-T infusion on Day 0.

Prior to CD30.CAR-T infusion, all patients are premedicated with a H1 antagonist (e.g. diphenhydramine, hydroxyzine) up to 1 mg/kg IV (max 50 mg) and acetaminophen 10 mg/kg per oral (max 650 mg). Alternative antihistamines, anti-inflammatories and anti-emetics may be prescribed per institutional guidance. The use of steroids such as glucocorticoids must be avoided.

CD30.CAR-T cells are administered on Day 0 as a single IV infusion. Subjects return daily to the treatment facility for safety monitoring for 14 days post-infusion, and then weekly thereafter at weeks 3, 4 and 6 post-infusion.

Patients are monitored for DLT assessment from after CD30.CAR-T infusion through Day 28. Any of the toxicities which are assessed as possibly related, probably related, or definitely related to autologous CD30.CAR-T cells are considered as a DLT. The DLT assessment period commences from the start of autologous CD30.CAR-T infusion and continue for 28 days following the infusion of CD30.CAR-T cells. DLTs which occur during the DLT assessment period is used in decisions regarding dose-escalation. The RP2D is established during the study.

All patients are evaluated for safety following lymphodepletion chemotherapy to CD30.CAR-T infusion through Day 42 (EOT) at pre-determined timepoints during the Treatment Phase. Post CD30.CAR-T infusion, patients are required to stay in the treating facility for an additional 4 hours, then return daily for 14 days (excluding weekends), followed by a weekly visit on Day 21 and Day 28 for safety monitoring and then on Day 42 for EOT visit. Per institutional guidance, patients may remain hospitalized post-CD30.CAR-T infusion for toxicity monitoring. The extended hospitalization is not considered an AE.

Imaging scans are reviewed locally by the investigator as assessed by the Revised Lugano Response Criteria (Cheson et al., J Clin Oncol (2014) 32: 3059-3068).

Patients undergo exploratory biomarker assessments to characterize the pharmacokinetic properties as well as the immunogenicity and immunological properties of autologous CD30.CAR-T. Details on prioritization of blood samples collected for analysis are included in the Laboratory Manual. Blood and tissue biopsy samples are collected, if clinically feasible as assessed by the investigator, at various timepoints before and during study treatment. These data are used to analyze further the mechanisms that govern therapeutic outcome as well as to identify potential biomarkers that correlate with therapeutic efficacy and/or failure.

After the EOT visit at Day 42, patients enter the Post-Treatment Follow-Up Phase which ends at M12. Follow-up for safety, efficacy and survival continue every 3 months. After that, patients enter into long term follow-up (LTFU); follow-up for efficacy continue every 3 months until M24; follow up for safety and survival continue every 6 months from M13 through M60 (Year 5) and annually thereafter for up to 15 years until disease progression, death, withdrawal of consent, start of new anti-cancer therapy or termination of study.

Figure 5:
FIG. 5. Schematic overview of TESSCAR002 study design. $ Subjects may be replaced if they are unable to complete follow-up through the DLT period for any reason other than a DLT. § A minimum of 3 patients is required to complete the DLT assessment period before a decision can be taken to escalate the dose for the next patient. At each new dose level, 1st and 2nd patient will be dosed 4 weeks apart; if no DLT detected from the 1st patient, the 2nd and 3rd patient can be dosed concurrently. Dose-escalation/de-escalation to be performed until at least 6 patients have been evaluated at the highest dose with acceptable safety (i.e. 'acceptable safety' is when the BOIN recommends to either stay at same dose level or escalate), or until a total of approximately 21 patients have been dosed. #Dose will be de-escalated to DL0 1×10$^8$/m2 CD30.CAR-T cells in the event of 1 DLT in 1 patient, or 1 DLT among 2 patients, or 2 DLTs among 3 patients at DL1. Abbreviations: DOR, Duration of response; ORR, Objective response rate; OS, Overall survival; PFS, Progression free survival; PK, Pharmacokinetics; RP2D, Recommended Phase 2 dose.

An overview of the study design and study procedures is provided in FIGS. 4 and 5.

3.5 STUDY TREATMENT 3.5.1 Lymphodepletion Chemotherapy

Patient will undergo LD chemotherapy with fludarabine (30 mg/m$^2$/day) (IV infusion over 30 minutes) and bendamustine (70 mg/m$^2$/day) given via IV infusion for 3 consecutive days, starting 5 days prior to CD30.CAR-T infusion (i.e. Day −5).

3.5.2 CD30.CAR-T Infusion

CD30.CAR-T cells will be administered on Day 0 as a single IV infusion at:

DL1: 2×10$^8$ cells/m$^2$

DL2: 4×10$^8$ cells/m$^2$

DL3: 6×10$^8$ cells/m$^2$

---

The invention claimed is:

1. A method of treating a CD30-positive cancer in a subject, comprising:
    (a) administering a lymphodepleting chemotherapy to the subject, and
    (b) subsequently administering CD30-specific chimeric antigen receptor (CAR)-expressing T cells to the subject, wherein the CD30-specific CAR-expressing T cells comprise a CAR comprising:
        (i) an antigen-binding domain which binds specifically to CD30,
        (ii) a transmembrane domain, and
        (iii) a signalling domain, wherein the signalling domain comprises an amino acid sequence derived from the intracellular domain of CD28, and an amino acid sequence comprising an immunoreceptor tyrosine-based activation motif (ITAM), wherein the CAR comprises the amino acid sequence of SEQ ID NO:35 or 36; and wherein the method has an objective response rate (ORR) of at least 75%.

2. The method according to claim 1, wherein administering a lymphodepleting chemotherapy to the subject comprises administering fludarabine and bendamustine.

3. The method according to claim 1, wherein the method comprises administering fludarabine at a dose of 15 to 60 mg/m² per day, for 2 to 6 consecutive days.

4. The method according to claim 1, wherein the method comprises administering fludarabine at a dose of 30 mg/m$^2$ per day, for 3 consecutive days.

5. The method according to claim 1, wherein the method comprises administering bendamustine at a dose of 35 to 140 mg/m$^2$ per day, for 2 to 6 consecutive days.

6. The method according to claim 1, wherein the method comprises administering bendamustine at a dose of 70 mg/m$^2$ per day, for 3 consecutive days.

7. The method according to claim 1, wherein the method comprises administering 5×10$^7$ CD30-specific CAR-expressing T cells/m$^2$ to 1×10$^9$ CD30-specific CAR-expressing T cells/m$^2$ to the subject.

8. The method according to claim 1, wherein the method comprises administering 1×10$^8$ CD30-specific CAR-expressing T cells/m$^2$ to 6×10$^8$ CD30-specific CAR-expressing T cells/m$^2$ to the subject.

9. The method according to claim 1, wherein the method comprises:

(i) administering fludarabine at a dose of 30 mg/m$^2$ per day and bendamustine at a dose of 70 mg/m$^2$ per day to a subject for 3 consecutive days, and (ii) subsequently administering CD30-specific CAR-expressing T cells to the subject at a dose of 2×10$^8$ CD30-specific CAR-expressing T cells/m$^2$ to 6×10$^8$ CD30-specific CAR-expressing T cells/m$^2$.

10. The method according to claim 1, wherein the CD30-positive cancer is selected from: a hematological cancer, a solid cancer, a hematopoietic malignancy, Hodgkin's lymphoma, anaplastic large cell lymphoma, peripheral T cell lymphoma, peripheral T cell lymphoma not otherwise specified, T cell leukemia, T cell lymphoma, cutaneous T cell lymphoma, NK-T cell lymphoma, extranodal NK-T cell lymphoma, non-Hodgkin's lymphoma, B cell non-Hodgkin's lymphoma, diffuse large B cell lymphoma, diffuse large B cell lymphoma not otherwise specified, EBV-positive B cell lymphoma, EBV-positive diffuse large B cell lymphoma, primary mediastinal B cell lymphoma, advanced systemic mastocytosis, a germ cell tumor and testicular embryonal carcinoma.

11. The method according to claim 1, wherein the subject has previously failed therapy for the CD30-positive cancer.

12. The method according to claim 1, wherein the CD30-positive cancer is a relapsed or refractory CD30-positive cancer.

\* \* \* \* \*

SEQUENCE LISTING

<160> NUMBER OF SEQ ID NOS: 36

<210> SEQ ID NO 1
<211> LENGTH: 595
<212> TYPE: PRT
<213> ORGANISM: Homo sapiens

<400> SEQUENCE: 1

```
Met Arg Val Leu Leu Ala Ala Leu Gly Leu Leu Phe Leu Gly Ala Leu
1               5                   10                  15

Arg Ala Phe Pro Gln Asp Arg Pro Phe Glu Asp Thr Cys His Gly Asn
            20                  25                  30

Pro Ser His Tyr Tyr Asp Lys Ala Val Arg Arg Cys Cys Tyr Arg Cys
        35                  40                  45

Pro Met Gly Leu Phe Pro Thr Gln Gln Cys Pro Gln Arg Pro Thr Asp
    50                  55                  60

Cys Arg Lys Gln Cys Glu Pro Asp Tyr Tyr Leu Asp Glu Ala Asp Arg
65                  70                  75                  80

Cys Thr Ala Cys Val Thr Cys Ser Arg Asp Asp Leu Val Glu Lys Thr
                85                  90                  95

Pro Cys Ala Trp Asn Ser Ser Arg Val Cys Glu Cys Arg Pro Gly Met
                100                 105                 110

Phe Cys Ser Thr Ser Ala Val Asn Ser Cys Ala Arg Cys Phe Phe His
            115                 120                 125
```

-continued

```
Ser Val Cys Pro Ala Gly Met Ile Val Lys Phe Pro Gly Thr Ala Gln
    130             135                 140

Lys Asn Thr Val Cys Glu Pro Ala Ser Pro Gly Val Ser Pro Ala Cys
145             150                 155                 160

Ala Ser Pro Glu Asn Cys Lys Glu Pro Ser Ser Gly Thr Ile Pro Gln
                165                 170                 175

Ala Lys Pro Thr Pro Val Ser Pro Ala Thr Ser Ser Ala Ser Thr Met
            180                 185                 190

Pro Val Arg Gly Gly Thr Arg Leu Ala Gln Glu Ala Ala Ser Lys Leu
            195                 200                 205

Thr Arg Ala Pro Asp Ser Pro Ser Ser Val Gly Arg Pro Ser Ser Asp
    210                 215                 220

Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Glu Ala Gly Arg Cys
                245                 250                 255

Thr Ala Cys Val Ser Cys Ser Arg Asp Asp Leu Val Glu Lys Thr Pro
            260                 265                 270

Cys Ala Trp Asn Ser Ser Arg Thr Cys Glu Cys Arg Pro Gly Met Ile
            275                 280                 285

Cys Ala Thr Ser Ala Thr Asn Ser Cys Ala Arg Cys Val Pro Tyr Pro
    290                 295                 300

Ile Cys Ala Ala Glu Thr Val Thr Lys Pro Gln Asp Met Ala Glu Lys
305                 310                 315                 320

Asp Thr Thr Phe Glu Ala Pro Pro Leu Gly Thr Gln Pro Asp Cys Asn
                325                 330                 335

Pro Thr Pro Glu Asn Gly Glu Ala Pro Ala Ser Thr Ser Pro Thr Gln
            340                 345                 350

Ser Leu Leu Val Asp Ser Gln Ala Ser Lys Thr Leu Pro Ile Pro Thr
            355                 360                 365

Ser Ala Pro Val Ala Leu Ser Ser Thr Gly Lys Pro Val Leu Asp Ala
    370                 375                 380

Gly Pro Val Leu Phe Trp Val Ile Leu Val Leu Val Val Val Val Gly
385                 390                 395                 400

Ser Ser Ala Phe Leu Leu Cys His Arg Arg Ala Cys Arg Lys Arg Ile
                405                 410                 415

Arg Gln Lys Leu His Leu Cys Tyr Pro Val Gln Thr Ser Gln Pro Lys
            420                 425                 430

Leu Glu Leu Val Asp Ser Arg Pro Arg Arg Ser Ser Thr Gln Leu Arg
            435                 440                 445

Ser Gly Ala Ser Val Thr Glu Pro Val Ala Glu Glu Arg Gly Leu Met
    450                 455                 460

Ser Gln Pro Leu Met Glu Thr Cys His Ser Val Gly Ala Ala Tyr Leu
465                 470                 475                 480

Glu Ser Leu Pro Leu Gln Asp Ala Ser Pro Ala Gly Gly Pro Ser Ser
                485                 490                 495

Pro Arg Asp Leu Pro Glu Pro Arg Val Ser Thr Glu His Thr Asn Asn
            500                 505                 510

Lys Ile Glu Lys Ile Tyr Ile Met Lys Ala Asp Thr Val Ile Val Gly
            515                 520                 525

Thr Val Lys Ala Glu Leu Pro Glu Gly Arg Gly Leu Ala Gly Pro Ala
    530                 535                 540

Glu Pro Glu Leu Glu Glu Glu Leu Glu Ala Asp His Thr Pro His Tyr
```

-continued

```
545                550                555                560

Pro Glu Gln Glu Thr Glu Pro Pro Leu Gly Ser Cys Ser Asp Val Met
               565                570                575

Leu Ser Val Glu Glu Glu Gly Lys Glu Asp Pro Leu Pro Thr Ala Ala
               580                585                590

Ser Gly Lys
       595

<210> SEQ ID NO 2
<211> LENGTH: 132
<212> TYPE: PRT
<213> ORGANISM: Homo sapiens

<400> SEQUENCE: 2

Met Ser Gln Pro Leu Met Glu Thr Cys His Ser Val Gly Ala Ala Tyr
1               5                10                15

Leu Glu Ser Leu Pro Leu Gln Asp Ala Ser Pro Ala Gly Gly Pro Ser
               20                25                30

Ser Pro Arg Asp Leu Pro Glu Pro Arg Val Ser Thr Glu His Thr Asn
       35                40                45

Asn Lys Ile Glu Lys Ile Tyr Ile Met Lys Ala Asp Thr Val Ile Val
       50                55                60

Gly Thr Val Lys Ala Glu Leu Pro Glu Gly Arg Gly Leu Ala Gly Pro
65                70                75                80

Ala Glu Pro Glu Leu Glu Glu Glu Leu Glu Ala Asp His Thr Pro His
               85                90                95

Tyr Pro Glu Gln Glu Thr Glu Pro Pro Leu Gly Ser Cys Ser Asp Val
               100                105                110

Met Leu Ser Val Glu Glu Glu Gly Lys Glu Asp Pro Leu Pro Thr Ala
       115                120                125

Ala Ser Gly Lys
       130

<210> SEQ ID NO 3
<211> LENGTH: 483
<212> TYPE: PRT
<213> ORGANISM: Homo sapiens

<400> SEQUENCE: 3

Met Phe Cys Ser Thr Ser Ala Val Asn Ser Cys Ala Arg Cys Phe Phe
1               5                10                15

His Ser Val Cys Pro Ala Gly Met Ile Val Lys Phe Pro Gly Thr Ala
               20                25                30

Gln Lys Asn Thr Val Cys Glu Pro Ala Ser Pro Gly Val Ser Pro Ala
       35                40                45

Cys Ala Ser Pro Glu Asn Cys Lys Glu Pro Ser Ser Gly Thr Ile Pro
       50                55                60

Gln Ala Lys Pro Thr Pro Val Ser Pro Ala Thr Ser Ser Ala Ser Thr
65                70                75                80

Met Pro Val Arg Gly Gly Thr Arg Leu Ala Gln Glu Ala Ala Ser Lys
               85                90                95

Leu Thr Arg Ala Pro Asp Ser Pro Ser Ser Val Gly Arg Pro Ser Ser
               100                105                110

Asp Pro Gly Leu Ser Pro Thr Gln Pro Cys Pro Glu Gly Ser Gly Asp
       115                120                125

Cys Arg Lys Gln Cys Glu Pro Asp Tyr Tyr Leu Asp Glu Ala Gly Arg
```

-continued

```
            130               135               140

Cys Thr Ala Cys Val Ser Cys Ser Arg Asp Asp Leu Val Glu Lys Thr
145               150               155               160

Pro Cys Ala Trp Asn Ser Ser Arg Thr Cys Glu Cys Arg Pro Gly Met
                  165               170               175

Ile Cys Ala Thr Ser Ala Thr Asn Ser Cys Ala Arg Cys Val Pro Tyr
                  180               185               190

Pro Ile Cys Ala Ala Glu Thr Val Thr Lys Pro Gln Asp Met Ala Glu
                  195               200               205

Lys Asp Thr Thr Phe Glu Ala Pro Pro Leu Gly Thr Gln Pro Asp Cys
            210               215               220

Asn Pro Thr Pro Glu Asn Gly Glu Ala Pro Ala Ser Thr Ser Pro Thr
225               230               235               240

Gln Ser Leu Leu Val Asp Ser Gln Ala Ser Lys Thr Leu Pro Ile Pro
                  245               250               255

Thr Ser Ala Pro Val Ala Leu Ser Ser Thr Gly Lys Pro Val Leu Asp
                  260               265               270

Ala Gly Pro Val Leu Phe Trp Val Ile Leu Val Leu Val Val Val Val
            275               280               285

Gly Ser Ser Ala Phe Leu Leu Cys His Arg Arg Ala Cys Arg Lys Arg
290               295               300

Ile Arg Gln Lys Leu His Leu Cys Tyr Pro Val Gln Thr Ser Gln Pro
305               310               315               320

Lys Leu Glu Leu Val Asp Ser Arg Pro Arg Arg Ser Ser Thr Leu Arg
                  325               330               335

Ser Gly Ala Ser Val Thr Glu Pro Val Ala Glu Glu Arg Gly Leu Met
                  340               345               350

Ser Gln Pro Leu Met Glu Thr Cys His Ser Val Gly Ala Ala Tyr Leu
            355               360               365

Glu Ser Leu Pro Leu Gln Asp Ala Ser Pro Ala Gly Gly Pro Ser Ser
            370               375               380

Pro Arg Asp Leu Pro Glu Pro Arg Val Ser Thr Glu His Thr Asn Asn
385               390               395               400

Lys Ile Glu Lys Ile Tyr Ile Met Lys Ala Asp Thr Val Ile Val Gly
                  405               410               415

Thr Val Lys Ala Glu Leu Pro Glu Gly Arg Gly Leu Ala Gly Pro Ala
                  420               425               430

Glu Pro Glu Leu Glu Glu Glu Leu Glu Ala Asp His Thr Pro His Tyr
                  435               440               445

Pro Glu Gln Glu Thr Glu Pro Pro Leu Gly Ser Cys Ser Asp Val Met
            450               455               460

Leu Ser Val Glu Glu Glu Gly Lys Glu Asp Pro Leu Pro Thr Ala Ala
465               470               475               480

Ser Gly Lys
```

```
<210> SEQ ID NO 4
<211> LENGTH: 18
<212> TYPE: PRT
<213> ORGANISM: Homo sapiens

<400> SEQUENCE: 4

Met Arg Val Leu Leu Ala Ala Leu Gly Leu Leu Phe Leu Gly Ala Leu
1               5               10               15

Arg Ala
```

-continued

```
<210> SEQ ID NO 5
<211> LENGTH: 367
<212> TYPE: PRT
<213> ORGANISM: Homo sapiens

<400> SEQUENCE: 5

Phe Pro Gln Asp Arg Pro Phe Glu Asp Thr Cys His Gly Asn Pro Ser
1               5                   10                  15

His Tyr Tyr Asp Lys Ala Val Arg Arg Cys Cys Tyr Arg Cys Pro Met
            20                  25                  30

Gly Leu Phe Pro Thr Gln Gln Cys Pro Gln Arg Pro Thr Asp Cys Arg
        35                  40                  45

Lys Gln Cys Glu Pro Asp Tyr Tyr Leu Asp Glu Ala Asp Arg Cys Thr
    50                  55                  60

Ala Cys Val Thr Cys Ser Arg Asp Asp Leu Val Glu Lys Thr Pro Cys
65                  70                  75                  80

Ala Trp Asn Ser Ser Arg Val Cys Glu Cys Arg Pro Gly Met Phe Cys
                85                  90                  95

Ser Thr Ser Ala Val Asn Ser Cys Ala Arg Cys Phe Phe His Ser Val
            100                 105                 110

Cys Pro Ala Gly Met Ile Val Lys Phe Pro Gly Thr Ala Gln Lys Asn
        115                 120                 125

Thr Val Cys Glu Pro Ala Ser Pro Gly Val Ser Pro Ala Cys Ala Ser
    130                 135                 140

Pro Glu Asn Cys Lys Glu Pro Ser Ser Gly Thr Ile Pro Gln Ala Lys
145                 150                 155                 160

Pro Thr Pro Val Ser Pro Ala Thr Ser Ser Ala Ser Thr Met Pro Val
                165                 170                 175

Arg Gly Gly Thr Arg Leu Ala Gln Glu Ala Ala Ser Lys Leu Thr Arg
            180                 185                 190

Ala Pro Asp Ser Pro Ser Ser Val Gly Arg Pro Ser Ser Asp Pro Gly
        195                 200                 205

Leu Ser Pro Thr Gln Pro Cys Pro Glu Gly Ser Gly Asp Cys Arg Lys
    210                 215                 220

Gln Cys Glu Pro Asp Tyr Tyr Leu Asp Glu Ala Gly Arg Cys Thr Ala
225                 230                 235                 240

Cys Val Ser Cys Ser Arg Asp Asp Leu Val Glu Lys Thr Pro Cys Ala
                245                 250                 255

Trp Asn Ser Ser Arg Thr Cys Glu Cys Arg Pro Gly Met Ile Cys Ala
            260                 265                 270

Thr Ser Ala Thr Asn Ser Cys Ala Arg Cys Val Pro Tyr Pro Ile Cys
        275                 280                 285

Ala Ala Glu Thr Val Thr Lys Pro Gln Asp Met Ala Glu Lys Asp Thr
    290                 295                 300

Thr Phe Glu Ala Pro Pro Leu Gly Thr Gln Pro Asp Cys Asn Pro Thr
305                 310                 315                 320

Pro Glu Asn Gly Glu Ala Pro Ala Ser Thr Ser Pro Thr Gln Ser Leu
                325                 330                 335

Leu Val Asp Ser Gln Ala Ser Lys Thr Leu Pro Ile Pro Thr Ser Ala
            340                 345                 350

Pro Val Ala Leu Ser Ser Thr Gly Lys Pro Val Leu Asp Ala Gly
        355                 360                 365
```

```
<210> SEQ ID NO 6
<211> LENGTH: 21
<212> TYPE: PRT
<213> ORGANISM: Homo sapiens

<400> SEQUENCE: 6

Pro Val Leu Phe Trp Val Ile Leu Val Leu Val Val Val Gly Ser
1               5                   10                  15

Ser Ala Phe Leu Leu
            20

<210> SEQ ID NO 7
<211> LENGTH: 189
<212> TYPE: PRT
<213> ORGANISM: Homo sapiens

<400> SEQUENCE: 7

Cys His Arg Arg Ala Cys Arg Lys Arg Ile Arg Gln Lys Leu His Leu
1               5                   10                  15

Cys Tyr Pro Val Gln Thr Ser Gln Pro Lys Leu Glu Leu Val Asp Ser
            20                  25                  30

Arg Pro Arg Arg Ser Ser Thr Gln Leu Arg Ser Gly Ala Ser Val Thr
        35                  40                  45

Glu Pro Val Ala Glu Glu Arg Gly Leu Met Ser Gln Pro Leu Met Glu
    50                  55                  60

Thr Cys His Ser Val Gly Ala Ala Tyr Leu Glu Ser Leu Pro Leu Gln
65                  70                  75                  80

Asp Ala Ser Pro Ala Gly Gly Pro Ser Ser Pro Arg Asp Leu Pro Glu
                85                  90                  95

Pro Arg Val Ser Thr Glu His Thr Asn Asn Lys Ile Glu Lys Ile Tyr
            100                 105                 110

Ile Met Lys Ala Asp Thr Val Ile Val Gly Thr Val Lys Ala Glu Leu
            115                 120                 125

Pro Glu Gly Arg Gly Leu Ala Gly Pro Ala Glu Pro Glu Leu Glu Glu
        130                 135                 140

Glu Leu Glu Ala Asp His Thr Pro His Tyr Pro Glu Gln Glu Thr Glu
145                 150                 155                 160

Pro Pro Leu Gly Ser Cys Ser Asp Val Met Leu Ser Val Glu Glu Glu
                165                 170                 175

Gly Lys Glu Asp Pro Leu Pro Thr Ala Ala Ser Gly Lys
            180                 185

<210> SEQ ID NO 8
<211> LENGTH: 8
<212> TYPE: PRT
<213> ORGANISM: Artificial Sequence
<220> FEATURE:
<223> OTHER INFORMATION: synthetic construct

<400> SEQUENCE: 8

Gly Tyr Thr Phe Thr Thr Tyr Thr
1               5

<210> SEQ ID NO 9
<211> LENGTH: 8
<212> TYPE: PRT
<213> ORGANISM: Artificial Sequence
<220> FEATURE:
<223> OTHER INFORMATION: synthetic construct

<400> SEQUENCE: 9
```

```
Ile Asn Pro Ser Ser Gly Cys Ser
1               5

<210> SEQ ID NO 10
<211> LENGTH: 16
<212> TYPE: PRT
<213> ORGANISM: Artificial Sequence
<220> FEATURE:
<223> OTHER INFORMATION: synthetic construct

<400> SEQUENCE: 10

Ala Arg Arg Ala Asp Tyr Gly Asn Tyr Glu Tyr Thr Trp Phe Ala Tyr
1               5                   10                  15

<210> SEQ ID NO 11
<211> LENGTH: 6
<212> TYPE: PRT
<213> ORGANISM: Artificial Sequence
<220> FEATURE:
<223> OTHER INFORMATION: synthetic construct

<400> SEQUENCE: 11

Gln Asn Val Gly Thr Asn
1               5

<210> SEQ ID NO 12
<211> LENGTH: 3
<212> TYPE: PRT
<213> ORGANISM: Artificial Sequence
<220> FEATURE:
<223> OTHER INFORMATION: synthetic construct

<400> SEQUENCE: 12

Ser Ala Ser
1

<210> SEQ ID NO 13
<211> LENGTH: 9
<212> TYPE: PRT
<213> ORGANISM: Artificial Sequence
<220> FEATURE:
<223> OTHER INFORMATION: synthetic construct

<400> SEQUENCE: 13

Gln Gln Tyr His Thr Tyr Pro Leu Thr
1               5

<210> SEQ ID NO 14
<211> LENGTH: 123
<212> TYPE: PRT
<213> ORGANISM: Artificial Sequence
<220> FEATURE:
<223> OTHER INFORMATION: synthetic construct

<400> SEQUENCE: 14

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
                20                  25                  30

Thr Ile His Trp Val Arg Arg Pro Gly His Asp Leu Glu Trp Ile
            35                  40                  45

Gly Tyr Ile Asn Pro Ser Ser Gly Cys Ser Asp Tyr Asn Gln Asn Phe
    50                  55                  60

Lys Gly Lys Thr Thr Leu Thr Ala Asp Lys Ser Ser Asn Thr Ala Tyr
```

```
65                  70                  75                  80

Met Gln Leu Asn Ser Leu Thr Ser Glu Asp Ser Ala Val Tyr Tyr Cys
                85                  90                  95

Ala Arg Arg Ala Asp Tyr Gly Asn Tyr Glu Tyr Thr Trp Phe Ala Tyr
            100                 105                 110

Trp Gly Gln Gly Thr Thr Val Thr Val Ser Ser
        115                 120

<210> SEQ ID NO 15
<211> LENGTH: 107
<212> TYPE: PRT
<213> ORGANISM: Artificial Sequence
<220> FEATURE:
<223> OTHER INFORMATION: synthetic construct

<400> SEQUENCE: 15

Val Ile Glu Leu Thr Gln Ser Pro Lys Phe Met Ser Thr Ser Val Gly
1               5                   10                  15

Asp Arg Val Asn Val Thr Tyr Lys Ala Ser Gln Asn Val Gly Thr Asn
            20                  25                  30

Val Ala Trp Phe Gln Gln Lys Pro Gly Gln Ser Pro Lys Val Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr His Thr Tyr Pro Leu
                85                  90                  95

Thr Phe Gly Gly Gly Thr Lys Leu Glu Ile Lys
            100                 105

<210> SEQ ID NO 16
<211> LENGTH: 5
<212> TYPE: PRT
<213> ORGANISM: Artificial Sequence
<220> FEATURE:
<223> OTHER INFORMATION: synthetic construct

<400> SEQUENCE: 16

Gly Gly Gly Gly Ser
1               5

<210> SEQ ID NO 17
<211> LENGTH: 15
<212> TYPE: PRT
<213> ORGANISM: Artificial Sequence
<220> FEATURE:
<223> OTHER INFORMATION: synthetic construct

<400> SEQUENCE: 17

Ser Gly Gly Gly Ser Gly Gly Gly Ser Gly Gly Gly Ser
1               5                   10                  15

<210> SEQ ID NO 18
<211> LENGTH: 245
<212> TYPE: PRT
<213> ORGANISM: Artificial Sequence
<220> FEATURE:
<223> OTHER INFORMATION: synthetic construct

<400> SEQUENCE: 18

Gln Val Gln Leu Gln Gln Ser Gly Ala Glu Leu Ala Arg Pro Gly Ala
```

-continued

```
1               5               10              15

Ser Val Lys Met Ser Cys Lys Ala Ser Gly Tyr Thr Phe Thr Thr Tyr
            20              25              30

Thr Ile His Trp Val Arg Arg Arg Pro Gly His Asp Leu Glu Trp Ile
            35              40              45

Gly Tyr Ile Asn Pro Ser Ser Gly Cys Ser Asp Tyr Asn Gln Asn Phe
    50              55              60

Lys Gly Lys Thr Thr Leu Thr Ala Asp Lys Ser Ser Asn Thr Ala Tyr
65              70              75              80

Met Gln Leu Asn Ser Leu Thr Ser Glu Asp Ser Ala Val Tyr Tyr Cys
            85              90              95

Ala Arg Arg Ala Asp Tyr Gly Asn Tyr Glu Tyr Thr Trp Phe Ala Tyr
            100             105             110

Trp Gly Gln Gly Thr Thr Val Thr Val Ser Ser Ser Gly Gly Gly Ser
            115             120             125

Gly Gly Gly Gly Ser Gly Gly Gly Ser Val Ile Glu Leu Thr Gln
            130             135             140

Ser Pro Lys Phe Met Ser Thr Ser Val Gly Asp Arg Val Asn Val Thr
145             150             155             160

Tyr Lys Ala Ser Gln Asn Val Gly Thr Asn Val Ala Trp Phe Gln Gln
            165             170             175

Lys Pro Gly Gln Ser Pro Lys Val Leu Ile Tyr Ser Ala Ser Tyr Arg
            180             185             190

Tyr Ser Gly Val Pro Asp Arg Phe Thr Gly Ser Gly Ser Gly Thr Asp
            195             200             205

Phe Thr Leu Thr Ile Ser Asn Val Gln Ser Glu Asp Leu Ala Glu Tyr
    210             215             220

Phe Cys Gln Gln Tyr His Thr Tyr Pro Leu Thr Phe Gly Gly Gly Thr
225             230             235             240

Lys Leu Glu Ile Lys
                245
```

<210> SEQ ID NO 19
<211> LENGTH: 151
<212> TYPE: PRT
<213> ORGANISM: Artificial Sequence
<220> FEATURE:
<223> OTHER INFORMATION: synthetic construct

<400> SEQUENCE: 19

```
Ala Thr Ser Ser Ala Ser Thr Met Pro Val Arg Gly Gly Thr Arg Leu
1               5               10              15

Ala Gln Glu Ala Ala Ser Lys Leu Thr Arg Ala Pro Asp Ser Pro Ser
            20              25              30

Ser Val Gly Arg Pro Ser Ser Asp Pro Gly Leu Ser Pro Thr Gln Pro
            35              40              45

Cys Pro Glu Gly Ser Gly Asp Cys Arg Lys Gln Cys Glu Pro Asp Tyr
    50              55              60

Tyr Leu Asp Glu Ala Gly Arg Cys Thr Ala Cys Val Ser Cys Ser Arg
65              70              75              80

Asp Asp Leu Val Glu Lys Thr Pro Cys Ala Trp Asn Ser Ser Arg Thr
            85              90              95

Cys Glu Cys Arg Pro Gly Met Ile Cys Ala Thr Ser Ala Thr Asn Ser
            100             105             110

Cys Ala Arg Cys Val Pro Tyr Pro Ile Cys Ala Ala Glu Thr Val Thr
```

-continued

```
            115                 120                 125
Lys Pro Gln Asp Met Ala Glu Lys Asp Thr Thr Phe Glu Ala Pro Pro
    130                 135                 140

Leu Gly Thr Gln Pro Asp Cys
145                 150

<210> SEQ ID NO 20
<211> LENGTH: 24
<212> TYPE: PRT
<213> ORGANISM: Artificial Sequence
<220> FEATURE:
<223> OTHER INFORMATION: synthetic construct

<400> SEQUENCE: 20

Phe Trp Val Leu Val Val Val Gly Gly Val Leu Ala Cys Tyr Ser Leu
1               5                   10                  15

Leu Val Thr Val Ala Phe Ile Ile
            20

<210> SEQ ID NO 21
<211> LENGTH: 21
<212> TYPE: PRT
<213> ORGANISM: Artificial Sequence
<220> FEATURE:
<223> OTHER INFORMATION: synthetic construct

<400> SEQUENCE: 21

Leu Cys Tyr Leu Leu Asp Gly Ile Leu Phe Ile Tyr Gly Val Ile Leu
1               5                   10                  15

Thr Ala Leu Phe Leu
            20

<210> SEQ ID NO 22
<211> LENGTH: 28
<212> TYPE: PRT
<213> ORGANISM: Artificial Sequence
<220> FEATURE:
<223> OTHER INFORMATION: synthetic construct

<400> SEQUENCE: 22

Ile Tyr Ile Trp Ala Pro Leu Ala Gly Thr Cys Gly Val Leu Leu Leu
1               5                   10                  15

Ser Leu Val Ile Thr Leu Tyr Cys Asn His Arg Asn
            20                  25

<210> SEQ ID NO 23
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa = L or I

<400> SEQUENCE: 23

Tyr Xaa Xaa Xaa
1

<210> SEQ ID NO 24
```

```
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa = L or I
<220> FEATURE:
<221> NAME/KEY: misc_feature
<222> LOCATION: (5)..(10)
<223> OTHER INFORMATION: Xaa can be any naturally occurring amino acid
<220> FEATURE:
<221> NAME/KEY: MISC_FEATURE
<222> LOCATION: (11)..(12)
<223> OTHER INFORMATION: Xaa = absent or any amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Xaa = L or I

<400> SEQUENCE: 24

Tyr Xaa Xaa Xaa Xaa Xaa Xaa Xaa Xaa Xaa Xaa Xaa Tyr Xaa Xaa Xaa
1               5                   10                  15

<210> SEQ ID NO 25
<211> LENGTH: 112
<212> TYPE: PRT
<213> ORGANISM: Artificial Sequence
<220> FEATURE:
<223> OTHER INFORMATION: synthetic construct

<400> SEQUENCE: 25

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 26
<211> LENGTH: 44
<212> TYPE: PRT
<213> ORGANISM: Artificial Sequence
<220> FEATURE:
<223> OTHER INFORMATION: synthetic construct

<400> SEQUENCE: 26

Phe Trp Val Arg Ser Lys Arg Ser Arg Leu Leu His Ser Asp Tyr Met
1               5                   10                  15
```

```
Asn Met Thr Pro Arg Arg Pro Gly Pro Thr Arg Lys His Tyr Gln Pro
            20                  25                  30

Tyr Ala Pro Pro Arg Asp Phe Ala Ala Tyr Arg Ser
        35                  40

<210> SEQ ID NO 27
<211> LENGTH: 44
<212> TYPE: PRT
<213> ORGANISM: Artificial Sequence
<220> FEATURE:
<223> OTHER INFORMATION: synthetic construct

<400> SEQUENCE: 27

Phe Trp Val Arg Ser Lys Arg Ser Arg Leu Leu His Ser Asp Tyr Met
1               5                   10                  15

Asn Met Thr Pro Arg Arg Pro Gly Pro Thr Arg Lys His Tyr Gln Ala
            20                  25                  30

Tyr Ala Ala Ala Arg Asp Phe Ala Ala Tyr Arg Ser
        35                  40

<210> SEQ ID NO 28
<211> LENGTH: 156
<212> TYPE: PRT
<213> ORGANISM: Artificial Sequence
<220> FEATURE:
<223> OTHER INFORMATION: synthetic construct

<400> SEQUENCE: 28

Phe Trp Val Arg Ser Lys Arg Ser Arg Leu Leu His Ser Asp Tyr Met
1               5                   10                  15

Asn Met Thr Pro Arg Arg Pro Gly Pro Thr Arg Lys His Tyr Gln Pro
            20                  25                  30

Tyr Ala Pro Pro Arg Asp Phe Ala Ala Tyr Arg Ser Arg Val Lys Phe
        35                  40                  45

Ser Arg Ser Ala Asp Ala Pro Ala Tyr Gln Gln Gly Gln Asn Gln Leu
    50                  55                  60

Tyr Asn Glu Leu Asn Leu Gly Arg Arg Glu Glu Tyr Asp Val Leu Asp
65                  70                  75                  80

Lys Arg Arg Gly Arg Asp Pro Glu Met Gly Gly Lys Pro Arg Arg Lys
                85                  90                  95

Asn Pro Gln Glu Gly Leu Tyr Asn Glu Leu Gln Lys Asp Lys Met Ala
            100                 105                 110

Glu Ala Tyr Ser Glu Ile Gly Met Lys Gly Glu Arg Arg Arg Gly Lys
            115                 120                 125

Gly His Asp Gly Leu Tyr Gln Gly Leu Ser Thr Ala Thr Lys Asp Thr
        130                 135                 140

Tyr Asp Ala Leu His Met Gln Ala Leu Pro Pro Arg
145                 150                 155

<210> SEQ ID NO 29
<211> LENGTH: 12
<212> TYPE: PRT
<213> ORGANISM: Homo sapiens

<400> SEQUENCE: 29

Glu Pro Lys Ser Cys Asp Lys Thr His Thr Cys Pro
1               5                   10

<210> SEQ ID NO 30
<211> LENGTH: 12
```

-continued

```
<212> TYPE: PRT
<213> ORGANISM: Homo sapiens

<400> SEQUENCE: 30

Glu Pro Lys Ser Pro Asp Lys Thr His Thr Cys Pro
1               5                   10

<210> SEQ ID NO 31
<211> LENGTH: 220
<212> TYPE: PRT
<213> ORGANISM: Homo sapiens

<400> SEQUENCE: 31

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
            195                 200                 205

Tyr Thr Gln Lys Ser Leu Ser Leu Ser Pro Gly Lys
        210                 215                 220

<210> SEQ ID NO 32
<211> LENGTH: 223
<212> TYPE: PRT
<213> ORGANISM: Homo sapiens

<400> SEQUENCE: 32

Pro Cys Pro Ala Pro Pro Val Ala Gly Pro Ser Val Phe Leu Phe Pro
1               5                   10                  15

Pro Lys Pro Lys Asp Thr Leu Met Ile Ala Arg Thr Pro Glu Val Thr
                20                  25                  30

Cys Val Val Val Asp Val Ser His Glu Asp Pro Glu Val Lys Phe Asn
            35                  40                  45

Trp Tyr Val Asp Gly Val Glu Val His Asn Ala Lys Thr Lys Pro Arg
        50                  55                  60

Glu Glu Gln Tyr Asn Ser Thr Tyr Arg Val Val Ser Val Leu Thr Val
```

-continued

```
65                  70                  75                  80

Leu His Gln Asp Trp Leu Asn Gly Lys Glu Tyr Lys Cys Lys Val Ser
                85                  90                  95

Asn Lys Ala Leu Pro Ala Pro Ile Glu Lys Thr Ile Ser Lys Ala Lys
                100                 105                 110

Gly Gln Pro Arg Glu Pro Gln Val Tyr Thr Leu Pro Pro Ser Arg Asp
                115                 120                 125

Glu Leu Thr Lys Asn Gln Val Ser Leu Thr Cys Leu Val Lys Gly Phe
        130                 135                 140

Tyr Pro Ser Asp Ile Ala Val Glu Trp Glu Ser Asn Gly Gln Pro Glu
145                 150                 155                 160

Asn Asn Tyr Lys Thr Thr Pro Pro Val Leu Asp Ser Asp Gly Ser Phe
                165                 170                 175

Phe Leu Tyr Ser Lys Leu Thr Val Asp Lys Ser Arg Trp Gln Gln Gly
                180                 185                 190

Asn Val Phe Ser Cys Ser Val Met His Glu Ala Leu His Asn His Tyr
                195                 200                 205

Thr Gln Lys Ser Leu Ser Leu Ser Pro Gly Lys Lys Asp Pro Lys
        210                 215                 220
```

<210> SEQ ID NO 33
<211> LENGTH: 232
<212> TYPE: PRT
<213> ORGANISM: Artificial Sequence
<220> FEATURE:
<223> OTHER INFORMATION: synthetic construct

<400> SEQUENCE: 33

```
Glu Pro Lys Ser Pro Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
```

```
         210             215             220

Ser Leu Ser Leu Ser Pro Gly Lys
225                 230

<210> SEQ ID NO 34
<211> LENGTH: 20
<212> TYPE: PRT
<213> ORGANISM: Artificial Sequence
<220> FEATURE:
<223> OTHER INFORMATION: synthetic construct

<400> SEQUENCE: 34

Met Asp Phe Gln Val Gln Ile Phe Ser Phe Leu Leu Ile Ser Ala Ser
1               5                   10                  15

Val Ile Met Ser
            20

<210> SEQ ID NO 35
<211> LENGTH: 666
<212> TYPE: PRT
<213> ORGANISM: Artificial Sequence
<220> FEATURE:
<223> OTHER INFORMATION: synthetic construct

<400> SEQUENCE: 35

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
                20                  25                  30

Thr Ile His Trp Val Arg Arg Arg Pro Gly His Asp Leu Glu Trp Ile
            35                  40                  45

Gly Tyr Ile Asn Pro Ser Ser Gly Cys Ser Asp Tyr Asn Gln Asn Phe
        50                  55                  60

Lys Gly Lys Thr Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Ala Asp Tyr Gly Asn Tyr Glu Tyr Thr Trp Phe Ala Tyr
                100                 105                 110

Trp Gly Gln Gly Thr Thr Val Thr Val Ser Ser Ser Gly Gly Gly Ser
            115                 120                 125

Gly Gly Gly Gly Ser Gly Gly Gly Ser Val Ile Glu Leu Thr Gln
        130                 135                 140

Ser Pro Lys Phe Met Ser Thr Ser Val Gly Asp Arg Val Asn Val Thr
145                 150                 155                 160

Tyr Lys Ala Ser Gln Asn Val Gly Thr Asn Val Ala Trp Phe Gln Gln
                165                 170                 175

Lys Pro Gly Gln Ser Pro Lys Val Leu Ile Tyr Ser Ala Ser Tyr Arg
                180                 185                 190

Tyr Ser Gly Val Pro Asp Arg Phe Thr Gly Ser Gly Ser Gly Thr Asp
                195                 200                 205

Phe Thr Leu Thr Ile Ser Asn Val Gln Ser Glu Asp Leu Ala Glu Tyr
        210                 215                 220

Phe Cys Gln Gln Tyr His Thr Tyr Pro Leu Thr Phe Gly Gly Gly Thr
225                 230                 235                 240

Lys Leu Glu Ile Lys Arg Ser Asp Pro Ala Glu Pro Lys Ser Pro Asp
                245                 250                 255
```

-continued

```
Lys Thr His Thr Cys Pro Pro Cys Pro Ala Pro Glu Leu Leu Gly Gly
        260             265             270

Pro Ser Val Phe Leu Phe Pro Pro Lys Pro Lys Asp Thr Leu Met Ile
        275             280             285

Ser Arg Thr Pro Glu Val Thr Cys Val Val Val Asp Val Ser His Glu
        290             295             300

Asp Pro Glu Val Lys Phe Asn Trp Tyr Val Asp Gly Val Glu Val His
305             310             315             320

Asn Ala Lys Thr Lys Pro Arg Glu Glu Gln Tyr Asn Ser Thr Tyr Arg
        325             330             335

Val Val Ser Val Leu Thr Val Leu His Gln Asp Trp Leu Asn Gly Lys
        340             345             350

Glu Tyr Lys Cys Lys Val Ser Asn Lys Ala Leu Pro Ala Pro Ile Glu
        355             360             365

Lys Thr Ile Ser Lys Ala Lys Gly Gln Pro Arg Glu Pro Gln Val Tyr
        370             375             380

Thr Leu Pro Pro Ser Arg Asp Glu Leu Thr Lys Asn Gln Val Ser Leu
385             390             395             400

Thr Cys Leu Val Lys Gly Phe Tyr Pro Ser Asp Ile Ala Val Glu Trp
            405             410             415

Glu Ser Asn Gly Gln Pro Glu Asn Asn Tyr Lys Thr Thr Pro Pro Val
            420             425             430

Leu Asp Ser Asp Gly Ser Phe Phe Leu Tyr Ser Lys Leu Thr Val Asp
        435             440             445

Lys Ser Arg Trp Gln Gln Gly Asn Val Phe Ser Cys Ser Val Met His
        450             455             460

Glu Ala Leu His Asn His Tyr Thr Gln Lys Ser Leu Ser Leu Ser Pro
465             470             475             480

Gly Lys Lys Asp Pro Lys Phe Trp Val Leu Val Val Val Gly Gly Val
            485             490             495

Leu Ala Cys Tyr Ser Leu Leu Val Thr Val Ala Phe Ile Ile Phe Trp
            500             505             510

Val Arg Ser Lys Arg Ser Arg Leu Leu His Ser Asp Tyr Met Asn Met
        515             520             525

Thr Pro Arg Arg Pro Gly Pro Thr Arg Lys His Tyr Gln Pro Tyr Ala
        530             535             540

Pro Pro Arg Asp Phe Ala Ala Tyr Arg Ser Arg Val Lys Phe Ser Arg
545             550             555             560

Ser Ala Asp Ala Pro Ala Tyr Gln Gln Gly Gln Asn Gln Leu Tyr Asn
            565             570             575

Glu Leu Asn Leu Gly Arg Arg Glu Glu Tyr Asp Val Leu Asp Lys Arg
        580             585             590

Arg Gly Arg Asp Pro Glu Met Gly Gly Lys Pro Arg Arg Lys Asn Pro
        595             600             605

Gln Glu Gly Leu Tyr Asn Glu Leu Gln Lys Asp Lys Met Ala Glu Ala
        610             615             620

Tyr Ser Glu Ile Gly Met Lys Gly Glu Arg Arg Arg Gly Lys Gly His
625             630             635             640

Asp Gly Leu Tyr Gln Gly Leu Ser Thr Ala Thr Lys Asp Thr Tyr Asp
            645             650             655

Ala Leu His Met Gln Ala Leu Pro Pro Arg
        660             665
```

```
<210> SEQ ID NO 36
<211> LENGTH: 689
<212> TYPE: PRT
<213> ORGANISM: Artificial Sequence
<220> FEATURE:
<223> OTHER INFORMATION: synthetic construct

<400> SEQUENCE: 36

Met Asp Phe Gln Val Gln Ile Phe Ser Phe Leu Leu Ile Ser Ala Ser
1               5                   10                  15

Val Ile Met Ser Arg Met Ala Gln Val Gln Leu Gln Gln Ser Gly Ala
            20                  25                  30

Glu Leu Ala Arg Pro Gly Ala Ser Val Lys Met Ser Cys Lys Ala Ser
        35                  40                  45

Gly Tyr Thr Phe Thr Thr Tyr Thr Ile His Trp Val Arg Arg Arg Pro
    50                  55                  60

Gly His Asp Leu Glu Trp Ile Gly Tyr Ile Asn Pro Ser Ser Gly Cys
65                  70                  75                  80

Ser Asp Tyr Asn Gln Asn Phe Lys Gly Lys Thr Thr Leu Thr Ala Asp
                85                  90                  95

Lys Ser Ser Asn Thr Ala Tyr Met Gln Leu Asn Ser Leu Thr Ser Glu
            100                 105                 110

Asp Ser Ala Val Tyr Tyr Cys Ala Arg Arg Ala Asp Tyr Gly Asn Tyr
        115                 120                 125

Glu Tyr Thr Trp Phe Ala Tyr Trp Gly Gln Gly Thr Thr Val Thr Val
    130                 135                 140

Ser Ser Ser Gly Gly Gly Ser Gly Gly Gly Gly Ser Gly Gly Gly Gly
145                 150                 155                 160

Ser Val Ile Glu Leu Thr Gln Ser Pro Lys Phe Met Ser Thr Ser Val
                165                 170                 175

Gly Asp Arg Val Asn Val Thr Tyr Lys Ala Ser Gln Asn Val Gly Thr
            180                 185                 190

Asn Val Ala Trp Phe Gln Gln Lys Pro Gly Gln Ser Pro Lys Val Leu
        195                 200                 205

Ile Tyr Ser Ala Ser Tyr Arg Tyr Ser Gly Val Pro Asp Arg Phe Thr
    210                 215                 220

Gly Ser Gly Ser Gly Thr Asp Phe Thr Leu Thr Ile Ser Asn Val Gln
225                 230                 235                 240

Ser Glu Asp Leu Ala Glu Tyr Phe Cys Gln Gln Tyr His Thr Tyr Pro
                245                 250                 255

Leu Thr Phe Gly Gly Gly Thr Lys Leu Glu Ile Lys Arg Ser Asp Pro
            260                 265                 270

Ala Glu Pro Lys Ser Pro Asp Lys Thr His Thr Cys Pro Pro Cys Pro
        275                 280                 285

Ala Pro Glu Leu Leu Gly Gly Pro Ser Val Phe Leu Phe Pro Pro Lys
    290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
        355                 360                 365

Gln Asp Trp Leu Asn Gly Lys Glu Tyr Lys Cys Lys Val Ser Asn Lys
```

-continued

```
        370                375                380
Ala Leu Pro Ala Pro Ile Glu Lys Thr Ile Ser Lys Ala Lys Gly Gln
385                390                395                400

Pro Arg Glu Pro Gln Val Tyr Thr Leu Pro Pro Ser Arg Asp Glu Leu
                405                410                415

Thr Lys Asn Gln Val Ser Leu Thr Cys Leu Val Lys Gly Phe Tyr Pro
                420                425                430

Ser Asp Ile Ala Val Glu Trp Glu Ser Asn Gly Gln Pro Glu Asn Asn
                435                440                445

Tyr Lys Thr Thr Pro Pro Val Leu Asp Ser Asp Gly Ser Phe Phe Leu
    450                455                460

Tyr Ser Lys Leu Thr Val Asp Lys Ser Arg Trp Gln Gln Gly Asn Val
465                470                475                480

Phe Ser Cys Ser Val Met His Glu Ala Leu His Asn His Tyr Thr Gln
                485                490                495

Lys Ser Leu Ser Leu Ser Pro Gly Lys Lys Asp Pro Lys Phe Trp Val
                500                505                510

Leu Val Val Val Gly Gly Val Leu Ala Cys Tyr Ser Leu Leu Val Thr
                515                520                525

Val Ala Phe Ile Ile Phe Trp Val Arg Ser Lys Arg Ser Arg Leu Leu
    530                535                540

His Ser Asp Tyr Met Asn Met Thr Pro Arg Arg Pro Gly Pro Thr Arg
545                550                555                560

Lys His Tyr Gln Pro Tyr Ala Pro Pro Arg Asp Phe Ala Ala Tyr Arg
                565                570                575

Ser Arg Val Lys Phe Ser Arg Ser Ala Asp Ala Pro Ala Tyr Gln Gln
                580                585                590

Gly Gln Asn Gln Leu Tyr Asn Glu Leu Asn Leu Gly Arg Arg Glu Glu
                595                600                605

Tyr Asp Val Leu Asp Lys Arg Arg Gly Arg Asp Pro Glu Met Gly Gly
    610                615                620

Lys Pro Arg Arg Lys Asn Pro Gln Glu Gly Leu Tyr Asn Glu Leu Gln
625                630                635                640

Lys Asp Lys Met Ala Glu Ala Tyr Ser Glu Ile Gly Met Lys Gly Glu
                645                650                655

Arg Arg Arg Gly Lys Gly His Asp Gly Leu Tyr Gln Gly Leu Ser Thr
                660                665                670

Ala Thr Lys Asp Thr Tyr Asp Ala Leu His Met Gln Ala Leu Pro Pro
                675                680                685

Arg
```